US008945569B2

(12) United States Patent
Gurney et al.

(10) Patent No.: US 8,945,569 B2
(45) Date of Patent: Feb. 3, 2015

(54) JAGGED-BINDING AGENTS AND USES THEREOF

(75) Inventors: Austin L. Gurney, San Francisco, CA (US); Timothy Charles Hoey, Hillsborough, CA (US); Aaron Ken Sato, Burlingame, CA (US); Alexandra Lazetic, San Jose, CA (US); Zhimin Ji, Palo Alto, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 180 days.

(21) Appl. No.: 13/510,666

(22) PCT Filed: Nov. 19, 2010

(86) PCT No.: PCT/US2010/057432
§ 371 (c)(1),
(2), (4) Date: Aug. 16, 2012

(87) PCT Pub. No.: WO2011/063237
PCT Pub. Date: May 26, 2011

(65) Prior Publication Data
US 2012/0301489 A1    Nov. 29, 2012

Related U.S. Application Data

(60) Provisional application No. 61/262,879, filed on Nov. 19, 2009.

(51) Int. Cl.
*A61K 38/00* (2006.01)
*C07K 16/28* (2006.01)
*A61K 39/395* (2006.01)
*A61K 39/00* (2006.01)

(52) U.S. Cl.
CPC ......... *C07K 16/2896* (2013.01); *A61K 39/3955* (2013.01); *A61K 2039/505* (2013.01); *C07K 317/73* (2013.01); *C07K 2317/76* (2013.01); *C07K 2317/92* (2013.01)
USPC ................ 424/174.1; 424/184.1; 530/388.15; 530/388.8

(58) Field of Classification Search
None
See application file for complete search history.

(56) References Cited

U.S. PATENT DOCUMENTS

| | | | |
|---|---|---|---|
| 5,780,300 A | 7/1998 | Artavanis-Tsakonas et al. |
| 5,789,195 A | 8/1998 | Artavanis-Tsakonas et al. |
| 5,856,441 A | 1/1999 | Artavanis-Tsakonas et al. |
| 5,869,282 A | 2/1999 | Ish-Horowicz et al. |
| 6,004,924 A | 12/1999 | Ish-Horowicz et al. |
| 6,083,904 A | 7/2000 | Artavanis-Tsakonas et al. |
| 6,136,952 A | 10/2000 | Li et al. |
| 6,149,902 A | 11/2000 | Artavanis-Tsakonas et al. |
| 6,433,138 B1 | 8/2002 | Zimrin et al. |
| 6,689,744 B2 | 2/2004 | Gao et al. |
| 6,703,489 B1 | 3/2004 | Ish-Horowicz et al. |
| 6,716,974 B1 | 4/2004 | Maciag et al. |
| 6,825,007 B2 | 11/2004 | Zimrin et al. |
| 6,887,475 B1 | 5/2005 | Lamb et al. |
| 2001/0048930 A1 | 12/2001 | Lamb et al. |
| 2002/0151487 A1 | 10/2002 | Nickoloff et al. |
| 2003/0082651 A1 | 5/2003 | Gao et al. |
| 2003/0083465 A1 | 5/2003 | Zimrin et al. |
| 2003/0157090 A1 | 8/2003 | Benvenuto et al. |
| 2003/0185829 A1 | 10/2003 | Koller et al. |
| 2003/0194804 A1 | 10/2003 | Lamb et al. |
| 2004/0037815 A1 | 2/2004 | Clarke et al. |
| 2004/0053869 A1 | 3/2004 | Andrews et al. |
| 2004/0058443 A1 | 3/2004 | Artavanis-Tsakonas et al. |
| 2004/0102401 A1 | 5/2004 | Dean et al. |
| 2004/0213797 A1 | 10/2004 | Bodmer et al. |
| 2004/0241180 A1 | 12/2004 | Lamb et al. |
| 2004/0253602 A1 | 12/2004 | Maciag et al. |
| 2005/0003406 A1 | 1/2005 | Coignet |
| 2005/0025751 A1 | 2/2005 | Bodmer et al. |
| 2005/0026831 A1 | 2/2005 | Bodmer et al. |
| 2005/0032725 A1 | 2/2005 | Rao et al. |
| 2005/0089518 A1 | 4/2005 | Clarke et al. |
| 2005/0112121 A1 | 5/2005 | Artavanis-Tsakonas et al. |
| 2005/0129686 A1 | 6/2005 | Coignet |
| 2005/0137130 A1 | 6/2005 | Bodmer et al. |
| 2005/0158859 A1 | 7/2005 | Artavanis-Tsakonas et al. |
| 2005/0201975 A1 | 9/2005 | Champion et al. |
| 2005/0220886 A1 | 10/2005 | Bodmer et al. |
| 2005/0232927 A1 | 10/2005 | Clarke et al. |
| 2005/0239064 A1 | 10/2005 | Artavanis-Tsakonas et al. |
| 2005/0261477 A1 | 11/2005 | Champion et al. |

(Continued)

FOREIGN PATENT DOCUMENTS

WO    WO 2008/042236 A2    4/2008

OTHER PUBLICATIONS

International Search Report mailed Jul. 27, 2011 from the International Searching Authority for International Application No. PCT/US10/57432, 7 pages.
Written Opinion of the International Searching Authority mailed Jul. 27, 2011 for International Application No. PCT/US10/57432, 6 pages.
International Preliminary Report on Patentability issued May 22, 2012 from the International Bureau of WIPO for International Application No. PCT/US2010/57432, 7 pages.

(Continued)

*Primary Examiner* — Sean Aeder
*Assistant Examiner* — Julie Wu
(74) *Attorney, Agent, or Firm* — Sterne, Kessler, Goldstein & Fox P.L.L.C.

(57) ABSTRACT

Antibodies that specifically bind to an extracellular domain of human Jagged1 or human Jagged2 and modulate Jagged activity, and methods of using said antibodies to inhibit tumor growth are disclosed. Also described are methods of treating cancer comprising administering a therapeutically effect amount of an anti-Jagged antibody to a patient having a tumor or cancer.

23 Claims, 14 Drawing Sheets

(56) References Cited

U.S. PATENT DOCUMENTS

Figure 1:
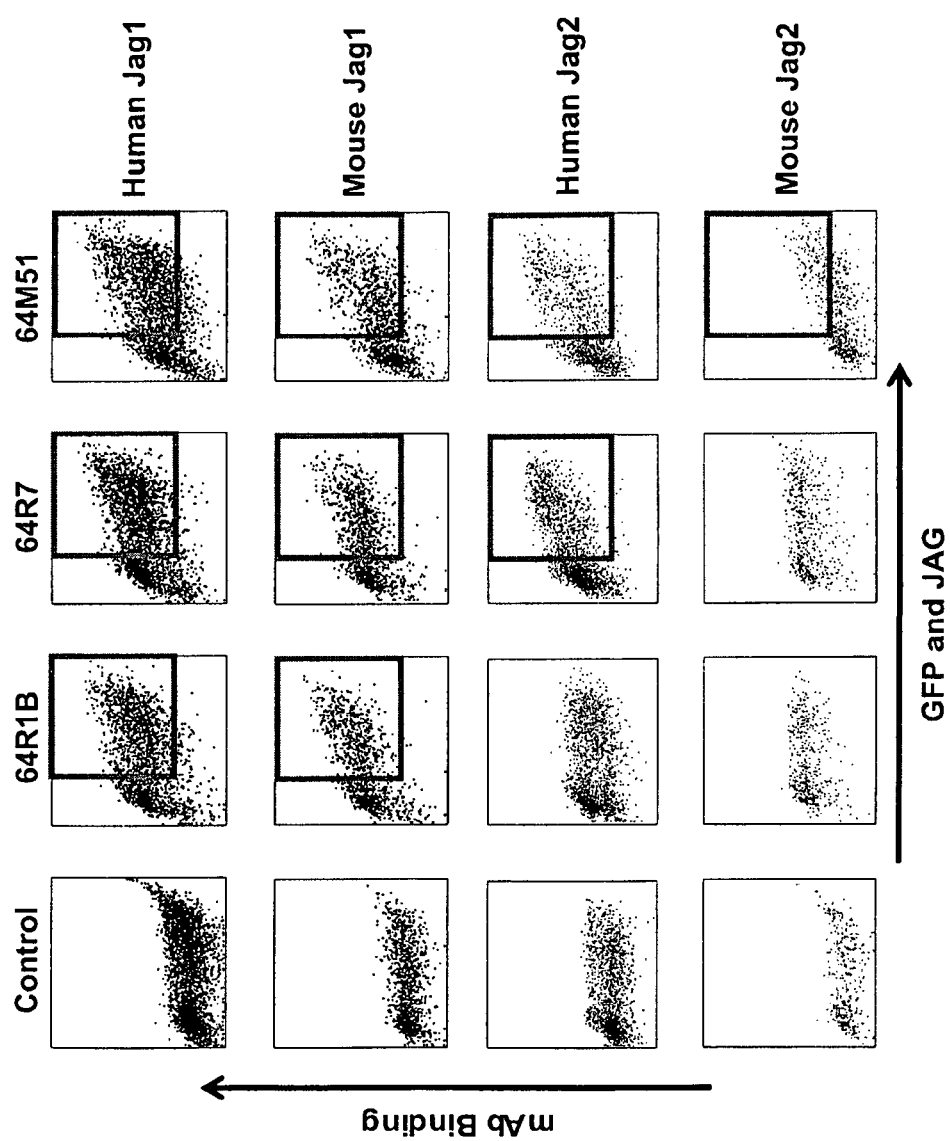

| | | |
|---|---|---|
| 2006/0034857 A1 | 2/2006 | Lamb et al. |
| 2006/0063253 A1 | 3/2006 | Maciag et al. |
| 2006/0083682 A1 | 4/2006 | Bergstein |
| 2006/0084588 A1 | 4/2006 | Briend et al. |
| 2006/0128619 A1 | 6/2006 | Champion et al. |
| 2006/0140943 A1 | 6/2006 | Champion et al. |
| 2006/0147435 A1 | 7/2006 | Moon et al. |
| 2006/0177451 A1 | 8/2006 | van den Oudenrijn et al. |
| 2007/0003983 A1 | 1/2007 | Artavanis-Tsakonas et al. |
| 2007/0026518 A1 | 2/2007 | Healy et al. |
| 2007/0036800 A1 | 2/2007 | Bergstein |
| 2007/0036801 A1 | 2/2007 | Bergstein |
| 2007/0036802 A1 | 2/2007 | Bergstein |
| 2007/0036803 A1 | 2/2007 | Bergstein |
| 2007/0036804 A1 | 2/2007 | Bergstein |
| 2007/0041984 A1 | 2/2007 | Bergstein |
| 2007/0071675 A1 | 3/2007 | Wu et al. |
| 2008/0064049 A1 | 3/2008 | Clarke et al. |
| 2008/0178305 A1 | 7/2008 | Clarke et al. |
| 2008/0317760 A1 | 12/2008 | Gurney et al. |
| 2009/0041783 A1 | 2/2009 | Takayama et al. |
| 2009/0081238 A1 | 3/2009 | Siebel et al. |
| 2009/0092612 A1* | 4/2009 | Takayama et al. ......... 424/139.1 |
| 2009/0280128 A1 | 11/2009 | Kamogawa et al. |

OTHER PUBLICATIONS

Artavanis-Tsakonas, S., et al., "Notch Signaling: Cell Fate Control and Signal Integration in Development," *Science* 284: 770-776, American Association for the Advancement of Science, United States (1999).

Brennan, K. and Brown, A.M., "Is there a rol for Notch signaling in human breast cancer?" *Breast Cancer Res* 5(2):69-75, BioMed Central Ltd., England (2003).

Dufraine, J., et al., "Notch signaling regulates tumor angiogenesis by diverse mechanisms," *Oncogene* 27(38):5132-5137, Nature Publishing Group, England (2008).

Iso, T., et al., "Notch signaling in vascular development," *Arterioscler. Thromb. Vasc. Biol.* 23(4):543-553, Lippincott Williams & Wilkins, United States (2003).

Jemal, A., et al., "Cancer Statisitics, 2008" *CA Cancer J. Clin.* 58(2):71-96, American Cancer Society, United States (2008).

Joutel, A., et al., "Notch3 mutations in CADASIL, a hereditary adult-onset condition causing stroke and dementia," *Nature* 383(602):707-710, Nature Publishing Group, London, (1996).

Leong, K.G. and Karsan, A., "Recent insights into the role of Notch signaling in tumorigenesis," *Blood* 107:2223-2233, American Scoeity of Hematology, United States (2006).

\* cited by examiner

SEQUENCE LISTING

<160> NUMBER OF SEQ ID NOS: 55

<210> SEQ ID NO 1
<211> LENGTH: 459
<212> TYPE: PRT
<213> ORGANISM: Artificial Sequence
<220> FEATURE:
<223> OTHER INFORMATION: 64M51 Heavy chain

<400> SEQUENCE: 1

```
Met Glu Cys Ser Trp Val Ile Leu Phe Leu Leu Ser Gly Thr Ala Gly
1               5                   10                  15

Val His Cys Gln Val Gln Leu Lys Gln Ser Gly Ala Glu Leu Val Arg
                20                  25                  30

Pro Gly Thr Ser Val Lys Leu Ser Cys Lys Ser Tyr Ile Phe
        35                  40                  45

Thr Ser Tyr Trp Ile His Trp Val Lys Gln Arg Ser Gly Gln Gly Leu
    50                  55                  60

Glu Trp Ile Ala Arg Ile Tyr Pro Gly Ile Gly Ser Thr Tyr Tyr Asn
65                  70                  75                  80

Glu Lys Phe Lys Asp Lys Ala Thr Leu Thr Ala Asp Lys Ser Ser Ser
                85                  90                  95

Thr Ala Tyr Met Gln Leu Ser Ser Leu Lys Ser Glu Asp Ser Ala Val
            100                 105                 110

Tyr Phe Cys Ala Lys Asn Gly Gly Phe Phe Asp Tyr Trp Gly Gln Gly
        115                 120                 125

Thr Thr Leu Thr Val Ser Ser Ala Lys Thr Thr Pro Pro Ser Val Tyr
130                 135                 140

Pro Leu Ala Pro Gly Ser Ala Ala Gln Thr Asn Ser Met Val Thr Leu
145                 150                 155                 160

Gly Cys Leu Val Lys Gly Tyr Phe Pro Glu Pro Val Thr Val Thr Trp
                165                 170                 175

Asn Ser Gly Ser Leu Ser Ser Gly Val His Thr Phe Pro Ala Val Leu
            180                 185                 190

Gln Ser Asp Leu Tyr Thr Leu Ser Ser Ser Val Thr Val Pro Ser Ser
        195                 200                 205

Thr Trp Pro Ser Gln Thr Val Thr Cys Asn Val Ala His Pro Ala Ser
    210                 215                 220

Ser Thr Lys Val Asp Lys Lys Ile Val Pro Arg Asp Cys Gly Cys Lys
225                 230                 235                 240

Pro Cys Ile Cys Thr Val Pro Glu Val Ser Ser Val Phe Ile Phe Pro
                245                 250                 255

Pro Lys Pro Lys Asp Val Leu Thr Ile Thr Leu Thr Pro Lys Val Thr
            260                 265                 270

Cys Val Val Val Asp Ile Ser Lys Asp Asp Pro Glu Val Gln Phe Ser
        275                 280                 285

Trp Phe Val Asp Asp Val Glu Val His Thr Ala Gln Thr Lys Pro Arg
    290                 295                 300

Glu Glu Gln Phe Asn Ser Thr Phe Arg Ser Val Ser Glu Leu Pro Ile
305                 310                 315                 320

Met His Gln Asp Trp Leu Asn Gly Lys Glu Phe Lys Cys Arg Val Asn
                325                 330                 335

Ser Ala Ala Phe Pro Ala Pro Ile Glu Lys Thr Ile Ser Lys Thr Lys
            340                 345                 350

Gly Arg Pro Lys Ala Pro Gln Val Tyr Thr Ile Pro Pro Pro Lys Glu
```

```
                   355                 360                 365
Gln Met Ala Lys Asp Lys Val Ser Leu Thr Cys Met Ile Thr Asp Phe
    370                 375                 380

Phe Pro Glu Asp Ile Thr Val Glu Trp Gln Trp Asn Gly Gln Pro Ala
385                 390                 395                 400

Glu Asn Tyr Lys Asn Thr Gln Pro Ile Met Asp Thr Asp Gly Ser Tyr
                405                 410                 415

Phe Val Tyr Ser Lys Leu Asn Val Gln Lys Ser Asn Trp Glu Ala Gly
            420                 425                 430

Asn Thr Phe Thr Cys Ser Val Leu His Glu Gly Leu His Asn His His
        435                 440                 445

Thr Glu Lys Ser Leu Ser His Ser Pro Gly Lys
    450                 455

<210> SEQ ID NO 2
<211> LENGTH: 1377
<212> TYPE: DNA
<213> ORGANISM: Artificial Sequence
<220> FEATURE:
<223> OTHER INFORMATION: 64M51 Heavy chain

<400> SEQUENCE: 2
atggaatgca gctgggttat cctcttcctc ctgtcaggaa ctgcaggtgt ccactgccag      60
gtccagttga agcagtctgg agctgagctg gtgaggcctg ggacttcagt gaagctgtcc     120
tgcaagactt ctggatacat cttcaccagc tactggattc actgggtaaa acagaggtct     180
ggacagggcc ttgagtggat tgcaaggatt tatcctggaa ttggtagtac ttactacaat     240
gagaagttca aggacaaggc cacactgact gcagacaaat cctccagcac cgcctacatg     300
cagctcagca gcctgaaatc tgaggactct gctgtctatt tctgtgcaaa aaatgggggt     360
ttttttgact actggggcca aggcaccact ctcacagtct cctcagccaa aacgacaccc     420
ccatctgtct atccactggc ccctggatct gctgcccaaa ctaactccat ggtgaccctg     480
ggatgcctgg tcaagggcta tttccctgag ccagtgacag tgacctggaa ctctggatcc     540
ctgtccagcg gtgtgcacac cttcccagct gtcctgcagt ctgacctcta cactctgagc     600
agctcagtga ctgtcccctc agcacctggg cccagccaga ccgtcacctg caacgttgcc     660
cacccggcca gcagcaccaa ggtggacaag aaaattgtgc ccagggattg tggttgtaag     720
ccttgcatat gtacagtccc agaagtatca tctgtcttca tcttcccccc aaagcccaag     780
gatgtgctca ccattactct gactcctaag gtcacgtgtg ttgtggtaga catcagcaag     840
gatgatcccg aggtccagtt cagctggttt gtagatgatg tggaggtgca cacagctcag     900
acaaaacccc gggaggagca gttcaacagc actttccgtt cagtcagtga acttcccatc     960
atgcaccagg actggctcaa tggcaaggag ttcaaatgca gggtcaacag tgcagctttc    1020
cctgccccca tcgagaaaac catctccaaa accaaaggca gaccgaaggc tccacaggtg    1080
tacaccattc cacctcccaa ggagcagatg gccaaggata agtcagtctg acctgcatg     1140
ataacagact tcttccctga agacattact gtggagtggc agtggaatgg cagccagcg     1200
gagaactaca gaacactca gcccatcatg acacagatg gctcttactt cgtctacagc      1260
aagctcaatg tgcagaagag caactgggag gcaggaaata ctttcacctg ctctgtgtta    1320
catgagggcc tgcacaacca ccatactgag aagagcctct cccactctcc tggtaaa       1377

<210> SEQ ID NO 3
<211> LENGTH: 233
```

```
<212> TYPE: PRT
<213> ORGANISM: Artificial Sequence
<220> FEATURE:
<223> OTHER INFORMATION: 64M51 Light chain

<400> SEQUENCE: 3

Met Val Leu Met Leu Leu Leu Trp Val Pro Gly Ser Thr Gly Asp
1               5                   10                  15

Ile Val Leu Thr Gln Ser Pro Ala Ser Leu Ala Val Ser Leu Gly Gln
            20                  25                  30

Arg Ala Thr Ile Ser Cys Arg Ala Ser Glu Ser Val Asp Ser Tyr Gly
        35                  40                  45

Asn Ser Phe Met His Trp Tyr Gln Gln Lys Pro Gly Gln Pro Pro Lys
    50                  55                  60

Leu Leu Ile Tyr Arg Ala Ser Asn Leu Glu Ser Gly Ile Pro Ala Arg
65                  70                  75                  80

Phe Ser Gly Ser Gly Ser Arg Thr Asp Phe Thr Leu Thr Ile Asn Pro
                85                  90                  95

Val Glu Ala Asp Asp Val Ala Thr Tyr Tyr Cys Gln Gln Ser Asn Glu
            100                 105                 110

Asp Pro Trp Thr Phe Gly Gly Gly Thr Lys Leu Glu Ile Lys Arg Ala
        115                 120                 125

Asp Ala Ala Pro Thr Val Ser Ile Phe Pro Pro Ser Ser Glu Gln Leu
    130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr Cys Glu Ala Thr His Lys Thr Ser Thr Ser Pro Ile
    210                 215                 220

Val Lys Ser Phe Asn Arg Asn Glu Cys
225                 230

<210> SEQ ID NO 4
<211> LENGTH: 699
<212> TYPE: DNA
<213> ORGANISM: Artificial Sequence
<220> FEATURE:
<223> OTHER INFORMATION: 64M51 Light chain

<400> SEQUENCE: 4
atggttctca tgttactgct gctatgggtt ccaggttcca caggtgacat tgtgctgacc      60
caatctccag cttctttggc tgtgtctcta ggacagaggg ccaccatatc ctgcagagcc     120
agtgaaagtg ttgatagtta tggcaatagt tttatgcact ggtaccagca gaaaccagga     180
cagccaccca aactcctcat ctatcgtgca tccaacctag aatctgggat ccctgccagg     240
ttcagtggca gtgggtctag gacagacttc accctcacca ttaatcctgt ggaggctgat     300
gatgttgcaa cctattactg tcagcaaagt aatgaggatc cgtggacgtt cggtggaggc     360
accaagctgg aaatcaaacg ggctgatgct gcaccaactg tatccatctt cccaccatcc     420
agtgagcagt taacatctgg aggtgcctca gtcgtgtgct tcttgaacaa cttctacccc     480
aaagacatca atgtcaagtg gaagattgat ggcagtgaac gacaaaatgg cgtcctgaac     540
```

```
agttggactg atcaggacag caaagacagc acctacagca tgagcagcac cctcacgttg    600
accaaggacg agtatgaacg acataacagc tatacctgtg aggccactca caagacatca    660
acttcaccca ttgtcaagag cttcaacagg aatgagtgt                           699
```

<210> SEQ ID NO 5
<211> LENGTH: 116
<212> TYPE: PRT
<213> ORGANISM: Artificial Sequence
<220> FEATURE:
<223> OTHER INFORMATION: 64M51 Heavy chain variable region

<400> SEQUENCE: 5

```
Gln Val Gln Leu Lys Gln Ser Gly Ala Glu Leu Val Arg Pro Gly Thr
1               5                   10                  15

Ser Val Lys Leu Ser Cys Lys Thr Ser Gly Tyr Ile Phe Thr Ser Tyr
            20                  25                  30

Trp Ile His Trp Val Lys Gln Arg Ser Gly Gln Gly Leu Glu Trp Ile
        35                  40                  45

Ala Arg Ile Tyr Pro Gly Ile Gly Ser Thr Tyr Tyr Asn Glu Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Lys Ser Glu Asp Ser Ala Val Tyr Phe Cys
                85                  90                  95

Ala Lys Asn Gly Gly Phe Phe Asp Tyr Trp Gly Gln Gly Thr Thr Leu
            100                 105                 110

Thr Val Ser Ser
        115
```

<210> SEQ ID NO 6
<211> LENGTH: 348
<212> TYPE: DNA
<213> ORGANISM: Artificial Sequence
<220> FEATURE:
<223> OTHER INFORMATION: 64M51 Heavy chain variable region

<400> SEQUENCE: 6

```
caggtccagt tgaagcagtc tggagctgag ctggtgaggc ctgggacttc agtgaagctg     60
tcctgcaaga cttctggata catcttcacc agctactgga ttcactgggt aaaacagagg    120
tctggacagg gccttgagtg gattgcaagg atttatcctg gaattggtag tacttactac    180
aatgagaagt tcaaggacaa ggccacactg actgcagaca aatcctccag caccgcctac    240
atgcagctca gcagcctgaa atctgaggac tctgctgtct atttctgtgc aaaaaatggg    300
ggtttttttg actactgggg ccaaggcacc actctcacag tctcctca                 348
```

<210> SEQ ID NO 7
<211> LENGTH: 111
<212> TYPE: PRT
<213> ORGANISM: Artificial Sequence
<220> FEATURE:
<223> OTHER INFORMATION: 64M51 Light chain variable region

<400> SEQUENCE: 7

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30
```

Gly Asn Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Trp Thr Phe Gly Gly Gly Thr Lys Leu Glu Ile Lys
            100                 105                 110

<210> SEQ ID NO 8
<211> LENGTH: 333
<212> TYPE: DNA
<213> ORGANISM: Artificial Sequence
<220> FEATURE:
<223> OTHER INFORMATION: 64M51 Light chain variable region

<400> SEQUENCE: 8
gacattgtgc tgacccaatc tccagcttct ttggctgtgt ctctaggaca gagggccacc      60
atatcctgca gagccagtga aagtgttgat agttatggca atagttttat gcactggtac     120
cagcagaaac caggacagcc acccaaactc ctcatctatc gtgcatccaa cctagaatct     180
gggatccctg ccaggttcag tggcagtggg tctaggacag acttcaccct caccattaat     240
cctgtggagg ctgatgatgt tgcaacctat tactgtcagc aaagtaatga ggatccgtgg     300
acgttcggtg gaggcaccaa gctggaaatc aaa                                  333

<210> SEQ ID NO 9
<211> LENGTH: 5
<212> TYPE: PRT
<213> ORGANISM: Artificial Sequence
<220> FEATURE:
<223> OTHER INFORMATION: 64M51 Heavy chain CDR1

<400> SEQUENCE: 9

Ser Tyr Trp Ile His
 1               5

<210> SEQ ID NO 10
<211> LENGTH: 17
<212> TYPE: PRT
<213> ORGANISM: Artificial Sequence
<220> FEATURE:
<223> OTHER INFORMATION: 64M51 Heavy chain CDR2

<400> SEQUENCE: 10

Arg Ile Tyr Pro Gly Ile Gly Ser Thr Tyr Tyr Asn Glu Lys Phe Lys
 1               5                  10                  15

Asp

<210> SEQ ID NO 11
<211> LENGTH: 7
<212> TYPE: PRT
<213> ORGANISM: Artificial Sequence
<220> FEATURE:
<223> OTHER INFORMATION: 64M51 Heavy chain CDR3

<400> SEQUENCE: 11

Asn Gly Gly Phe Phe Asp Tyr
 1               5

```
<210> SEQ ID NO 12
<211> LENGTH: 15
<212> TYPE: PRT
<213> ORGANISM: Artificial Sequence
<220> FEATURE:
<223> OTHER INFORMATION: 64M51 Light chain CDR1

<400> SEQUENCE: 12

Arg Ala Ser Glu Ser Val Asp Ser Tyr Gly Asn Ser Phe Met His
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: 64M51 Light chain CDR2

<400> SEQUENCE: 13

Arg Ala Ser Asn Leu Glu Ser
1               5

<210> SEQ ID NO 14
<211> LENGTH: 9
<212> TYPE: PRT
<213> ORGANISM: Artificial Sequence
<220> FEATURE:
<223> OTHER INFORMATION: 64M51 Light chain CDR3

<400> SEQUENCE: 14

Gln Gln Ser Asn Glu Asp Pro Trp Thr
1               5

<210> SEQ ID NO 15
<211> LENGTH: 465
<212> TYPE: PRT
<213> ORGANISM: Artificial Sequence
<220> FEATURE:
<223> OTHER INFORMATION: 64R7 Heavy chain

<400> SEQUENCE: 15

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Ala Met His Trp Val Arg Gln Ala Pro Gly Lys Gly Leu
    50                  55                  60

Glu Trp Val Ala Val Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Lys Tyr Asp Ile Pro Asp Ala Phe Asp Ile
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
```

```
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
            195                 200                 205
Thr Val Pro Ser Ser Asn Phe Gly Thr Gln Thr Tyr Thr Cys Asn Val
            210                 215                 220
Asp His Lys Pro Ser Asn Thr Lys Val Asp Lys Thr Val Glu Arg Lys
225                 230                 235                 240
Cys Cys Val Glu Cys Pro Pro Cys Pro Ala Pro Pro Val Ala Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser His Glu Asp
            275                 280                 285
Pro Glu Val Gln Phe Asn Trp Tyr Val Asp Gly Val Glu Val His Asn
            290                 295                 300
Ala Lys Thr Lys Pro Arg Glu Glu Gln Phe Asn Ser Thr Phe Arg Val
305                 310                 315                 320
Val Ser Val Leu Thr Val Val His Gln Asp Trp Leu Asn Gly Lys Glu
                325                 330                 335
Tyr Lys Cys Lys Val Ser Asn Lys Gly Leu Pro Ala Pro Ile Glu Lys
            340                 345                 350
Thr Ile Ser Lys Thr Lys Gly Gln Pro Arg Glu Pro Gln Val Tyr Thr
            355                 360                 365
Leu Pro Pro Ser Arg Glu Glu Met Thr Lys Asn Gln Val Ser Leu Thr
            370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Met Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
            435                 440                 445
Ala Leu His Asn His Tyr Thr Gln Lys Ser Leu Ser Leu Ser Pro Gly
            450                 455                 460
Lys
465

<210> SEQ ID NO 16
<211> LENGTH: 1395
<212> TYPE: DNA
<213> ORGANISM: Artificial Sequence
<220> FEATURE:
<223> OTHER INFORMATION: 64R7 Heavy chain

<400> SEQUENCE: 16
atgaaacacc tgtggttctt cctcctgctg gtggcagctc ccagatgggt cctgtcccag    60
gtgcaattgg tggagtctgg gggaggcgtg gtccagcctg gaggtccct gagactctcc    120 tgtgcagcct ctggattcac cttcagtagc tatgctatgc actgggtccg ccaggctcca    180
ggcaaggggc tggagtgggt ggcagttata tcatatgatg aagcaataa atactacgca    240 gactccgtga agggccgatt caccatctcc agagacaatt ccaagaacac gctgtatctg    300
```

-continued

```
caaatgaaca gcctgagagc tgaggacacg gctgtgtatt actgtgcgag agataaatac      360
gatattccag atgctttga tatctggggc caaggaaccc tggtcaccgt cagctcagcc      420
agcacaaagg gccctagcgt cttccctctg gctccctgca gcaggagcac cagcgagagc      480
acagccgccc tgggctgcct ggtcaaggac tacttccccg aaccggtgac ggtgtcgtgg      540
aactcaggcg ctctgaccag cggcgtgcac accttcccag ctgtcctaca gtcctcagga      600
ctctactccc tcagcagcgt ggtgaccgtg ccctccagca acttcggcac ccagacctac      660
acctgcaacg tagatcacaa gcccagcaac accaaggtgg acaagacagt tgagcgcaaa      720
tgttgtgtcg agtgcccacc gtgcccagca ccacctgtgg caggaccgtc agtcttcctc      780
ttcccccaa aacccaagga caccctcatg atctcccgga cccctgaggt cacgtgcgtg      840
gtggtggacg tgagccacga agaccccgag gtccagttca actggtacgt ggacggcgtg      900
gaggtgcata atgccaagac aaagccacgg gaggagcagt tcaacagcac gttccgtgtg      960
gtcagcgtcc tcaccgttgt gcaccaggac tggctgaacg gcaaggagta caagtgcaag     1020
gtctccaaca aaggcctccc agcccccatc gagaaaacca tctccaaaac caagggcag     1080
ccccgagaac cacaggtgta caccctgccc ccatcccggg aggagatgac caagaaccag     1140
gtcagcctga cctgcctggt caaaggcttc taccccagcg acatcgccgt ggagtgggag     1200
agcaatgggc agccggagaa caactacaag accacacctc ccatgctgga ctccgacggc     1260
tccttcttcc tctacagcaa gctcaccgtg gacaagagca ggtggcagca ggggaacgtc     1320
ttctcatgct ccgtgatgca tgaggctctg cacaaccact acacgcagaa gagcctctcc     1380
ctgtctccgg gtaaa                                                      1395
```

<210> SEQ ID NO 17
<211> LENGTH: 234
<212> TYPE: PRT
<213> ORGANISM: Artificial Sequence
<220> FEATURE:
<223> OTHER INFORMATION: 64R7 Light chain

<400> SEQUENCE: 17

```
Met Val Leu Gln Thr Gln Val Phe Ile Ser Leu Leu Trp Ile Ser
1               5                   10                  15

Gly Ala Tyr Gly Asp Ile Arg Met Thr Gln Ser Pro Ser Ser Leu Ser
                20                  25                  30

Ala Ser Val Gly Asp Arg Val Thr Ile Thr Cys Arg Ala Ser Gln Gly
            35                  40                  45

Ile Ser Asn Asp Leu Ala Trp Tyr Gln Gln Lys Pro Gly Lys Val Pro
        50                  55                  60

Arg Leu Leu Ile Tyr Ala Thr Ser Thr Leu Gln Ser Gly Val Pro Ser
65                  70                  75                  80

Arg Phe Ser Gly Ser Gly Ser Ala Thr Asp Phe Thr Leu Thr Ile Ser
                85                  90                  95

Ser Leu Gln Pro Glu Asp Val Ala Thr Tyr Tyr Cys Gln Gln Ser Tyr
            100                 105                 110

Asn Ala Pro Ile Thr Phe Gly Gln Gly Thr Arg Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
```

-continued

```
                165                 170                 175
Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 18
<211> LENGTH: 702
<212> TYPE: DNA
<213> ORGANISM: Artificial Sequence
<220> FEATURE:
<223> OTHER INFORMATION: 64R7 Light chain

<400> SEQUENCE: 18

```
atggtgttgc agacccaggt cttcatttct ctgttgctct ggatctctgg tgcctacggg      60
gatatccgga tgacccagtc tccatcctcc ctgtctgcat ctgttggaga cagagtcacc     120
atcacttgcc gggcgagtca gggcattagt aatgatttag cctggtatca gcagaagcca     180
gggaaagttc ctaggctcct gatctatgct acatccactt tgcaatctgg ggtcccatct     240
cgtttcagtg gcagtggatc tgcgacagat ttcactctca ccatcagcag cctgcagcct     300
gaagatgttg caacttatta ctgtcaacag agttacaatg ccccgatcac cttcggccaa     360
gggacacgac tggagattaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga aaacacaaa gtctacgcct gcgaagtcac ccatcagggc     660
ctgagctcgc ccgtcacaaa gagcttcaac aggggagagt gt                       702
```

<210> SEQ ID NO 19
<211> LENGTH: 120
<212> TYPE: PRT
<213> ORGANISM: Artificial Sequence
<220> FEATURE:
<223> OTHER INFORMATION: 64R7 Heavy chain variable region

<400> SEQUENCE: 19

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Tyr Asp Ile Pro Asp Ala Phe Asp Ile Trp Gly Gln
            100                 105                 110
```

```
Gly Thr Leu Val Thr Val Ser Ser
        115                 120
```

<210> SEQ ID NO 20
<211> LENGTH: 360
<212> TYPE: DNA
<213> ORGANISM: Artificial Sequence
<220> FEATURE:
<223> OTHER INFORMATION: 64R7 Heavy chain variable region

<400> SEQUENCE: 20

```
caggtgcaat tggtggagtc tgggggaggc gtggtccagc ctggggaggtc cctgagactc    60
tcctgtgcag cctctggatt caccttcagt agctatgcta tgcactgggt ccgccaggct   120
ccaggcaagg ggctggagtg ggtggcagtt atatcatatg atggaagcaa taaatactac   180
gcagactccg tgaagggccg attcaccatc tccagagaca attccaagaa cacgctgtat   240
ctgcaaatga acagcctgag agctgaggac acggctgtgt attactgtgc gagagataaa   300
tacgatattc cagatgcttt tgatatctgg ggccaaggaa ccctggtcac cgtcagctca   360
```

<210> SEQ ID NO 21
<211> LENGTH: 107
<212> TYPE: PRT
<213> ORGANISM: Artificial Sequence
<220> FEATURE:
<223> OTHER INFORMATION: 64R7 Light chain variable region

<400> SEQUENCE: 21

```
Asp Ile Arg Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Asn Asp
            20                  25                  30
Leu Ala Trp Tyr Gln Gln Lys Pro Gly Lys Val Pro Arg Leu Leu Ile
        35                  40                  45
Tyr Ala Thr Ser Thr Leu Gln Ser Gly Val Pro Ser Arg Phe Ser Gly
    50                  55                  60
Ser Gly Ser Ala Thr Asp Phe Thr Leu Thr Ile Ser Ser Leu Gln Pro
65                  70                  75                  80
Glu Asp Val Ala Thr Tyr Tyr Cys Gln Gln Ser Tyr Asn Ala Pro Ile
                85                  90                  95
Thr Phe Gly Gln Gly Thr Arg Leu Glu Ile Lys
            100                 105
```

<210> SEQ ID NO 22
<211> LENGTH: 321
<212> TYPE: DNA
<213> ORGANISM: Artificial Sequence
<220> FEATURE:
<223> OTHER INFORMATION: 64R7 Light chain variable region

<400> SEQUENCE: 22

```
gatatccgga tgacccagtc tccatcctcc ctgtctgcat ctgttggaga cagagtcacc    60
atcacttgcc gggcgagtca gggcattagt aatgatttag cctggtatca gcagaagcca   120
gggaaagttc ctaggctcct gatctatgct acatccactt tgcaatctgg ggtcccatct   180
cgtttcagtg gcagtggatc tgcgacagat ttcactctca ccatcagcag cctgcagcct   240
gaagatgttg caacttatta ctgtcaacag agttacaatg ccccgatcac cttcggccaa   300
gggacacgac tggagattaa a                                             321
```

```
<210> SEQ ID NO 23
<211> LENGTH: 5
<212> TYPE: PRT
<213> ORGANISM: Artificial Sequence
<220> FEATURE:
<223> OTHER INFORMATION: 64R7 Heavy chain CDR1

<400> SEQUENCE: 23

Ser Tyr Ala Met His
1               5

<210> SEQ ID NO 24
<211> LENGTH: 17
<212> TYPE: PRT
<213> ORGANISM: Artificial Sequence
<220> FEATURE:
<223> OTHER INFORMATION: 64R7 Heavy chain CDR2

<400> SEQUENCE: 24

Val Ile Ser Tyr Asp Gly Ser Asn Lys Tyr Tyr Ala Asp Ser Val Lys
1               5                   10                  15

Gly

<210> SEQ ID NO 25
<211> LENGTH: 11
<212> TYPE: PRT
<213> ORGANISM: Artificial Sequence
<220> FEATURE:
<223> OTHER INFORMATION: 64R7 Heavy chain CDR3

<400> SEQUENCE: 25

Asp Lys Tyr Asp Ile Pro Asp Ala Phe Asp Ile
1               5                   10

<210> SEQ ID NO 26
<211> LENGTH: 11
<212> TYPE: PRT
<213> ORGANISM: Artificial Sequence
<220> FEATURE:
<223> OTHER INFORMATION: 64R7 Light chain CDR1

<400> SEQUENCE: 26

Arg Ala Ser Gln Gly Ile Ser Asn Asp Leu Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: 64R7 Light chain CDR2

<400> SEQUENCE: 27

Ala Thr Ser Thr Leu Gln Ser
1               5

<210> SEQ ID NO 28
<211> LENGTH: 8
<212> TYPE: PRT
<213> ORGANISM: Artificial Sequence
<220> FEATURE:
<223> OTHER INFORMATION: 64R7 Light chain CDR3

<400> SEQUENCE: 28

Gln Gln Ser Tyr Asn Ala Pro Ile
1               5
```

<210> SEQ ID NO 29
<211> LENGTH: 465
<212> TYPE: PRT
<213> ORGANISM: Artificial Sequence
<220> FEATURE:
<223> OTHER INFORMATION: 64R1B Heavy chain

<400> SEQUENCE: 29

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gly Thr Leu Ser Leu Thr Cys Thr Val Ser Gly Asp Ser Ile
        35                  40                  45

Ser Ser Ser Asn Trp Trp Ser Trp Val Arg Gln Pro Pro Gly Gln Gly
    50                  55                  60

Leu Glu Trp Ile Gly Glu Ile Phe His Gly Glu Asn Thr Asn Tyr Asn
65                  70                  75                  80

Pro Ser Leu Lys Ser Arg Val Thr Ile Ser Val Asp Lys Ser Lys Asn
                85                  90                  95

Gln Ile Ser Leu Asn Leu Thr Ser Ala Thr Ala Ala Asp Thr Ala Val
            100                 105                 110

Tyr Tyr Cys Ala Arg Asn Pro Gly Ile Gly Ala Ala Lys Phe Asp Ser
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365
```

| | | | | | | | | | | |
|---|---|---|---|---|---|---|---|---|---|---|
| Leu | Pro | Pro | Ser | Arg | Glu | Glu | Met | Thr | Lys | Asn | Gln | Val | Ser | Leu | Thr |
| 370 | | | | 375 | | | | | 380 | | | | | | |
| Cys | Leu | Val | Lys | Gly | Phe | Tyr | Pro | Ser | Asp | Ile | Ala | Val | Glu | Trp | Glu |
| 385 | | | | 390 | | | | | 395 | | | | | | 400 |
| Ser | Asn | Gly | Gln | Pro | Glu | Asn | Asn | Tyr | Lys | Thr | Thr | Pro | Pro | Met | Leu |
| | | | 405 | | | | | 410 | | | | | 415 | | |
| Asp | Ser | Asp | Gly | Ser | Phe | Phe | Leu | Tyr | Ser | Lys | Leu | Thr | Val | Asp | Lys |
| | | | 420 | | | | | 425 | | | | 430 | | | |
| Ser | Arg | Trp | Gln | Gln | Gly | Asn | Val | Phe | Ser | Cys | Ser | Val | Met | His | Glu |
| | | | 435 | | | | 440 | | | | 445 | | | | |
| Ala | Leu | His | Asn | His | Tyr | Thr | Gln | Lys | Ser | Leu | Ser | Leu | Ser | Pro | Gly |
| | 450 | | | | | 455 | | | | 460 | | | | | |
| Lys | | | | | | | | | | | | | | | |
| 465 | | | | | | | | | | | | | | | |

<210> SEQ ID NO 30
<211> LENGTH: 1395
<212> TYPE: DNA
<213> ORGANISM: Artificial Sequence
<220> FEATURE:
<223> OTHER INFORMATION: 64R1B Heavy chain

<400> SEQUENCE: 30

```
atgaaacacc tgtggttctt cctcctgctg gtggcagctc ccagatgggt cctgtcccag    60
gtgcaattgc aggagtcggg cccaggactg gtgaagcctt cggggaccct gtccctcacc   120
tgcactgtct ctggtgactc catcagcagt tctaactggt ggagttgggt ccgccagccc   180
ccaggtcagg ggctagagtg gattggagaa atctttcatg gggagaacac caactacaat   240
ccgtccctca gagtcgagt caccatatca gtggacaagt ccaaaaatca gatctccctg   300
aacctgacct ctgcgaccgc cgcggacacg gccgtatatt attgtgcgag aaacccgggt   360
attggagcag cgaaatttga ctcctggggc caaggaaccc tggtcaccgt cagctcagcc   420
agcacaaagg gcccagcgt cttccctctg gctccctgca gcaggagcac cagcgagagc   480
acagccgccc tgggctgcct ggtcaaggac tacttccccg aaccggtgac ggtgtcgtgg   540
aactcaggcg ctctgaccag cggcgtgcac accttcccag ctgtcctaca gtcctcagga   600
ctctactccc tcagcagcgt ggtgaccgtg ccctccagca acttcggcac ccagacctac   660
acctgcaacg tagatcacaa gcccagcaac accaaggtgg acaagacagt tgagcgcaaa   720
tgttgtgtcg agtgcccacc gtgcccagca ccacctgtgg caggaccgtc agtcttcctc   780
ttccccccaa aacccaagga cacctcatg atctcccgga cccctgaggt cacgtgcgtg   840
gtggtggacg tgagccacga agaccccgag gtccagttca actggtacgt ggacggcgtg   900
gaggtgcata tgccaagac aaagccacgg gaggagcagt tcaacagcac gttccgtgtg   960
gtcagcgtcc tcaccgttgt gcaccaggac tggctgaacg gcaaggagta caagtgcaag  1020
gtctccaaca aaggcctccc agcccccatc gagaaaacca tctccaaaac caagggcag  1080
ccccgagaac acaggtgta caccctgccc ccatcccggg aggagatgac caagaaccag  1140
gtcagcctga cctgcctggt caaaggcttc taccccagcg acatcgccgt ggagtgggag  1200
agcaatgggc agccggagaa caactacaag accacacctc ccatgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctccgg gtaaa                                                   1395
```

<210> SEQ ID NO 31
<211> LENGTH: 239
<212> TYPE: PRT
<213> ORGANISM: Artificial Sequence
<220> FEATURE:
<223> OTHER INFORMATION: 64R1B Light chain

<400> SEQUENCE: 31

```
Met Val Leu Gln Thr Gln Val Phe Ile Ser Leu Leu Trp Ile Ser
1               5                   10                  15

Gly Ala Tyr Gly Asp Ile Val Met Thr Gln Thr Pro Leu Ser Leu Ser
                20                  25                  30

Val Thr Pro Gly Gln Pro Ala Ser Ile Ser Cys Lys Ser Gln Ser
            35                  40                  45

Leu Leu His Ser Asp Gly Lys Thr Tyr Leu Tyr Trp Tyr Leu Gln Lys
        50                  55                  60

Pro Gly Gln Pro Gln Leu Leu Ile Tyr Glu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln His Ile Asp Phe Pro Phe Thr Phe Gly Gln Gly Thr Lys
        115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 32
<211> LENGTH: 717
<212> TYPE: DNA
<213> ORGANISM: Artificial Sequence
<220> FEATURE:
<223> OTHER INFORMATION: 64R1B Light chain

<400> SEQUENCE: 32

```
atggtgttgc agacccaggt cttcatttct ctgttgctct ggatctctgg tgcctacggg      60
gatatcgtga tgacccagac tccactctct ctgtccgtca cccctggaca gccggcctcc     120
atctcctgca gtctagtca gagcctccta catagtgatg gaaagaccta tttgtattgg     180
tatctgcaga agccaggcca gcctccacag ctcctgatct atgaagtttc caaccgcttc     240
tctggagtgc agataggtt cagtggcagc gggtcaggga cagatttcac actgaaaatc     300
agccgggtgg aggctgagga tgttggagtt tattactgca tgcaacatat agactttcct     360
ttcacttttg gccaggggac caagctggag atcaaacgta cggtggctgc accatctgtc     420
```

```
ttcatcttcc cgccatctga tgagcagttg aaatctggaa ctgcctctgt tgtgtgcctg      480
ctgaataact tctatcccag agaggccaaa gtacagtgga aggtggataa cgccctccaa      540
tcgggtaact cccaggagag tgtcacagag caggacagca aggacagcac ctacagcctc      600
agcagcaccc tgacgctgag caaagcagac tacgagaaac acaaagtcta cgcctgcgaa      660
gtcacccatc agggcctgag ctcgcccgtc acaaagagct tcaacagggg agagtgt        717
```

<210> SEQ ID NO 33
<211> LENGTH: 120
<212> TYPE: PRT
<213> ORGANISM: Artificial Sequence
<220> FEATURE:
<223> OTHER INFORMATION: 64R1B Heavy chain variable region

<400> SEQUENCE: 33

```
Gln Val Gln Leu Gln Glu Ser Gly Pro Gly Leu Val Lys Pro Ser Gly
1               5                   10                  15

Thr Leu Ser Leu Thr Cys Thr Val Ser Gly Asp Ser Ile Ser Ser Ser
            20                  25                  30

Asn Trp Trp Ser Trp Val Arg Gln Pro Pro Gly Gln Gly Leu Glu Trp
        35                  40                  45

Ile Gly Glu Ile Phe His Gly Glu Asn Thr Asn Tyr Asn Pro Ser Leu
    50                  55                  60

Lys Ser Arg Val Thr Ile Ser Val Asp Lys Ser Lys Asn Gln Ile Ser
65                  70                  75                  80

Leu Asn Leu Thr Ser Ala Thr Ala Ala Asp Thr Ala Val Tyr Tyr Cys
                85                  90                  95

Ala Arg Asn Pro Gly Ile Gly Ala Ala Lys Phe Asp Ser Trp Gly Gln
            100                 105                 110

Gly Thr Leu Val Thr Val Ser Ser
        115                 120
```

<210> SEQ ID NO 34
<211> LENGTH: 360
<212> TYPE: DNA
<213> ORGANISM: Artificial Sequence
<220> FEATURE:
<223> OTHER INFORMATION: 64R1B Heavy chain variable region

<400> SEQUENCE: 34

```
caggtgcaat tgcaggagtc gggcccagga ctggtgaagc cttcggggac cctgtccctc       60
acctgcactg tctctggtga ctccatcagc agttctaact ggtggagttg gtccgccag      120 cccccaggtc aggggctaga gtggattgga gaaatctttc atggggagaa caccaactac      180
aatccgtccc tcaagagtcg agtcaccata tcagtggaca gtccaaaaa tcagatctcc      240 ctgaacctga cctctgcgac cgccgcggac acggccgtat attattgtgc gagaaacccg      300
ggtattggag cagcgaaatt tgactcctgg ggccaaggaa ccctggtcac cgtcagctca      360
```

<210> SEQ ID NO 35
<211> LENGTH: 112
<212> TYPE: PRT
<213> ORGANISM: Artificial Sequence
<220> FEATURE:
<223> OTHER INFORMATION: 64R1B Light chain variable region

<400> SEQUENCE: 35

```
Asp Ile Val Met Thr Gln Thr Pro Leu Ser Leu Ser Val Thr Pro Gly
1               5                   10                  15
```

```
Gln Pro Ala Ser Ile Ser Cys Lys Ser Ser Gln Ser Leu Leu His Ser
                20                  25                  30

Asp Gly Lys Thr Tyr Leu Tyr Trp Tyr Leu Gln Lys Pro Gly Gln Pro
            35                  40                  45

Pro Gln Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Ile Asp Phe Pro Phe Thr Phe Gly Gln Gly Thr Lys Leu Glu Ile Lys
            100                 105                 110
```

<210> SEQ ID NO 36
<211> LENGTH: 336
<212> TYPE: DNA
<213> ORGANISM: Artificial Sequence
<220> FEATURE:
<223> OTHER INFORMATION: 64R1B Light chain variable region

<400> SEQUENCE: 36

```
gatatcgtga tgacccagac tccactctct ctgtccgtca cccctggaca gccggcctcc      60
atctcctgca gtctagtca gagcctccta catagtgatg gaaagaccta tttgtattgg     120
tatctgcaga agccaggcca gcctccacag ctcctgatct atgaagtttc caaccgcttc     180
tctggagtgc cagataggtt cagtggcagc gggtcaggga cagatttcac actgaaaatc     240
agccgggtgg aggctgagga tgttggagtt tattactgca tgcaacatat agactttcct     300
ttcacttttg gccaggggac caagctggag atcaaa                                336
```

<210> SEQ ID NO 37
<211> LENGTH: 6
<212> TYPE: PRT
<213> ORGANISM: Artificial Sequence
<220> FEATURE:
<223> OTHER INFORMATION: 64R1B Heavy chain CDR1

<400> SEQUENCE: 37

```
Ser Ser Asn Trp Trp Ser
1               5
```

<210> SEQ ID NO 38
<211> LENGTH: 16
<212> TYPE: PRT
<213> ORGANISM: Artificial Sequence
<220> FEATURE:
<223> OTHER INFORMATION: 64R1B Heavy chain CDR2

<400> SEQUENCE: 38

```
Glu Ile Phe His Gly Glu Asn Thr Asn Tyr Asn Pro Ser Leu Lys Ser
1               5                   10                  15
```

<210> SEQ ID NO 39
<211> LENGTH: 11
<212> TYPE: PRT
<213> ORGANISM: Artificial Sequence
<220> FEATURE:
<223> OTHER INFORMATION: 64R1B Heavy chain CDR3

<400> SEQUENCE: 39

```
Asn Pro Gly Ile Gly Ala Ala Lys Phe Asp Ser
1               5                   10
```

```
<210> SEQ ID NO 40
<211> LENGTH: 16
<212> TYPE: PRT
<213> ORGANISM: Artificial Sequence
<220> FEATURE:
<223> OTHER INFORMATION: 64R1B Light chain CDR1

<400> SEQUENCE: 40

Lys Ser Ser Gln Ser Leu Leu His Ser Asp Gly Lys Thr Tyr Leu Tyr
1               5                   10                  15

<210> SEQ ID NO 41
<211> LENGTH: 7
<212> TYPE: PRT
<213> ORGANISM: Artificial Sequence
<220> FEATURE:
<223> OTHER INFORMATION: 64R1B Light chain CDR2

<400> SEQUENCE: 41

Glu Val Ser Asn Arg Phe Ser
1               5

<210> SEQ ID NO 42
<211> LENGTH: 7
<212> TYPE: PRT
<213> ORGANISM: Artificial Sequence
<220> FEATURE:
<223> OTHER INFORMATION: 64R1B Light chain CDR3

<400> SEQUENCE: 42

Met Gln His Ile Asp Phe Pro
1               5

<210> SEQ ID NO 43
<211> LENGTH: 1218
<212> TYPE: PRT
<213> ORGANISM: Homo sapiens

<400> SEQUENCE: 43

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
                20                  25                  30

Gly Gln Phe Glu Leu Glu Ile Leu Ser Met Gln Asn Val Asn Gly Glu
            35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175
```

```
Ala His Phe Glu Tyr Gln Ile Arg Val Thr Cys Asp Asp Tyr Tyr
            180                 185                 190
Gly Phe Gly Cys Asn Lys Phe Cys Arg Pro Arg Asp Phe Phe Gly
            195                 200                 205
His Tyr Ala Cys Asp Gln Asn Gly Asn Lys Thr Cys Met Glu Gly Trp
    210                 215                 220
Met Gly Pro Glu Cys Asn Arg Ala Ile Cys Arg Gln Gly Cys Ser Pro
225                 230                 235                 240
Lys His Gly Ser Cys Lys Leu Pro Gly Asp Cys Arg Cys Gln Tyr Gly
                245                 250                 255
Trp Gln Gly Leu Tyr Cys Asp Lys Cys Ile Pro His Pro Gly Cys Val
            260                 265                 270
His Gly Ile Cys Asn Glu Pro Trp Gln Cys Leu Cys Glu Thr Asn Trp
            275                 280                 285
Gly Gly Gln Leu Cys Asp Lys Asp Leu Asn Tyr Cys Gly Thr His Gln
            290                 295                 300
Pro Cys Leu Asn Gly Gly Thr Cys Ser Asn Thr Gly Pro Asp Lys Tyr
305                 310                 315                 320
Gln Cys Ser Cys Pro Glu Gly Tyr Ser Gly Pro Asn Cys Glu Ile Ala
                325                 330                 335
Glu His Ala Cys Leu Ser Asp Pro Cys His Asn Arg Gly Ser Cys Lys
            340                 345                 350
Glu Thr Ser Leu Gly Phe Glu Cys Glu Cys Ser Pro Gly Trp Thr Gly
            355                 360                 365
Pro Thr Cys Ser Thr Asn Ile Asp Asp Cys Ser Pro Asn Asn Cys Ser
370                 375                 380
His Gly Gly Thr Cys Gln Asp Leu Val Asn Gly Phe Lys Cys Val Cys
385                 390                 395                 400
Pro Pro Gln Trp Thr Gly Lys Thr Cys Gln Leu Asp Ala Asn Glu Cys
            405                 410                 415
Glu Ala Lys Pro Cys Val Asn Ala Lys Ser Cys Lys Asn Leu Ile Ala
            420                 425                 430
Ser Tyr Tyr Cys Asp Cys Leu Pro Gly Trp Met Gly Asn Cys Asp
            435                 440                 445
Ile Asn Ile Asn Asp Cys Leu Gly Gln Cys Gln Asn Asp Ala Ser Cys
    450                 455                 460
Arg Asp Leu Val Asn Gly Tyr Arg Cys Ile Cys Pro Pro Gly Tyr Ala
465                 470                 475                 480
Gly Asp His Cys Glu Arg Asp Ile Asp Glu Cys Ala Ser Asn Pro Cys
                485                 490                 495
Leu Asn Gly Gly His Cys Gln Asn Glu Ile Asn Arg Phe Gln Cys Leu
            500                 505                 510
Cys Pro Thr Gly Phe Ser Gly Asn Leu Cys Gln Leu Asp Ile Asp Tyr
            515                 520                 525
Cys Glu Pro Asn Pro Cys Gln Asn Gly Ala Gln Cys Tyr Asn Arg Ala
            530                 535                 540
Ser Asp Tyr Phe Cys Lys Cys Pro Glu Asp Tyr Glu Gly Lys Asn Cys
545                 550                 555                 560
Ser His Leu Lys Asp His Cys Arg Thr Thr Pro Cys Glu Val Ile Asp
                565                 570                 575
Ser Cys Thr Val Ala Met Ala Ser Asn Asp Thr Pro Glu Gly Val Arg
            580                 585                 590
```

-continued

```
Tyr Ile Ser Ser Asn Val Cys Gly Pro His Gly Lys Cys Lys Ser Gln
            595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
            675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
            755                 760                 765

Val Cys Lys Glu Gly Trp Glu Gly Pro Ile Cys Ala Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
            835                 840                 845

Gly His Ser Gly Ala Lys Cys Gln Glu Val Ser Gly Arg Pro Cys Ile
850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
            915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser  Pro Ser Ala
            995                 1000                1005

Asn Asn  Glu Ile His Val Ala  Ile Ser Ala Glu Asp  Ile Arg Asp
```

```
                1010                1015                1020

Asp Gly Asn Pro Ile Lys Glu Ile Thr Asp Lys Ile Ile Asp Leu
            1025                1030                1035

Val Ser Lys Arg Asp Gly Asn Ser Ser Leu Ile Ala Ala Val Ala
        1040                1045                1050

Glu Val Arg Val Gln Arg Arg Pro Leu Lys Asn Arg Thr Asp Phe
        1055                1060                1065

Leu Val Pro Leu Leu Ser Ser Val Leu Thr Val Ala Trp Ile Cys
        1070                1075                1080

Cys Leu Val Thr Ala Phe Tyr Trp Cys Leu Arg Lys Arg Arg Lys
        1085                1090                1095

Pro Gly Ser His Thr His Ser Ala Ser Glu Asp Asn Thr Thr Asn
        1100                1105                1110

Asn Val Arg Glu Gln Leu Asn Gln Ile Lys Asn Pro Ile Glu Lys
        1115                1120                1125

His Gly Ala Asn Thr Val Pro Ile Lys Asp Tyr Glu Asn Lys Asn
        1130                1135                1140

Ser Lys Met Ser Lys Ile Arg Thr His Asn Ser Glu Val Glu Glu
        1145                1150                1155

Asp Asp Met Asp Lys His Gln Gln Lys Ala Arg Phe Ala Lys Gln
        1160                1165                1170

Pro Ala Tyr Thr Leu Val Asp Arg Glu Glu Lys Pro Pro Asn Gly
        1175                1180                1185

Thr Pro Thr Lys His Pro Asn Trp Thr Asn Lys Gln Asp Asn Arg
        1190                1195                1200

Asp Leu Glu Ser Ala Gln Ser Leu Asn Arg Met Glu Tyr Ile Val
        1205                1210                1215

<210> SEQ ID NO 44
<211> LENGTH: 1238
<212> TYPE: PRT
<213> ORGANISM: Homo sapiens

<400> SEQUENCE: 44

Met Arg Ala Gln Gly Arg Gly Arg Leu Pro Arg Leu Leu Leu Leu
1               5                   10                  15

Leu Ala Leu Trp Val Gln Ala Ala Arg Pro Met Gly Tyr Phe Glu Leu
            20                  25                  30

Gln Leu Ser Ala Leu Arg Asn Val Asn Gly Glu Leu Leu Ser Gly Ala
        35                  40                  45

Cys Cys Asp Gly Asp Gly Arg Thr Thr Arg Ala Gly Cys Gly His
    50                  55                  60

Asp Glu Cys Asp Thr Tyr Val Arg Val Cys Leu Lys Glu Tyr Gln Ala
65                  70                  75                  80

Lys Val Thr Pro Thr Gly Pro Cys Ser Tyr Gly His Gly Ala Thr Pro
                85                  90                  95

Val Leu Gly Gly Asn Ser Phe Tyr Leu Pro Pro Ala Gly Ala Ala Gly
            100                 105                 110

Asp Arg Ala Arg Ala Arg Ala Arg Ala Gly Gly Asp Gln Asp Pro Gly
        115                 120                 125

Leu Val Val Ile Pro Phe Gln Phe Ala Trp Pro Arg Ser Phe Thr Leu
    130                 135                 140

Ile Val Glu Ala Trp Asp Trp Asp Asn Asp Thr Thr Pro Asn Glu Glu
145                 150                 155                 160
```

-continued

```
Leu Leu Ile Glu Arg Val Ser His Ala Gly Met Ile Asn Pro Glu Asp
            165                 170                 175
Arg Trp Lys Ser Leu His Phe Ser Gly His Val Ala His Leu Glu Leu
        180                 185                 190
Gln Ile Arg Val Arg Cys Asp Glu Asn Tyr Tyr Ser Ala Thr Cys Asn
    195                 200                 205
Lys Phe Cys Arg Pro Arg Asn Asp Phe Phe Gly His Tyr Thr Cys Asp
210                 215                 220
Gln Tyr Gly Asn Lys Ala Cys Met Asp Gly Trp Met Gly Lys Glu Cys
225                 230                 235                 240
Lys Glu Ala Val Cys Lys Gln Gly Cys Asn Leu Leu His Gly Gly Cys
                245                 250                 255
Thr Val Pro Gly Glu Cys Arg Cys Ser Tyr Gly Trp Gln Gly Arg Phe
            260                 265                 270
Cys Asp Glu Cys Val Pro Tyr Pro Gly Cys Val His Gly Ser Cys Val
        275                 280                 285
Glu Pro Trp Gln Cys Asn Cys Glu Thr Asn Trp Gly Gly Leu Leu Cys
    290                 295                 300
Asp Lys Asp Leu Asn Tyr Cys Gly Ser His His Pro Cys Thr Asn Gly
305                 310                 315                 320
Gly Thr Cys Ile Asn Ala Glu Pro Asp Gln Tyr Arg Cys Thr Cys Pro
                325                 330                 335
Asp Gly Tyr Ser Gly Arg Asn Cys Glu Lys Ala Glu His Ala Cys Thr
            340                 345                 350
Ser Asn Pro Cys Ala Asn Gly Gly Ser Cys His Glu Val Pro Ser Gly
        355                 360                 365
Phe Glu Cys His Cys Pro Ser Gly Trp Ser Gly Pro Thr Cys Ala Leu
    370                 375                 380
Asp Ile Asp Glu Cys Ala Ser Asn Pro Cys Ala Ala Gly Gly Thr Cys
385                 390                 395                 400
Val Asp Gln Val Asp Gly Phe Glu Cys Ile Cys Pro Glu Gln Trp Val
                405                 410                 415
Gly Ala Thr Cys Gln Leu Asp Ala Asn Glu Cys Glu Gly Lys Pro Cys
            420                 425                 430
Leu Asn Ala Phe Ser Cys Lys Asn Leu Ile Gly Gly Tyr Tyr Cys Asp
        435                 440                 445
Cys Ile Pro Gly Trp Lys Gly Ile Asn Cys His Ile Asn Val Asn Asp
    450                 455                 460
Cys Arg Gly Gln Cys Gln His Gly Gly Thr Cys Lys Asp Leu Val Asn
465                 470                 475                 480
Gly Tyr Gln Cys Val Cys Pro Arg Gly Phe Gly Gly Arg His Cys Glu
                485                 490                 495
Leu Glu Arg Asp Lys Cys Ala Ser Ser Pro Cys His Ser Gly Gly Leu
            500                 505                 510
Cys Glu Asp Leu Ala Asp Gly Phe His Cys His Cys Pro Gln Gly Phe
        515                 520                 525
Ser Gly Pro Leu Cys Glu Val Asp Val Asp Leu Cys Glu Pro Ser Pro
    530                 535                 540
Cys Arg Asn Gly Ala Arg Cys Tyr Asn Leu Glu Gly Asp Tyr Tyr Cys
545                 550                 555                 560
Ala Cys Pro Asp Asp Phe Gly Gly Lys Asn Cys Ser Val Pro Arg Glu
                565                 570                 575
Pro Cys Pro Gly Gly Ala Cys Arg Val Ile Asp Gly Cys Gly Ser Asp
```

```
                580               585                590
Ala Gly Pro Gly Met Pro Gly Thr Ala Ala Ser Gly Val Cys Gly Pro
            595                 600             605

His Gly Arg Cys Val Ser Gln Pro Gly Gly Asn Phe Ser Cys Ile Cys
            610                 615             620

Asp Ser Gly Phe Thr Gly Thr Tyr Cys His Glu Asn Ile Asp Asp Cys
625                 630                 635                 640

Leu Gly Gln Pro Cys Arg Asn Gly Gly Thr Cys Ile Asp Glu Val Asp
                645                 650                 655

Ala Phe Arg Cys Phe Cys Pro Ser Gly Trp Glu Gly Glu Leu Cys Asp
                660                 665                 670

Thr Asn Pro Asn Asp Cys Leu Pro Asp Pro Cys His Ser Arg Gly Arg
            675                 680                 685

Cys Tyr Asp Leu Val Asn Asp Phe Tyr Cys Ala Cys Asp Asp Gly Trp
            690                 695                 700

Lys Gly Lys Thr Cys His Ser Arg Glu Phe Gln Cys Asp Ala Tyr Thr
705                 710                 715                 720

Cys Ser Asn Gly Gly Thr Cys Tyr Asp Ser Gly Asp Thr Phe Arg Cys
                725                 730                 735

Ala Cys Pro Pro Gly Trp Lys Gly Ser Thr Cys Ala Val Ala Lys Asn
            740                 745                 750

Ser Ser Cys Leu Pro Asn Pro Cys Val Asn Gly Gly Thr Cys Val Gly
            755                 760                 765

Ser Gly Ala Ser Phe Ser Cys Ile Cys Arg Asp Gly Trp Glu Gly Arg
            770                 775                 780

Thr Cys Thr His Asn Thr Asn Asp Cys Asn Pro Leu Pro Cys Tyr Asn
785                 790                 795                 800

Gly Gly Ile Cys Val Asp Gly Val Asn Trp Phe Arg Cys Glu Cys Ala
                805                 810                 815

Pro Gly Phe Ala Gly Pro Asp Cys Arg Ile Asn Ile Asp Glu Cys Gln
            820                 825                 830

Ser Ser Pro Cys Ala Tyr Gly Ala Thr Cys Val Asp Glu Ile Asn Gly
            835                 840                 845

Tyr Arg Cys Ser Cys Pro Pro Gly Arg Ala Gly Pro Arg Cys Gln Glu
            850                 855                 860

Val Ile Gly Phe Gly Arg Ser Cys Trp Ser Arg Gly Thr Pro Phe Pro
865                 870                 875                 880

His Gly Ser Ser Trp Val Glu Asp Cys Asn Ser Cys Arg Cys Leu Asp
                885                 890                 895

Gly Arg Arg Asp Cys Ser Lys Val Trp Cys Gly Trp Lys Pro Cys Leu
            900                 905                 910

Leu Ala Gly Gln Pro Glu Ala Leu Ser Ala Gln Cys Pro Leu Gly Gln
            915                 920                 925

Arg Cys Leu Glu Lys Ala Pro Gly Gln Cys Leu Arg Pro Pro Cys Glu
            930                 935                 940

Ala Trp Gly Glu Cys Gly Ala Glu Pro Pro Ser Thr Pro Cys Leu
945                 950                 955                 960

Pro Arg Ser Gly His Leu Asp Asn Asn Cys Ala Arg Leu Thr Leu His
                965                 970                 975

Phe Asn Arg Asp His Val Pro Gln Gly Thr Thr Val Gly Ala Ile Cys
            980                 985                 990

Ser Gly Ile Arg Ser Leu Pro Ala  Thr Arg Ala Val Ala  Arg Asp Arg
            995                 1000                1005
```

```
Leu Leu Val Leu Cys Asp Arg Ala Ser Gly Ala Ser Ala
        1010                1015                1020

Val Glu Val Ala Val Ser Phe Ser Pro Ala Arg Asp Leu Pro Asp
    1025                1030                1035

Ser Ser Leu Ile Gln Gly Ala Ala His Ala Ile Val Ala Ala Ile
    1040                1045                1050

Thr Gln Arg Gly Asn Ser Ser Leu Leu Leu Ala Val Thr Glu Val
    1055                1060                1065

Lys Val Glu Thr Val Val Thr Gly Gly Ser Ser Thr Gly Leu Leu
    1070                1075                1080

Val Pro Val Leu Cys Gly Ala Phe Ser Val Leu Trp Leu Ala Cys
    1085                1090                1095

Val Val Leu Cys Val Trp Trp Thr Arg Lys Arg Arg Lys Glu Arg
    1100                1105                1110

Glu Arg Ser Arg Leu Pro Arg Glu Glu Ser Ala Asn Asn Gln Trp
    1115                1120                1125

Ala Pro Leu Asn Pro Ile Arg Asn Pro Ile Glu Arg Pro Gly Gly
    1130                1135                1140

His Lys Asp Val Leu Tyr Gln Cys Lys Asn Phe Thr Pro Pro Pro
    1145                1150                1155

Arg Arg Ala Asp Glu Ala Leu Pro Gly Pro Ala Gly His Ala Ala
    1160                1165                1170

Val Arg Glu Asp Glu Glu Asp Glu Asp Leu Gly Arg Gly Glu Glu
    1175                1180                1185

Asp Ser Leu Glu Ala Glu Lys Phe Leu Ser His Lys Phe Thr Lys
    1190                1195                1200

Asp Pro Gly Arg Ser Pro Gly Arg Pro Ala His Trp Ala Ser Gly
    1205                1210                1215

Pro Lys Val Asp Asn Arg Ala Val Arg Ser Ile Asn Glu Ala Arg
    1220                1225                1230

Tyr Ala Gly Lys Glu
    1235

<210> SEQ ID NO 45
<211> LENGTH: 1071
<212> TYPE: PRT
<213> ORGANISM: Mus musculus

<400> SEQUENCE: 45

Met Arg Ser Pro Arg Thr Arg Gly Arg Pro Gly Arg Pro Leu Ser Leu
1               5                   10                  15

Leu Leu Ala Leu Leu Cys Ala Leu Arg Ala Lys Val Cys Gly Ala Ser
                20                  25                  30

Gly Gln Phe Glu Leu Glu Ile Leu Ser Met Gln Asn Val Asn Gly Glu
            35                  40                  45

Leu Gln Asn Gly Asn Cys Cys Gly Gly Val Arg Asn Pro Gly Asp Arg
        50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
```

```
            115                 120                 125
Pro Arg Ser Tyr Thr Leu Leu Val Glu Ala Trp Asp Ser Ser Asn Asp
        130                 135                 140
Thr Ile Gln Pro Asp Ser Ile Ile Glu Lys Ala Ser His Ser Gly Met
145                 150                 155                 160
Ile Asn Pro Ser Arg Gln Trp Gln Thr Leu Lys Gln Asn Thr Gly Ile
                165                 170                 175
Ala His Phe Glu Tyr Gln Ile Arg Val Thr Cys Asp Asp His Tyr Tyr
            180                 185                 190
Gly Phe Gly Cys Asn Lys Phe Cys Arg Pro Arg Asp Asp Phe Phe Gly
        195                 200                 205
His Tyr Ala Cys Asp Gln Asn Gly Asn Lys Thr Cys Met Glu Gly Trp
    210                 215                 220
Met Gly Pro Asp Cys Asn Lys Ala Ile Cys Arg Gln Gly Cys Ser Pro
225                 230                 235                 240
Lys His Gly Ser Cys Lys Leu Pro Gly Asp Cys Arg Cys Gln Tyr Gly
                245                 250                 255
Trp Gln Gly Leu Tyr Cys Asp Lys Cys Ile Pro His Pro Gly Cys Val
            260                 265                 270
His Gly Thr Cys Asn Glu Pro Trp Gln Cys Leu Cys Glu Thr Asn Trp
        275                 280                 285
Gly Gly Gln Leu Cys Asp Lys Asp Leu Asn Tyr Cys Gly Thr His Gln
    290                 295                 300
Pro Cys Leu Asn Arg Gly Thr Cys Ser Asn Thr Gly Pro Asp Lys Tyr
305                 310                 315                 320
Gln Cys Ser Cys Pro Glu Gly Tyr Ser Gly Pro Asn Cys Glu Ile Ala
                325                 330                 335
Glu His Ala Cys Leu Ser Asp Pro Cys His Asn Arg Gly Ser Cys Lys
            340                 345                 350
Glu Thr Ser Ser Gly Phe Glu Cys Glu Cys Ser Pro Gly Trp Thr Gly
        355                 360                 365
Pro Thr Cys Ser Thr Asn Ile Asp Asp Cys Ser Pro Asn Asn Cys Ser
    370                 375                 380
His Gly Gly Thr Cys Gln Asp Leu Val Asn Gly Phe Lys Cys Val Cys
385                 390                 395                 400
Pro Pro Gln Trp Thr Gly Lys Thr Cys Gln Leu Asp Ala Asn Glu Cys
                405                 410                 415
Glu Ala Lys Pro Cys Val Asn Ala Arg Ser Cys Lys Asn Leu Ile Ala
            420                 425                 430
Ser Tyr Tyr Cys Asp Cys Leu Pro Gly Trp Met Gly Gln Asn Cys Asp
        435                 440                 445
Ile Asn Ile Asn Asp Cys Leu Gly Gln Cys Gln Asn Asp Ala Ser Cys
    450                 455                 460
Arg Asp Leu Val Asn Gly Tyr Arg Cys Ile Cys Pro Pro Gly Tyr Ala
465                 470                 475                 480
Gly Asp His Cys Glu Arg Asp Ile Asp Glu Cys Ala Ser Asn Pro Cys
                485                 490                 495
Leu Asn Gly Gly His Cys Gln Asn Glu Ile Asn Arg Phe Gln Cys Leu
            500                 505                 510
Cys Pro Thr Gly Phe Ser Gly Asn Leu Cys Gln Leu Asp Ile Asp Tyr
        515                 520                 525
Cys Glu Pro Asn Pro Cys Gln Asn Gly Ala Gln Cys Tyr Asn Arg Ala
    530                 535                 540
```

-continued

```
Ser Asp Tyr Phe Cys Lys Cys Pro Glu Asp Tyr Glu Gly Lys Asn Cys
545                 550                 555                 560

Ser His Leu Lys Asp His Cys Arg Thr Thr Thr Cys Glu Val Ile Asp
            565                 570                 575

Ser Cys Thr Val Ala Met Ala Ser Asn Asp Thr Pro Glu Gly Val Arg
                580                 585                 590

Tyr Ile Ser Ser Asn Val Cys Gly Pro His Gly Lys Cys Lys Ser Gln
            595                 600                 605

Ser Gly Gly Lys Phe Thr Cys Asp Cys Asn Lys Gly Phe Thr Gly Thr
        610                 615                 620

Tyr Cys His Glu Asn Ile Asn Asp Cys Glu Ser Asn Pro Cys Lys Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala His Cys Glu Asn Asn Ile Asn Asp Cys Ser
            660                 665                 670

Gln Asn Pro Cys His Tyr Gly Gly Thr Cys Arg Asp Leu Val Asn Asp
        675                 680                 685

Phe Tyr Cys Asp Cys Lys Asn Gly Trp Lys Gly Lys Thr Cys His Ser
        690                 695                 700

Arg Asp Ser Gln Cys Asp Glu Ala Thr Cys Asn Asn Gly Gly Thr Cys
705                 710                 715                 720

Tyr Asp Glu Val Asp Thr Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Asp Ser Phe Thr Cys
        755                 760                 765

Val Cys Lys Glu Gly Trp Glu Gly Pro Ile Cys Thr Gln Asn Thr Asn
        770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Gln Cys Ile Cys Pro Pro
        835                 840                 845

Gly His Ser Gly Ala Lys Cys His Glu Val Ser Gly Arg Ser Cys Ile
        850                 855                 860

Thr Met Gly Arg Val Ile Leu Asp Gly Ala Lys Trp Asp Asp Cys
865                 870                 875                 880

Asn Thr Cys Gln Cys Leu Asn Gly Arg Val Ala Cys Ser Lys Val Trp
                885                 890                 895

Cys Gly Pro Arg Pro Cys Arg Leu His Lys Ser His Asn Glu Cys Pro
            900                 905                 910

Ser Gly Gln Ser Cys Ile Pro Val Leu Asp Asp Gln Cys Phe Val Arg
        915                 920                 925

Pro Cys Thr Gly Val Gly Glu Cys Arg Ser Ser Ser Leu Gln Pro Val
        930                 935                 940

Lys Thr Lys Cys Thr Ser Asp Ser Tyr Tyr Gln Asp Asn Cys Ala Asn
945                 950                 955                 960
```

```
Ile Thr Phe Thr Phe Asn Lys Glu Met Met Ser Pro Gly Leu Thr Thr
            965                 970                 975

Glu His Ile Cys Ser Glu Leu Arg Asn Leu Asn Ile Leu Lys Asn Val
        980                 985                 990

Ser Ala Glu Tyr Ser Ile Tyr Ile Ala Cys Glu Pro Ser Leu Ser Ala
    995                 1000                1005

Asn Asn Glu Ile His Val Ala Ile Ser Ala Glu Asp Ile Arg Asp
    1010                1015                1020

Asp Gly Asn Pro Val Lys Glu Ile Thr Asp Lys Ile Ile Asp Leu
    1025                1030                1035

Val Ser Lys Arg Asp Gly Asn Ser Ser Leu Ile Ala Ala Val Ala
    1040                1045                1050

Glu Val Arg Val Gln Arg Arg Gly Arg Ala His His His His
    1055                1060                1065

His His His
    1070

<210> SEQ ID NO 46
<211> LENGTH: 8
<212> TYPE: PRT
<213> ORGANISM: Artificial Sequence
<220> FEATURE:
<223> OTHER INFORMATION: FLAG-tag

<400> SEQUENCE: 46

Asp Tyr Lys Asp Asp Asp Asp Lys
1               5

<210> SEQ ID NO 47
<211> LENGTH: 17
<212> TYPE: PRT
<213> ORGANISM: Artificial Sequence
<220> FEATURE:
<223> OTHER INFORMATION: 133R0201 Heavy chain CDR2

<400> SEQUENCE: 47

Ala Ile Tyr Pro Asp Ser Ser Asn Lys Tyr Tyr Ala Asp Ser Val Lys
1               5                   10                  15

Gly

<210> SEQ ID NO 48
<211> LENGTH: 17
<212> TYPE: PRT
<213> ORGANISM: Artificial Sequence
<220> FEATURE:
<223> OTHER INFORMATION: 133R0203 Heavy chain CDR2

<400> SEQUENCE: 48

Ala Ile Ser Pro Glu Ala Ser Asn Lys Tyr Tyr Ala Asp Ser Val Lys
1               5                   10                  15

Gly

<210> SEQ ID NO 49
<211> LENGTH: 17
<212> TYPE: PRT
<213> ORGANISM: Artificial Sequence
<220> FEATURE:
<223> OTHER INFORMATION: 133R0205 Heavy chain CDR2

<400> SEQUENCE: 49

Ala Ile Tyr Pro Ala Ser Ser Asn Lys Tyr Tyr Ala Asp Ser Val Lys
1               5                   10                  15
```

Gly

```
<210> SEQ ID NO 50
<211> LENGTH: 119
<212> TYPE: PRT
<213> ORGANISM: Artificial Sequence
<220> FEATURE:
<223> OTHER INFORMATION: 133R0201 Heavy chain variable region

<400> SEQUENCE: 50
```

| Gln | Val | Gln | Leu | Val | Glu | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Met | His | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Ala | Ile | Tyr | Pro | Asp | Ser | Ser | Asn | Lys | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Lys | Tyr | Asp | Ile | Pro | Asp | Ala | Phe | Asp | Ile | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser |
|---|---|---|---|---|---|---|
| | | | 115 | | | |

```
<210> SEQ ID NO 51
<211> LENGTH: 119
<212> TYPE: PRT
<213> ORGANISM: Artificial Sequence
<220> FEATURE:
<223> OTHER INFORMATION: 133R0203 Heavy chain variable region

<400> SEQUENCE: 51
```

| Gln | Val | Gln | Leu | Val | Glu | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Met | His | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Ala | Ile | Ser | Pro | Glu | Ala | Ser | Asn | Lys | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Lys | Tyr | Asp | Ile | Pro | Asp | Ala | Phe | Asp | Ile | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser |
|---|---|---|---|---|---|---|
| | | | 115 | | | |

```
<210> SEQ ID NO 52
<211> LENGTH: 119
<212> TYPE: PRT
<213> ORGANISM: Artificial Sequence
<220> FEATURE:
<223> OTHER INFORMATION: 133R0205 Heavy chain variable region
```

<400> SEQUENCE: 52

| Gln | Val | Gln | Leu | Val | Glu | Ser | Gly | Gly | Val | Val | Gln | Pro | Gly | Arg |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Ser Leu Arg Leu Ser Cys Ala Ala Ser Gly Phe Thr Phe Ser Ser Tyr
           20                  25                  30

Ala Met His Trp Val Arg Gln Ala Pro Gly Lys Gly Leu Glu Trp Val
            35                  40                  45

Ala Ala Ile Tyr Pro Ala Ser Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Tyr Asp Ile Pro Asp Ala Phe Asp Ile Trp Gly Gln
            100                 105                 110

Gly Thr Leu Val Thr Val Ser
        115

<210> SEQ ID NO 53
<211> LENGTH: 357
<212> TYPE: DNA
<213> ORGANISM: Artificial Sequence
<220> FEATURE:
<223> OTHER INFORMATION: 133R0201 Heavy chain variable region

<400> SEQUENCE: 53

```
caggtgcagc tggtggaatc cggcggaggc gtggtgcagc ctggcagatc cctgagactg      60
tcctgcgccg cctccggctt caccttctcc agctacgcca tgcactgggt ccgacaggcc     120
cctggcaagg gcctggaatg gtggccgcc atctaccccg actcctccaa caagtactac     180
gccgactccg tgaagggccg gttcacaatc tcccgggaca actccaagaa caccctgtac     240
ctgcagatga actccctgcg ggccgaggac accgccgtgt actactgcgc cagagataag     300
tacgacatcc ccgacgcctt cgacatctgg ggccagggca ccctggtcac cgtgtcc       357
```

<210> SEQ ID NO 54
<211> LENGTH: 357
<212> TYPE: DNA
<213> ORGANISM: Artificial Sequence
<220> FEATURE:
<223> OTHER INFORMATION: 133R0203 Heavy chain variable region

<400> SEQUENCE: 54

```
caggtgcagc tggtggaatc cggcggaggc gtggtgcagc ctggcagatc cctgagactg      60
tcctgcgccg cctccggctt caccttctcc agctacgcca tgcactgggt ccgacaggcc     120
cctggcaagg gcctggaatg gtggccgcc atctccccg aggcctccaa caagtactac      180
gccgactccg tgaagggccg gttcacaatc tcccgggaca actccaagaa caccctgtac     240
ctgcagatga actccctgcg ggccgaggac accgccgtgt actactgcgc cagagataag     300
tacgacatcc ccgacgcctt cgacatctgg ggccagggca ccctggtcac cgtgtcc       357
```

<210> SEQ ID NO 55
<211> LENGTH: 357
<212> TYPE: DNA
<213> ORGANISM: Artificial Sequence
<220> FEATURE:
<223> OTHER INFORMATION: 133R0205 Heavy chain variable region

<400> SEQUENCE: 55

-continued

```
caggtgcagc tggtggaatc cggcggaggc gtggtgcagc ctggcagatc cctgagactg      60
tcctgcgccg cctccggctt caccttctcc agctacgcca tgcactgggt ccgacaggcc     120
cctggcaagg gcctggaatg ggtggccgcc atctacccg catcctccaa caagtactac      180
gccgactccg tgaagggccg gttcacaatc tcccggaca  actccaagaa caccctgtac     240
ctgcagatga actccctgcg ggccgaggac accgccgtgt actactgcgc cagagataag     300
tacgacatcc ccgacgcctt cgacatctgg ggccagggca ccctggtcac cgtgtcc       357
```

JAGGED-BINDING AGENTS AND USES THEREOF

CROSS-REFERENCE TO RELATED APPLICATIONS

This application claims the priority benefit of U.S. Provisional Application No. 61/262,879, filed Nov. 19, 2009, which is hereby incorporated by reference herein in its entirety.

FIELD OF THE INVENTION

The field of this invention generally relates to antibodies and other agents that bind to Jagged proteins, as well as methods of using the antibodies or other agents for the treatment of diseases, such as cancer.

BACKGROUND OF THE INVENTION

Cancer is one of the leading causes of death in the developed world, resulting in over 550,000 deaths per year in the United States alone. Almost one and half million people are diagnosed with cancer in the U.S. each year, and currently one in four deaths in the U.S. is due to cancer. (Jemal et al., 2008, *Cancer J. Clin.* 58:71-96). Although there are many drugs and compounds currently available and in use, these numbers show that a need continues to exist for new therapeutic agents for the treatment of cancer.

The Notch signaling pathway is a universally conserved signal transduction system. It is involved in cell fate determination during development including embryonic pattern formation and post-embryonic tissue maintenance. In addition, Notch signaling has been identified as a critical factor in the maintenance of hematopoietic stem cells (HSCs).

The mammalian Notch receptor family includes four members, Notch1, Notch2, Notch3 and Notch4. Notch receptors are large single-pass type I transmembrane proteins with several conserved structural motifs. The extracellular domain contains a variable number of epidermal growth factor (EGF)-like repeats involved in ligand binding and three cysteine-rich LIN-12/Notch repeats (LNRs) involved in Notch heterodimerization. The intracellular domain contains a RAM23 motif involved in binding Notch downstream signaling proteins, 7 CDC 10/ankyrin repeats also involved in mediating downstream signaling and a PEST domain involved in Notch protein degradation.

Mammalian Notch ligands include Delta-like 1 (DLL1), Delta-like 3 (DLL3), Delta-like 4 (DLL4), Jagged1 and Jagged2. Similar to Notch receptors, Notch ligands are type I transmembrane proteins with several conserved structural motifs. Extracellular motifs common to all Notch ligands include a single Delta/Serrate/Lag-2 (DSL) domain involved in receptor binding, as well as a variable number of EGF-like repeats that may be involved in stabilizing receptor binding. The extracellular domain of Jagged proteins contains a cysteine-rich region which has partial homology to the von Willebrand factor type C domain and is likely involved in ligand dimerization. This motif is not present in DLL family members. (Leong et al., 2006, *Blood*, 107:2223-2233).

The extracellular domain of a Notch receptor interacts with the extracellular domain of a Notch ligand, typically on adjacent cells, resulting in two proteolytic cleavages of the Notch receptor. One extracellular cleavage is mediated by an ADAM (A Disintegrin And Metallopeptidase) protease and a second cleavage within the transmembrane domain is mediated by the gamma secretase complex. This latter cleavage generates the Notch intracellular domain (ICD), which translocates to the nucleus where it activates the CBF1, Suppressor of Hairless, Lag-2 (CSL) family of transcription factors as the major downstream effectors to increase transcription of nuclear basic helix-loop-helix transcription factors of the Hairy/Enhancer of Split (HES) family. (Artavanis et al., 1999, *Science* 284:770; Brennan and Brown, 2003, *Breast Cancer Res.* 5:69; Iso et al., 2003, *Arterioscler. Thromb. Vasc. Biol.* 23:543).

The Notch pathway has been associated with several human diseases, including Alagille's syndrome and the neural degenerative disease CADASIL. In addition, the Notch pathway has been linked to the pathogenesis of both hematologic and solid tumors and cancers. Numerous cellular functions and microenvironmental cues associated with tumorigenesis have been shown to be modulated by Notch pathway signaling, including cell proliferation, apoptosis, adhesion, and angiogenesis. (Leong et al., 2006, *Blood*, 107:2223-2233). In addition, Notch receptors and/or Notch ligands have been shown to play potential oncogenic roles in a number of human cancers, including acute myelogenous leukemia, B cell chronic lymphocytic leukemia, Hodgkin lymphoma, multiple myeloma, T cell acute lymphoblastic leukemia, brain cancer, breast cancer, cervical cancer, colon cancer, lung cancer, pancreatic cancer, prostate cancer and skin cancer. (Leong et al., 2006, *Blood*, 107:2223-2233). Thus, the Notch pathway has been identified as a potential target for cancer therapy.

The Notch pathway is also involved in multiple aspects of vascular development including proliferation, migration, smooth muscle differentiation, angiogenesis and arterial-venous differentiation (Iso et al., 2003, *Arterioscler. Thromb. Vasc. Biol.* 23:543). It is clear that the Notch family is critically important for the proper construction of the vascular system. For example, global knockouts of Notch1 alone or Notch1/4 together are lethal in the embryo due to severe vascular defects. Global, as well as endothelium-specific, knockouts of Jagged1 induce embryonic death with vascular defects (Dufraine et al., 2008, *Oncogene* 27:5132-5137). In humans, mutations in Jagged1 are associated with Alagille's syndrome, a developmental disorder that includes vascular defects, and mutations in Notch3 are responsible for an inherited vascular dementia (CADASIL) in which vessel homeostasis is defective (Joutel et al., 1996, *Nature* 383:707-10). Thus, the Notch pathway has also been identified as a potential target for affecting angiogenesis.

SUMMARY OF THE INVENTION

The present invention provides agents that bind to Jagged, a Notch ligand, and compositions, such as pharmaceutical compositions, comprising those agents. In certain embodiments, the Jagged-binding agents are novel polypeptides, such as antibodies, fragments of such antibodies, and other polypeptides related to such antibodies. In certain embodiments, the Jagged-binding agents are antibodies that specifically bind to Jagged1 (e.g., human Jagged1). In certain embodiments, the Jagged-binding agents that specifically bind to Jagged1 further specifically bind to Jagged2 (e.g., human Jagged2). In certain embodiments, the Jagged-binding agents are antibodies that specifically bind to Jagged2 (e.g., human Jagged2). The invention further provides methods of inhibiting the growth of a tumor by administering the Jagged-binding agents to a subject with a tumor. The invention further provides methods of treating cancer by administering the Jagged-binding agents to a subject in need thereof. In some embodiments, the methods of treating cancer or inhibiting tumor growth comprise targeting cancer stem cells with the Jagged-binding agents. In certain embodiments, the methods comprise reducing the frequency of cancer stem cells in a tumor, reducing the number of cancer stem cells in a tumor, reducing the tumorigenicity of a tumor, and/or reducing the tumorigenicity of a tumor by reducing the number or frequency of cancer stem cells in the tumor. The invention also provides methods of using the Jagged-binding agents in the treatment of cancer and/or in the inhibition of the growth of tumors comprising cancer stem cells.

In one aspect, the invention provides a binding agent that specifically binds Jagged. In certain embodiments, the Jagged-binding agent is an antibody that specifically binds to an extracellular domain of Jagged. In some embodiments, the Jagged-binding agent (e.g., an antibody) binds to a region comprising the DSL domain of Jagged. In some embodiments, the Jagged-binding agent (e.g., an antibody) binds to a region comprising EGF1, EGF2 and/or EGF3 of Jagged. In some embodiments, the Jagged is Jagged1. In some embodiments, the Jagged is Jagged2. In some embodiments, the Jagged is human Jagged1 and human Jagged2. In some embodiments, the Jagged-binding agent (e.g., an antibody) modulates Jagged activity. In some embodiments, the Jagged-binding agent (e.g., an antibody) is an antagonist of Jagged. In some embodiments, the Jagged-binding agent (e.g., an antibody) inhibits or interferes with binding of Jagged to a Notch receptor. In some embodiments, the Jagged-binding agent (e.g., an antibody) inhibits Notch signaling or Notch activation.

In certain embodiments, the Jagged-binding agent (e.g., an antibody) that specifically binds to an extracellular domain of human Jagged1 and/or human Jagged2 comprises (a) a heavy chain CDR1 comprising SYWIH (SEQ ID NO:9) or a variant thereof comprising 1, 2, 3, or 4 amino acid substitutions, a heavy chain CDR2 comprising RIYPGIGSTYYNEKFKD (SEQ ID NO:10) or a variant thereof comprising 1, 2, 3, or 4 amino acid substitutions, and a heavy chain CDR3 comprising NGGFFDY (SEQ ID NO:11) or a variant thereof comprising 1, 2, 3, or 4 amino acid substitutions; and/or (b) a light chain CDR1 comprising RASESVDSYGNSFMH (SEQ ID NO:12) or a variant thereof comprising 1, 2, 3, or 4 amino acid substitutions, a light chain CDR2 comprising RASNLES (SEQ ID NO:13) or a variant thereof comprising 1, 2, 3, or 4 amino acid substitutions, and a light chain CDR3 comprising QQSNEDPWT (SEQ ID NO:14) or a variant thereof comprising 1, 2, 3, or 4 amino acid substitutions. In certain embodiments, the amino acid substitutions are conservative amino acid substitutions.

In some embodiments, the Jagged-binding agent (e.g., an antibody) that specifically binds to an extracellular domain of human Jagged1 and/or human Jagged2 comprises (a) a heavy chain CDR1 comprising SYAMH (SEQ ID NO:23) or a variant thereof comprising 1, 2, 3, or 4 amino acid substitutions, a heavy chain CDR2 comprising VISYDGSNKYYADSVKG (SEQ ID NO:24), AIYPDSSNKYYADSVKG (SEQ ID NO:47), AISPEASNKYYADSVKG (SEQ ID NO:48), or AIYPASSNKYYADSVKG (SEQ ID NO:49), or a variant thereof comprising 1, 2, 3, or 4 amino acid substitutions, and a heavy chain CDR3 comprising DKYDIPDAFDI (SEQ ID NO:25) or a variant thereof comprising 1, 2, 3, or 4 amino acid substitutions; and/or (b) a light chain CDR1 comprising RASQGISNDLA (SEQ ID NO:26) or a variant thereof comprising 1, 2, 3, or 4 amino acid substitutions, a light chain CDR2 comprising ATSTLQS (SEQ ID NO:27) or a variant thereof comprising 1, 2, 3, or 4 amino acid substitutions, and a light chain CDR3 comprising QQSYNAPI (SEQ ID NO:28) or a variant thereof comprising 1, 2, 3, or 4 amino acid substitutions. In certain embodiments, the amino acid substitutions are conservative amino acid substitutions.

In some embodiments, the Jagged-binding agent (e.g., an antibody) that specifically binds to an extracellular domain of human Jagged1 comprises (a) a heavy chain CDR1 comprising SSNWWS (SEQ ID NO:37) or a variant thereof comprising 1, 2, 3, or 4 amino acid substitutions, a heavy chain CDR2 comprising EIFHGENTNYNPSLKS (SEQ ID NO:38) or a variant thereof comprising 1, 2, 3, or 4 amino acid substitutions, and a heavy chain CDR3 comprising NPGIGAAKFDS (SEQ ID NO:39) or a variant thereof comprising 1, 2, 3, or 4 amino acid substitutions; and/or (b) a light chain CDR1 comprising KSSQSLLHSDGKTYLY (SEQ ID NO:40) or a variant thereof comprising 1, 2, 3, or 4 amino acid substitutions, a light chain CDR2 comprising EVSNRFS (SEQ ID NO:41) or a variant thereof comprising 1, 2, 3, or 4 amino acid substitutions, and a light chain CDR3 comprising MQHIDFP (SEQ ID NO:42) or a variant thereof comprising 1, 2, 3, or 4 amino acid substitutions. In certain embodiments, the amino acid substitutions are conservative amino acid substitutions.

In certain embodiments, the Jagged-binding agent (e.g., an antibody) that specifically binds to an extracellular domain of human Jagged1 and/or human Jagged2 comprises (a) a heavy chain variable region having at least about 90%, at least about 95% or 100% sequence identity to SEQ ID NO:5; and/or (b) a light chain variable region having at least about 90%, at least about 95% or 100% sequence identity to SEQ ID NO:7. In certain embodiments, the Jagged-binding agent (e.g., antibody) that specifically binds to an extracellular domain of human Jagged1 or human Jagged2 comprises (a) a heavy chain variable region having at least about 90%, at least about 95% or 100% sequence identity to SEQ ID NO:19, SEQ ID NO:50, SEQ ID NO:51, or SEQ ID NO:52; and/or (b) a light chain variable region having at least about 90%, at least about 95% or 100% sequence identity to SEQ ID NO:21. In certain embodiments, the Jagged-binding agent (e.g., antibody) that specifically binds to an extracellular domain of human Jagged1 comprises (a) a heavy chain variable region having at least about 90%, at least about 95% or 100% sequence identity to SEQ ID NO:33; and/or (b) a light chain variable region having at least about 90%, at least about 95% or 100% sequence identity to SEQ ID NO:35. In some embodiments, the Jagged-binding agent is antibody 64M51, antibody 64R7 or antibody 64R1B. In some embodiments, the Jagged-binding agent is antibody 133R0201, antibody 133R0203 or antibody 133R0205. In some embodiments, the Jagged-binding agent is a humanized form of antibody 64M51.

In certain embodiments, the Jagged-binding agent comprises the heavy chains and light chains of the 64R1B IgG2 antibody (with or without the leader sequence). In certain embodiments, the Jagged-binding agent is the 64R1B IgG2 antibody. DNA encoding the heavy chains and light chains of the 64R1B IgG2 antibody was deposited with the American Type Culture Collection (ATCC), 10801 University Boulevard, Manassas, Va., USA, under the conditions of the Budapest Treaty on Nov. 13, 2009 and assigned ATCC deposit designation number PTA-10469. In certain embodiments, the Jagged-binding agent comprises the heavy chains and light chains of the 64R7 IgG2 antibody (with or without the leader sequence). In certain embodiments, the Jagged-binding agent is the 64R7 IgG2 antibody. DNA encoding the heavy chains and light chains of the 64R7 IgG2 antibody was deposited with the ATCC, under the conditions of the Budapest Treaty on Nov. 13, 2009 and assigned ATCC deposit designation number PTA-10470. In certain embodiments, the Jagged-binding agent comprises the heavy chains and light chains of the 64M51 antibody (with or without the leader sequence). In certain embodiments, the Jagged-binding agent is the 64M51 antibody. In some embodiments, the Jagged-binding agent is a humanized form of the 64M51 antibody. The hybridoma cell line producing the 64M51 antibody was deposited with the ATCC under the conditions of the Budapest Treaty on Nov. 13, 2009 and assigned ATCC deposit designation number PTA-10468.

In some embodiments, the invention provides a Jagged-binding agent (e.g., an antibody) that specifically binds to the same or an over-lapping Jagged epitope as the epitope to which antibody 64M51 binds. In some embodiments, the invention provides a Jagged-binding agent (e.g., an antibody) that specifically binds to the same or an over-lapping Jagged epitope as the epitope to which antibody 64R7 binds. In some embodiments, the invention provides a Jagged-binding agent (e.g., an antibody) that specifically binds to the same or an over-lapping Jagged epitope as the epitope to which antibody 64R1B binds. In some embodiments, the invention provides a Jagged-binding agent (e.g., an antibody) that specifically binds to the same or an over-lapping Jagged epitope as the epitope to which antibody 133R0201 binds. In some embodiments, the invention provides a Jagged-binding agent (e.g., an antibody) that specifically binds to the same or an over-lapping Jagged epitope as the epitope to which antibody 133R0203 binds. In some embodiments, the invention provides a Jagged-binding agent (e.g., an antibody) that specifically binds to the same or an over-lapping Jagged epitope as the epitope to which antibody 133R0205 binds.

In certain embodiments of each of the aforementioned aspects or embodiments, as well as other aspects and/or embodiments described elsewhere herein, the Jagged-binding agent is an antibody. In certain embodiments, the antibody is a recombinant antibody. In certain embodiments, the antibody is a monoclonal antibody, a chimeric antibody, a humanized antibody, or a human antibody. In some embodiments, the antibody is an antibody fragment. In certain embodiments, the antibody or antibody fragment is monovalent, monospecific, bivalent, bispecific, or multispecific. In certain embodiments, the antibody is conjugated to a cytotoxic moiety. In certain embodiments, the antibody is isolated. In still further embodiments, the antibody is substantially pure.

In another aspect, the invention provides a Jagged-binding agent (e.g., an antibody) that competes for specific binding to an extracellular domain of human Jagged with an antibody of the invention. In some embodiments, the Jagged-binding agent (e.g., an antibody) competes for specific binding to an extracellular domain of human Jagged1 and/or human Jagged2 with an antibody that comprises a heavy chain variable region comprising SEQ ID NO:5 and a light chain variable region comprising SEQ ID NO:7. In certain embodiments, the Jagged-binding agent (e.g., an antibody) competes for specific binding to an extracellular domain of human Jagged1 and/or human Jagged2 with an antibody that comprises a heavy chain variable region comprising SEQ ID NO:19 and a light chain variable region comprising SEQ ID NO:21. In certain embodiments, the Jagged-binding agent (e.g., an antibody) competes for specific binding to an extra-cellular domain of human Jagged1 and/or human Jagged2 with an antibody that comprises a heavy chain variable region comprising SEQ ID NO:50 and a light chain variable region comprising SEQ ID NO:21. In certain embodiments, the Jagged-binding agent (e.g., an antibody) competes for specific binding to an extracellular domain of human Jagged1 and/or human Jagged2 with an antibody that comprises a heavy chain variable region comprising SEQ ID NO:51 and a light chain variable region comprising SEQ ID NO:21. In certain embodiments, the Jagged-binding agent (e.g., an antibody) competes for specific binding to an extracellular domain of human Jagged1 and/or human Jagged2 with an antibody that comprises a heavy chain variable region comprising SEQ ID NO:52 and a light chain variable region comprising SEQ ID NO:21. In certain embodiments, the binding agent (e.g., an antibody) competes for specific binding to an extracellular domain of human Jagged1 with an antibody that comprises a heavy chain variable region comprising SEQ ID NO:33 and a light chain variable region comprising SEQ ID NO:35. In some embodiments, the binding agent competes for specific binding to an extracellular domain of human Jagged1 and/or Jagged2 with an antibody in an in vitro competitive binding assay.

In another aspect, the invention provides a Jagged-binding agent that competes for specific binding to an extracellular domain of human Jagged with any one of the following antibodies: 64M51, 64R7, 64R1B, 133R0201, 133R0203, or 133R0205. In some embodiments, the invention provides a Jagged-binding agent that competes for specific binding to an extracellular domain of human Jagged1 with antibody 64M51, antibody 64R7, antibody 133R0201, antibody 133R0203 or antibody 133R0205. In some embodiments, the invention provides a Jagged-binding agent that competes for specific binding to an extracellular domain of human Jagged2 with antibody 64M51, antibody 64R7, antibody 133R0201, antibody 133R0203 or antibody 133R0205. In some embodiments, the invention provides a Jagged-binding agent that competes for specific binding to an extracellular domain of human Jagged1 with antibody 64R1B.

In another aspect, the invention provides a Jagged-binding agent that specifically binds to the extracellular domain of a human Jagged, wherein the Jagged-binding agent comprises a polypeptide. In some embodiments, the polypeptide that binds to the extracellular domain of a human Jagged1 and/or Jagged2 comprises (a) a polypeptide having at least about 80% sequence identity to SEQ ID NO:5, and/or a polypeptide having at least about 80% sequence identity to SEQ ID NO:7. In some embodiments, the polypeptide that binds to the extracellular domain of a human Jagged1 and/or Jagged2 comprises (a) a polypeptide having at least about 80% sequence identity to SEQ ID NO:19, and/or a polypeptide having at least about 80% sequence identity to SEQ ID NO:21. In some embodiments, the polypeptide that binds to the extracellular domain of a human Jagged1 and/or Jagged2 comprises (a) a polypeptide having at least about 80% sequence identity to SEQ ID NO:50, and/or a polypeptide having at least about 80% sequence identity to SEQ ID NO:21. In some embodiments, the polypeptide that binds to the extracellular domain of a human Jagged1 and/or Jagged2 comprises (a) a polypeptide having at least about 80% sequence identity to SEQ ID NO:51, and/or a polypeptide having at least about 80% sequence identity to SEQ ID NO:21. In some embodiments, the polypeptide that binds to the extracellular domain of a human Jagged1 and/or Jagged2 comprises (a) a polypeptide having at least about 80% sequence identity to SEQ ID NO:52, and/or a polypeptide having at least about 80% sequence identity to SEQ ID NO:21. In some embodiments, the polypeptide that binds to the extracellular domain of a human Jagged1 comprises (a) a polypeptide having at least about 80% sequence identity to SEQ ID NO:33, and/or a polypeptide having at least about 80% sequence identity to SEQ ID NO:35. In some embodiments, the polypeptide is isolated. In certain embodiments, the polypeptide is substantially pure.

In certain embodiments of each of the aforementioned aspects, as well as other aspects described herein, the Jagged-binding agent or polypeptide is an antibody.

In certain embodiments of each of the aforementioned aspects, as well as other aspects described herein, the Jagged-binding agent or polypeptide or antibody inhibits binding of human Jagged to a Notch receptor. In some embodiments, the human Jagged is Jagged1. In some embodiments, the human Jagged is Jagged2. In some embodiments, the Notch receptor is Notch1. In some embodiments, the Notch receptor is Notch2. In some embodiments, the Notch receptor is Notch3. In some embodiments, the Notch receptor is Notch4.

In certain embodiments of each of the aforementioned aspects, as well as other aspects described elsewhere herein, the Jagged-binding agent or antibody that specifically binds to and/or modulates the activity of Jagged1 further specifically binds to and/or modulates the activity of Jagged2. In certain embodiments, the antibody specifically binds to and/or modulates the activity of Jagged2.

In certain embodiments of each of the aforementioned aspects, as well as other aspects described elsewhere herein, the Jagged-binding agent is an antagonist of Jagged1. In some embodiments, the Jagged-binding agent is an antagonist of Jagged2. In some embodiments, the Jagged-binding agent is an antagonist of Jagged1 and Jagged2.

In certain embodiments of each of the aforementioned aspects, as well as other aspects described elsewhere herein, the Jagged-binding agent, e.g. an antibody, inhibits the binding of Jagged to a Notch receptor. In some embodiments, the Jagged-binding agent or antibody inhibits or blocks Notch receptor signaling. In some embodiments, the Jagged-binding agent or antibody inhibits or blocks Notch activation. In some embodiments, the Jagged-binding agent is an antagonist of a Notch receptor.

In another aspect, the invention provides a polynucleotide molecule encoding any of the antibodies and/or polypeptides of the aforementioned aspects, as well as other aspects as described herein. In some embodiments, an expression vector comprises the polynucleotide molecule. In other embodiments, a host cell comprises the expression vector. In some embodiments, a host cell comprises the polynucleotide molecule. In some embodiments, the host cell is a hybridoma cell line.

In one aspect, the invention provides a method of inhibiting the growth of a tumor in a subject, comprising administering to the subject a therapeutically effective amount of a Jagged-binding agent. In some embodiments, the tumor is a solid tumor. In some embodiments, the tumor is a colorectal tumor, a breast tumor, a prostate tumor, a pancreatic tumor, a lung tumor, a head and neck tumor or a melanoma tumor. In certain embodiments, the tumor comprises cancer stem cells. In certain embodiments, the Jagged-binding agent inhibits growth of the tumor by reducing the number and/or frequency of cancer stem cells in the tumor. In certain embodiments, the Jagged-binding agent is an antibody, such as an antibody that specifically binds to Jagged1 and/or Jagged2. In some embodiments, the Jagged is human Jagged1 and/or human Jagged2. In some embodiments, the subject is a human.

In another aspect, the invention provides a method of reducing the tumorigenicity of a tumor comprising cancer stem cells by reducing the frequency of cancer stem cells in the tumor, wherein the method comprises contacting the tumor with an effective amount of a Jagged-binding agent. In certain embodiments, the agent is an antibody, such as an antibody that specifically binds to human Jagged1 and/or human Jagged2. In some embodiments, the Jagged-binding agent modulates the activity of Jagged1 and/or Jagged2. In some embodiments, the modulation of Jagged1 and/or Jagged2 activity inhibits Jagged interaction with Notch. In some embodiments, the modulation of Jagged1 and/or Jagged2 activity inhibits Notch signaling. In some embodiments, the modulation of Jagged1 and/or Jagged2 activity inhibits Notch activation.

In another aspect, the invention provides a binding agent (e.g., an antibody) that specifically binds Jagged and has an effect on cancer stem stems. In some embodiments, the Jagged-binding agent reduces the frequency of cancer stem cells in a tumor, reduces the number of cancer stem cells in a tumor, reduces the tumorigenicity of a tumor, and/or reduces the tumorigenicity of a tumor by reducing the number and/or frequency of cancer stem cells in the tumor. In certain embodiments, the Jagged-binding agent (e.g., an antibody) specifically binds to Jagged1. In some embodiments, the Jagged-binding agent (e.g., an antibody) specifically binds to Jagged 2. In some embodiments, the Jagged-binding agent (e.g., an antibody) specifically binds to Jagged1 and Jagged2.

In certain embodiments of each of the aforementioned aspects, as well as other aspects described elsewhere herein, the tumors which are targeted are breast, colorectal, hepatic, renal, lung, pancreatic, ovarian, melanoma, prostate, or head and neck tumors.

In another aspect, the invention provides a method of treating cancer in a subject. In some embodiments, the method comprises administering to a subject a Jagged-binding agent. In some embodiments, the method comprises administering to a subject a therapeutically effective amount of any of the antibodies or polypeptides or agents described in the aforementioned aspects, as well as other aspects and embodiments described elsewhere herein. In some embodiments, the cancer to be treated is breast cancer, colorectal cancer, hepatic cancer, kidney cancer, liver cancer, lung cancer, pancreatic cancer, gastrointestinal cancer, melanoma, ovarian cancer, prostate cancer, cervical cancer, bladder cancer, glioblastoma, or head and neck cancer.

In certain embodiments of each of the aforementioned aspects, as well as other aspects described elsewhere herein, the treatment methods further comprise administering at least one additional therapeutic agent appropriate for effecting combination therapy (e.g., a chemotherapeutic agent or other anticancer agent, if cancer is to be treated).

Pharmaceutical compositions comprising both a Jagged-binding agent as described herein and a pharmaceutically acceptable vehicle are further provided, as are cell lines that produce the Jagged-binding agents. Methods of treating cancer and/or inhibiting tumor growth in a subject (e.g., a human) comprising administering to the subject an effective amount of a composition comprising the Jagged-binding agents are also provided.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTIONS OF THE DRAWINGS

FIG. 1. Identification of antibodies that bind to Jagged1 and/or Jagged2. Human HEK293 cells expressing human or mouse Jagged1 (Jag1) or Jagged2 (Jag2) and GFP were incubated with 64R1B, 64R7, 64M51 or control antibodies and phycoerythrin (PE) conjugated secondary antibody. Binding of antibodies to the Jagged-expressing cells was analyzed by flow cytometry. Shown are FACS analyses of antibody binding to the Jagged transfected cells. Binding is highlighted in each panel by the dark grey box insert.

Figure 2:
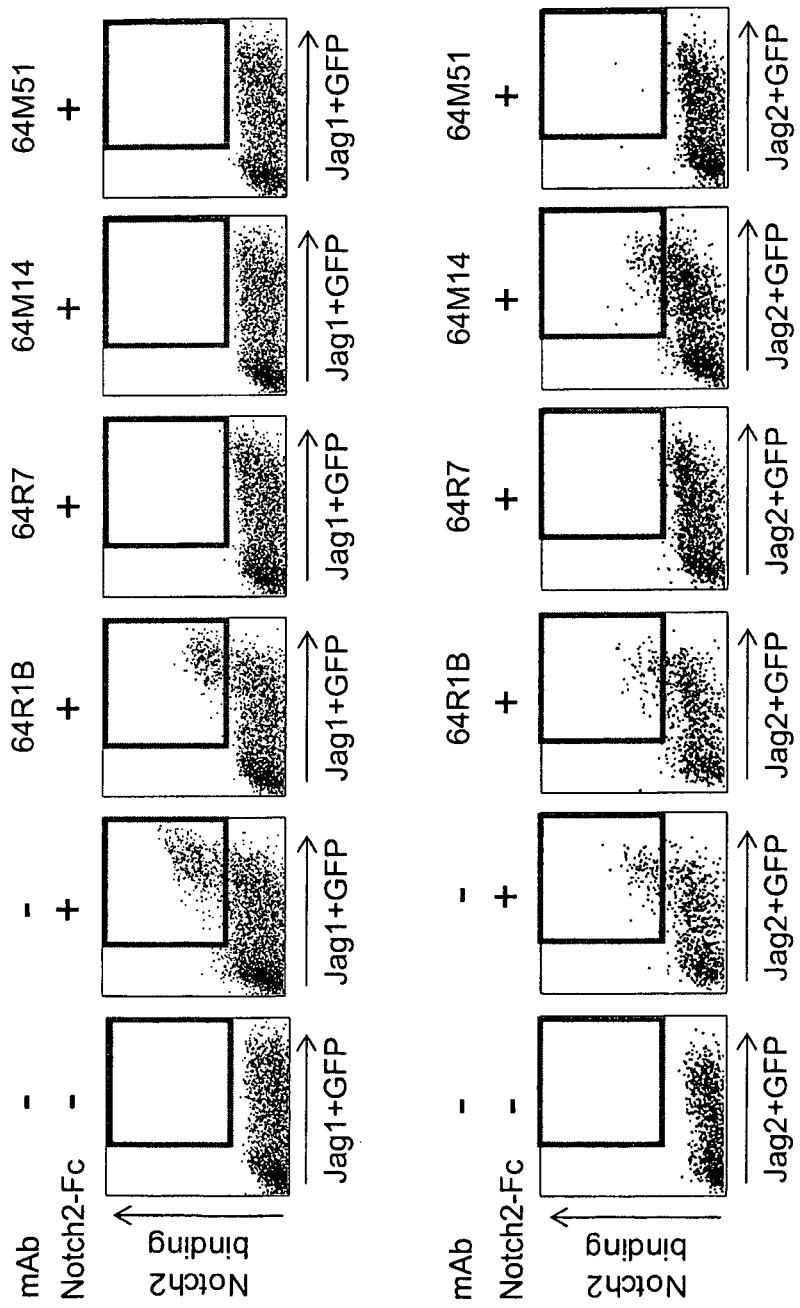

FIG. 2. Identification of antibodies that block Jagged-Notch interaction. Human HEK293 cells expressing human Jagged1 (Jag1) or Jagged2 (Jag2) and GFP were incubated with recombinant Notch2-Fc fusion protein in the presence of antibodies 64R1B, 64R7, 64M14 or 64M51. The binding of Notch2-Fc to transfected cells was detected by incubation with PE-conjugated secondary antibody and analyzed by flow cytometry. Shown are FACS analyses of antibody blocking of Notch2 binding to the Jagged transfected cells. Binding is highlighted in each panel by the dark grey box insert.

Figure 3:
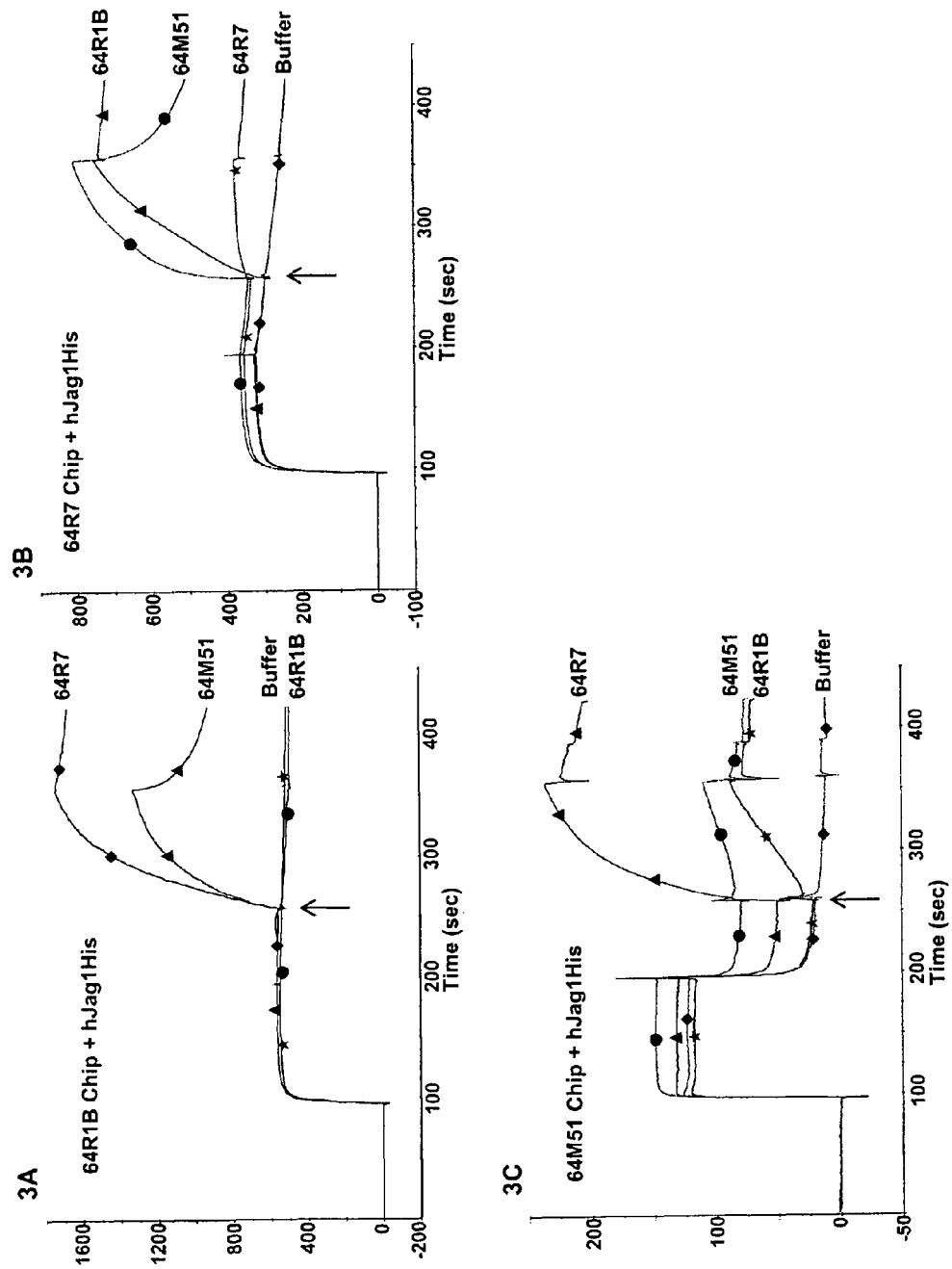

FIG. 3. Identification of distinct functional epitopes. In order to determine whether 64M51, 64R7 and 64R1B bound to distinct epitopes on Jagged1, epitope competition binding studies were conducted. Antibodies 64R1B (FIG. 3A), 64R7 (FIG. 3B) and 64M51 (FIG. 3C) were coated on CM5 Biacore chips. Human Jagged1 protein was then bound to the chip. Following binding of Jagged1 protein to each of the indicated antibody chips (64M51, 64R7 or 64R1B), the ability of additional Jagged antibodies to be bound was assessed. The arrow indicates the point where the injection of the solution antibody over the chip was started.

Figure 4:
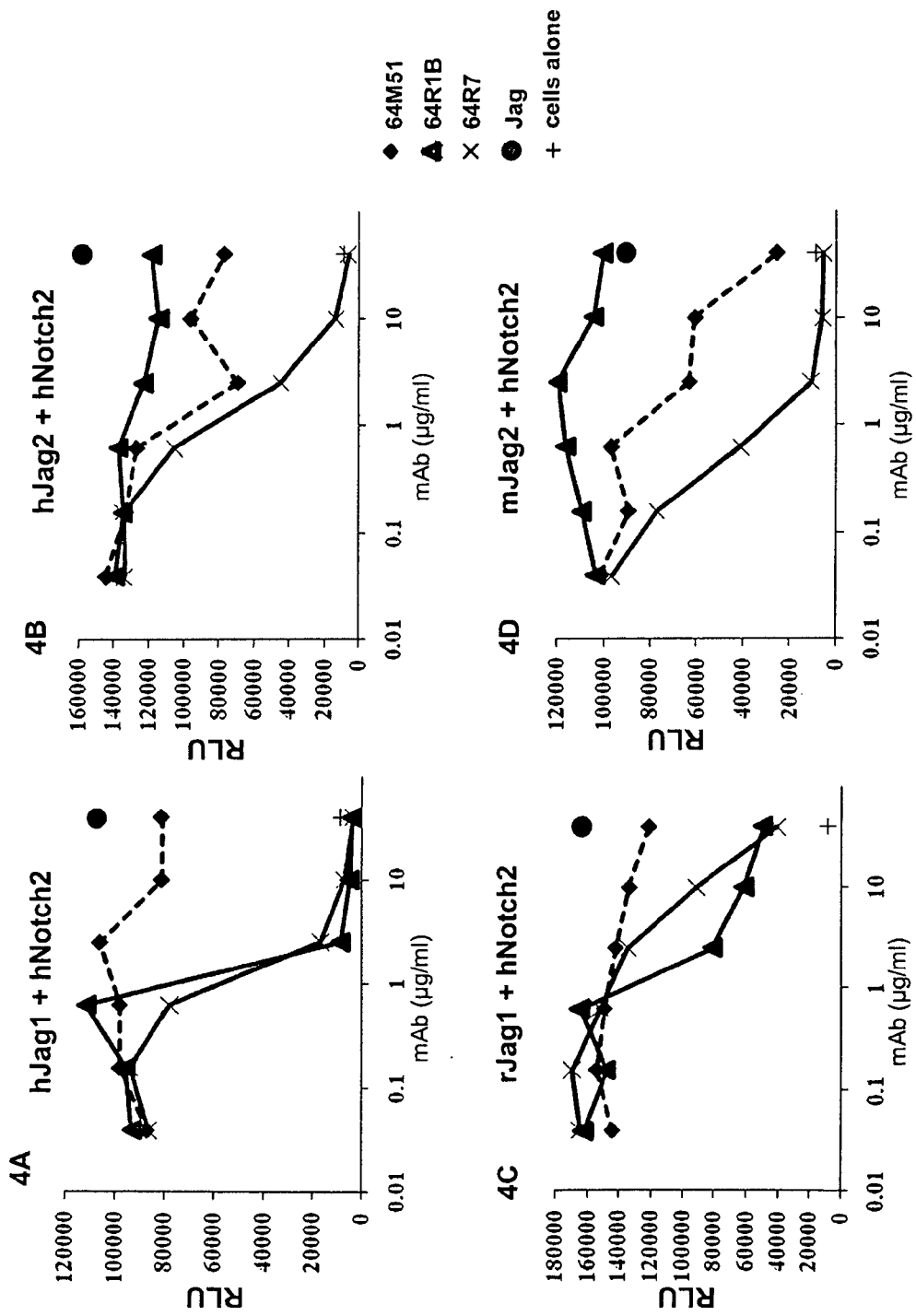

FIG. 4. Identification of antibodies that inhibit Notch activation in vitro. Human PC3 cells were transfected with a plasmid expressing a Notch2 receptor as well as plasmids encoding a Notch-dependent firefly luciferase reporter construct and a transfection control reporter (Renilla luciferase). Cells were incubated overnight in the presence of recombinant Jagged proteins and antibodies 64M51, 64R1B or 64R7. Luciferase activity (RLU) was determined using a dual luciferase assay kit. FIG. 4A shows human Jagged1 (hJag1), FIG. 4B shows human Jagged2 (hJag2), FIG. 4C shows rat Jagged1 (rJag1), and FIG. 4D shows mouse Jagged2 (mJag2). In FIGS. 4A-4D 64M51 antibody is ♦, 64R1B antibody is ▲, 64R7 antibody is x, Jag control is ● and cells alone control is +.

Figure 5:
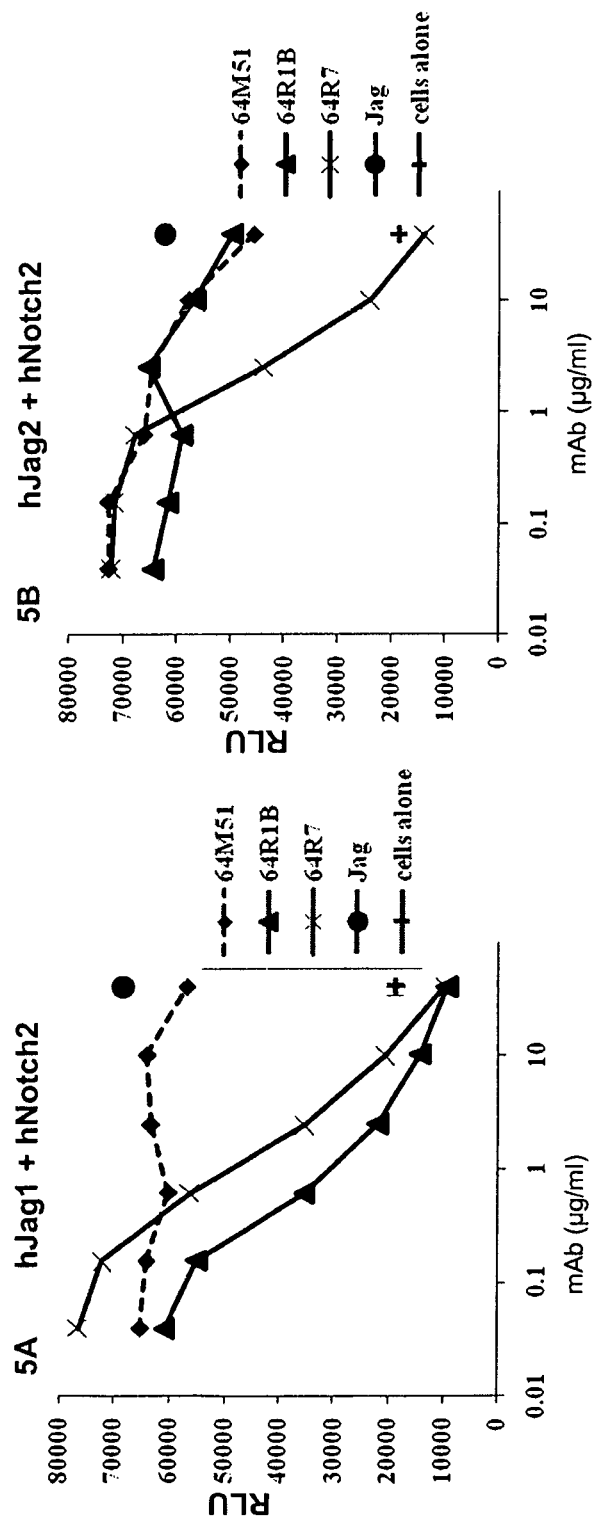

FIG. 5. Identification of antibodies that inhibit Notch activation in vitro. Human PC3 cells were transfected with a plasmid expressing a Notch2 receptor as well as plasmids encoding a Notch-dependent firefly luciferase reporter construct and a transfection control reporter (Renilla luciferase). A second set of human PC3 cells was transfected with a plasmid expressing either human Jagged 1 or human Jagged2. Aliquots of each cell population were mixed together and incubated overnight in the presence of antibody 64M51, 64R1B or 64R7. Luciferase activity (RLU) was determined using a dual luciferase assay kit. FIG. 5A shows human Jagged1 (hJag1) and FIG. 5B shows human Jagged2 (hJag2). In all figures 64M51 antibody is ♦, 64R1B antibody is ▲, 64R7 antibody is x, Jag control is ● and cells alone control is +.

Figure 6:
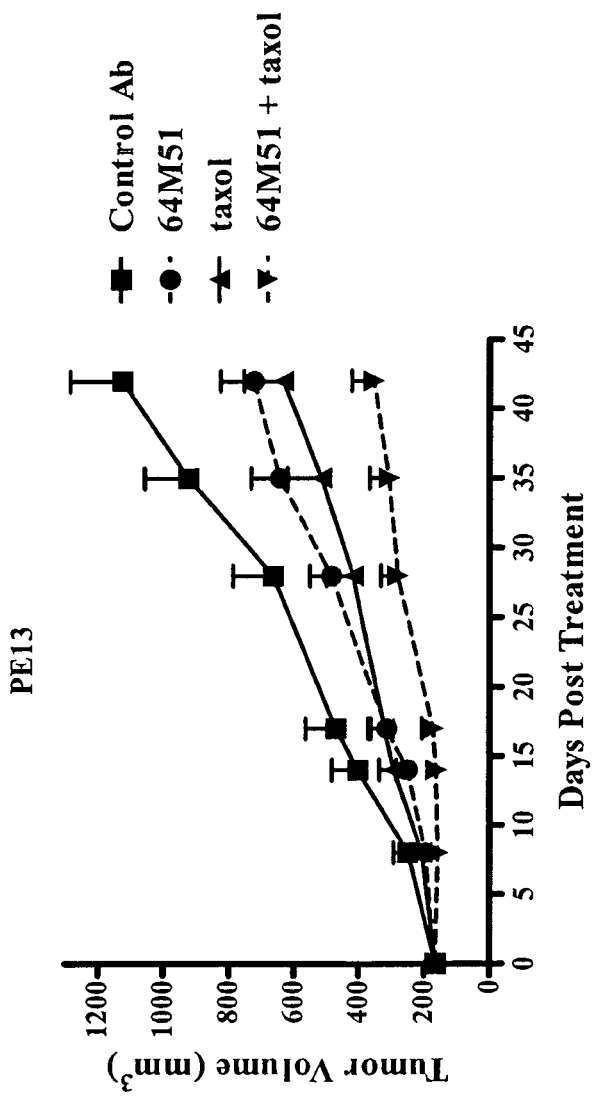

FIG. 6. Inhibition of tumor growth with antibody 64M51 and paclitaxel. PE13 breast tumor cells were injected subcutaneously into NOD/SCID mice. Mice were treated with 64M51 (●), paclitaxel (▲), 64M51+ paclitaxel (♥), or a control antibody (■). Data is shown as tumor volume (mm$^3$) over days post-treatment.

Figure 7:
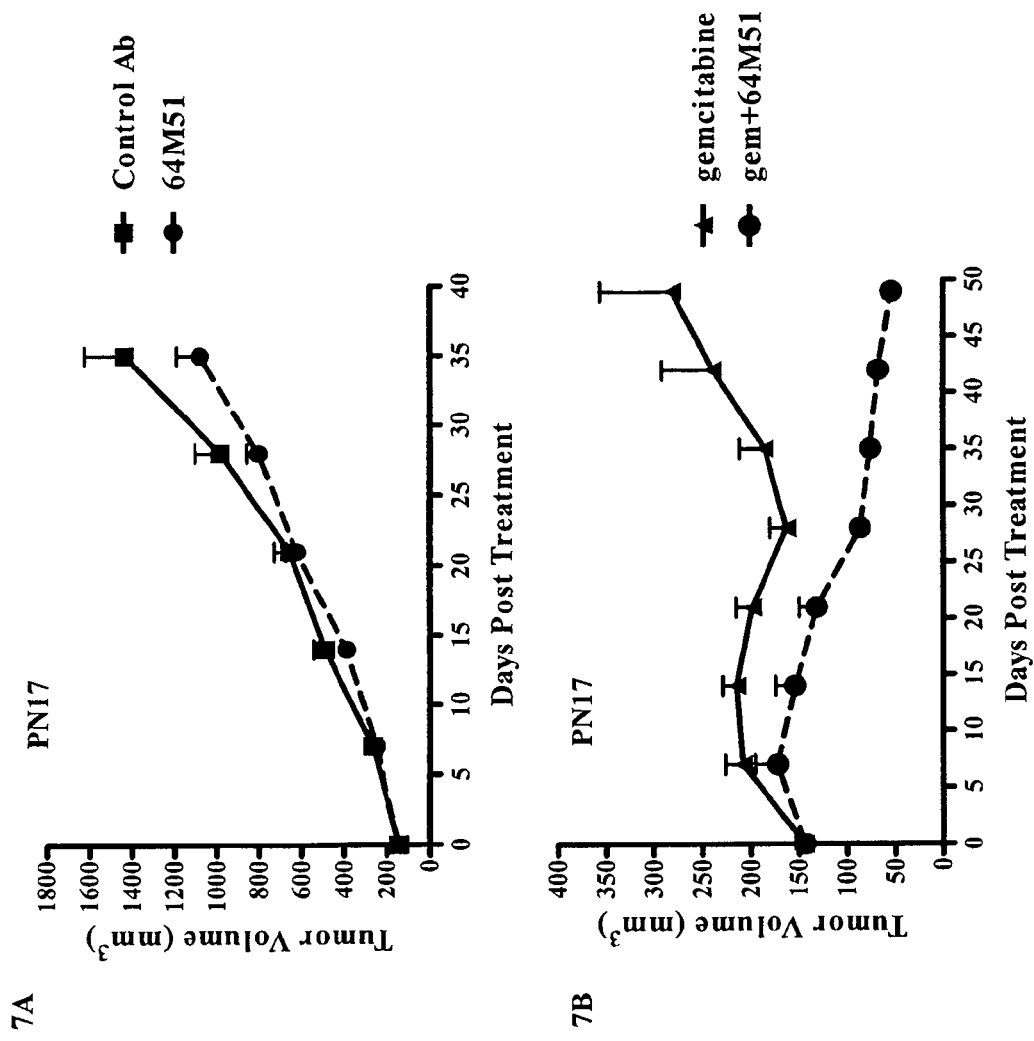

FIG. 7. Inhibition of tumor growth with antibody 64M51 and gemcitabine. PN17 pancreatic tumor cells were injected subcutaneously into NOD/SCID mice. Mice were treated with 64M51 (●) or control antibody (■) in FIG. 7A and gemcitabine (▲) or 64M51+ gemcitabine (●) in FIG. 7B. Data is shown as tumor volume (mm$^3$) over days post-treatment.

Figure 8:
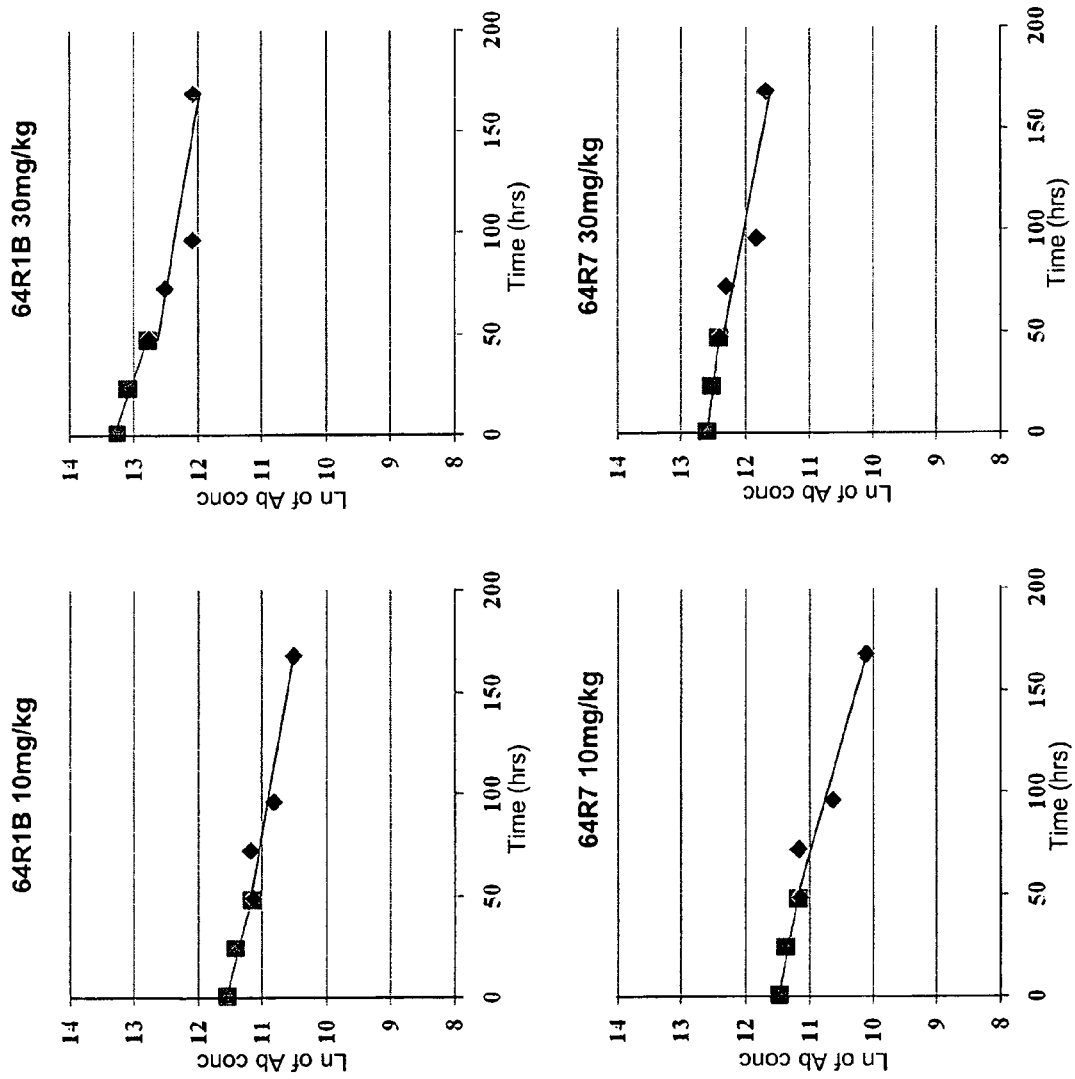

FIG. 8. Pharmacokinetics studies with antibodies 64R1B and 64R7 in rats.

Figure 9:
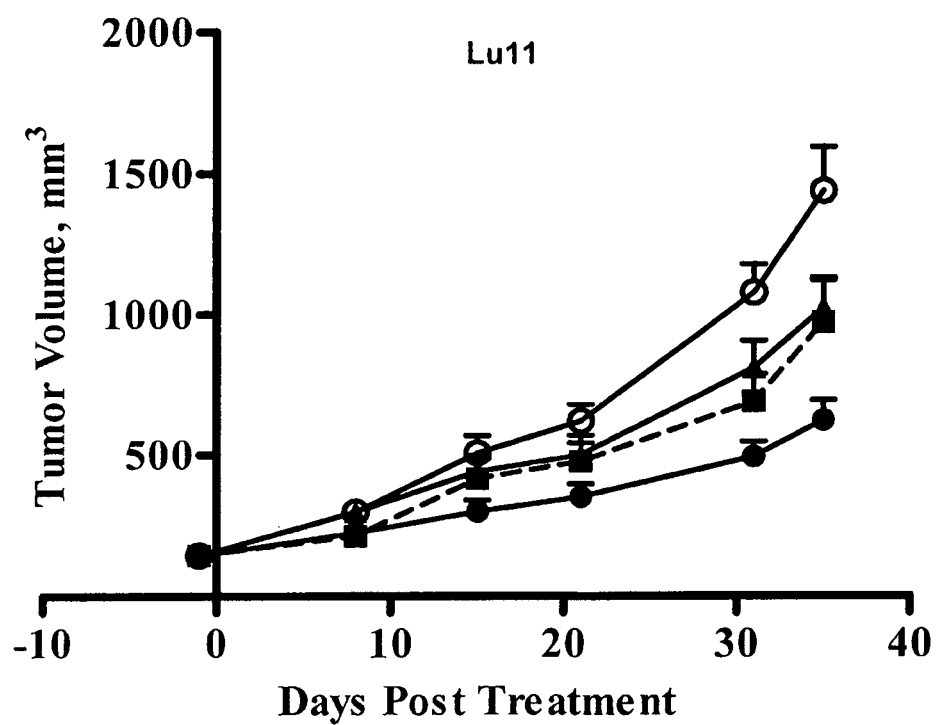

FIG. 9. Inhibition of tumor growth with antibody 64R7 and taxol. Lu11 lung tumor cells were injected subcutaneously into NOD/SCID mice. Mice were treated with 64R7 (▲), taxol (■), a combination of 64R7 and taxol (●), or control antibody (○). Data is shown as tumor volume (mm$^3$) over days post-treatment.

Figure 10:
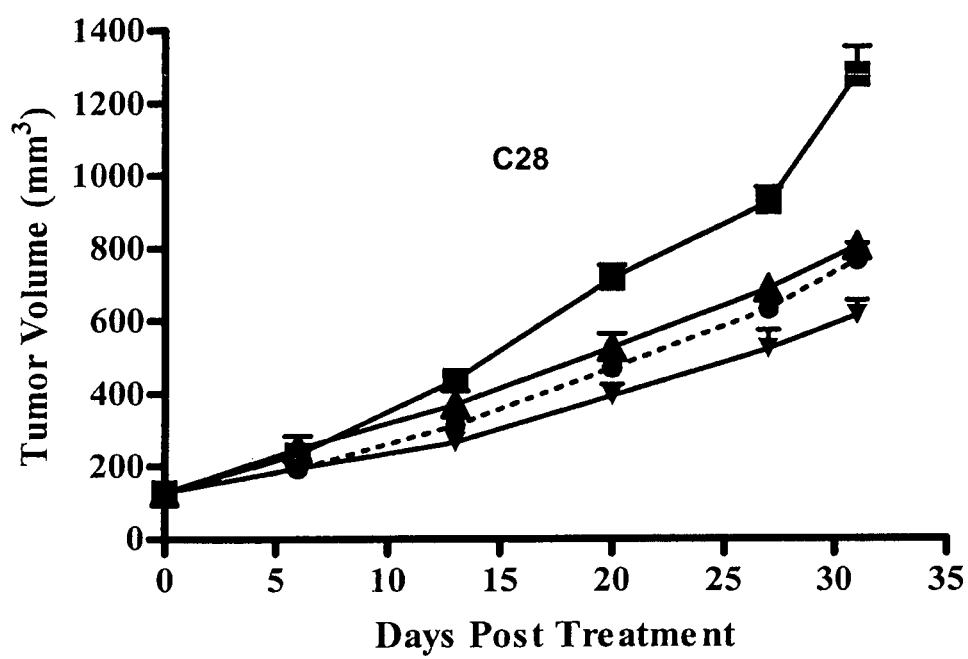

FIG. 10. Inhibition of tumor growth with antibody 64R7 and irinotecan. C28 colon tumor cells were injected subcutaneously into NOD/SCID mice. Mice were treated with 64R7 (▲), irinotecan (●), a combination of 64R7 and ininotecan (▼), or control antibody (■). Data is shown as tumor volume (mm$^3$) over days post-treatment.

Figure 11:
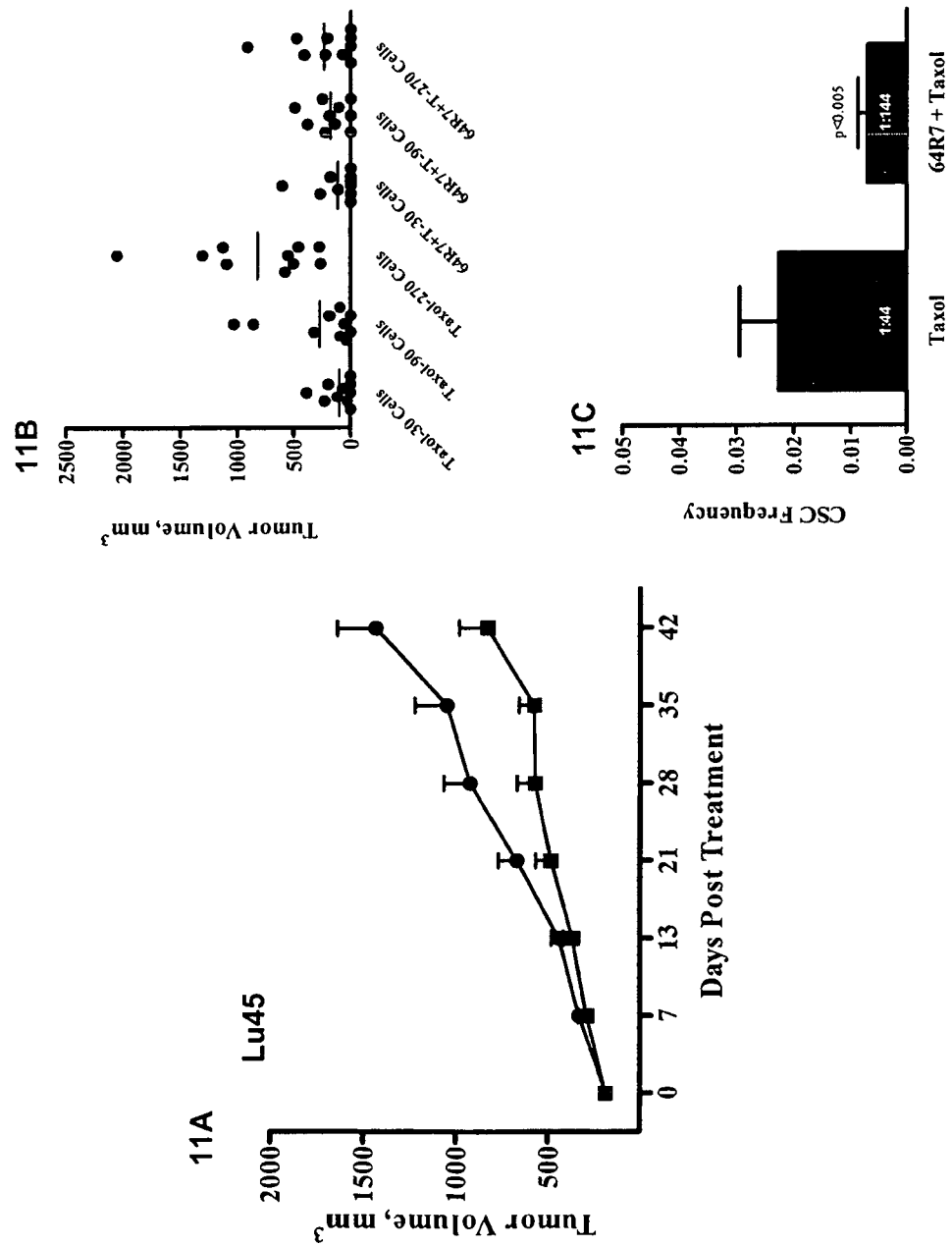

FIG. 11. Inhibition of tumor growth with antibody 64R7 and taxol. Lu45 lung tumor cells were injected subcutaneously into NOD/SCID mice. Mice were treated with taxol (●), or a combination of 64R7 and taxol (■). Data is shown as tumor volume (mm$^3$) over days post-treatment (FIG. 11A). Cells from harvested tumors were used in a limiting dilution assay (LDA). Cancer stem cell frequency in Lu45 tumors was determined following treatment with taxol or a combination of antibody 64R7 and taxol using a limiting dilution analysis (FIGS. 11B and 11C.)

Figure 12:
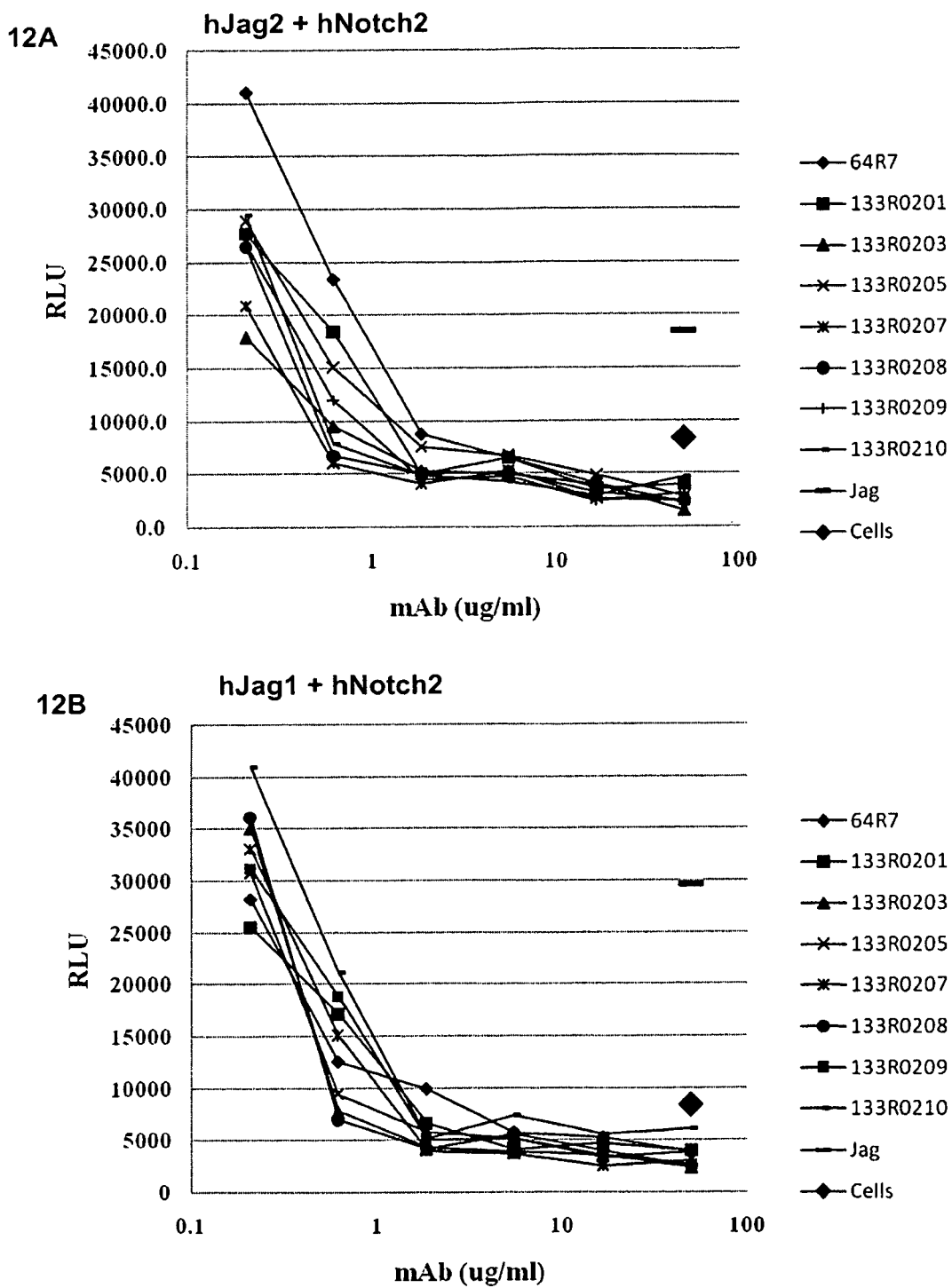

FIG. 12. Identification of anti-Jagged antibodies that inhibit Notch activation in vitro. Human PC3 cells were transfected with a plasmid expressing a Notch2 receptor as well as plasmids encoding a Notch-dependent firefly luciferase reporter construct and a transfection control reporter (Renilla luciferase). A second set of human PC3 cells was transfected with a plasmid expressing either human Jagged1 or human Jagged2. Aliquots of each cell population were mixed together and incubated overnight in the presence of anti-Jagged antibodies. Luciferase activity (RLU) was determined using a dual luciferase assay kit. FIG. 12A shows human Jagged2 (hJag2) and FIG. 12B shows human Jagged1 (hJag1).

Figure 13:
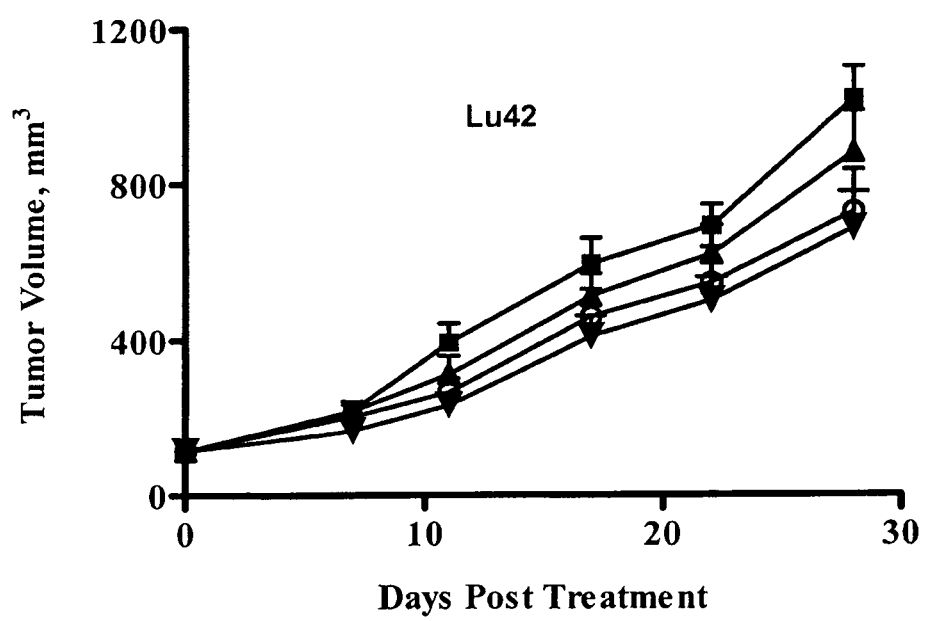

FIG. 13. Inhibition of tumor growth with antibodies 64R7, 133R0203 or 133R0205. Lu42 lung tumor cells were injected subcutaneously into NOD/SCID mice. Mice were treated with 64R7 (▲), 133R0203 (○), 133R0205 (▼) or control antibody (■). Data is shown as tumor volume (mm$^3$) over days post-treatment.

Figure 14:
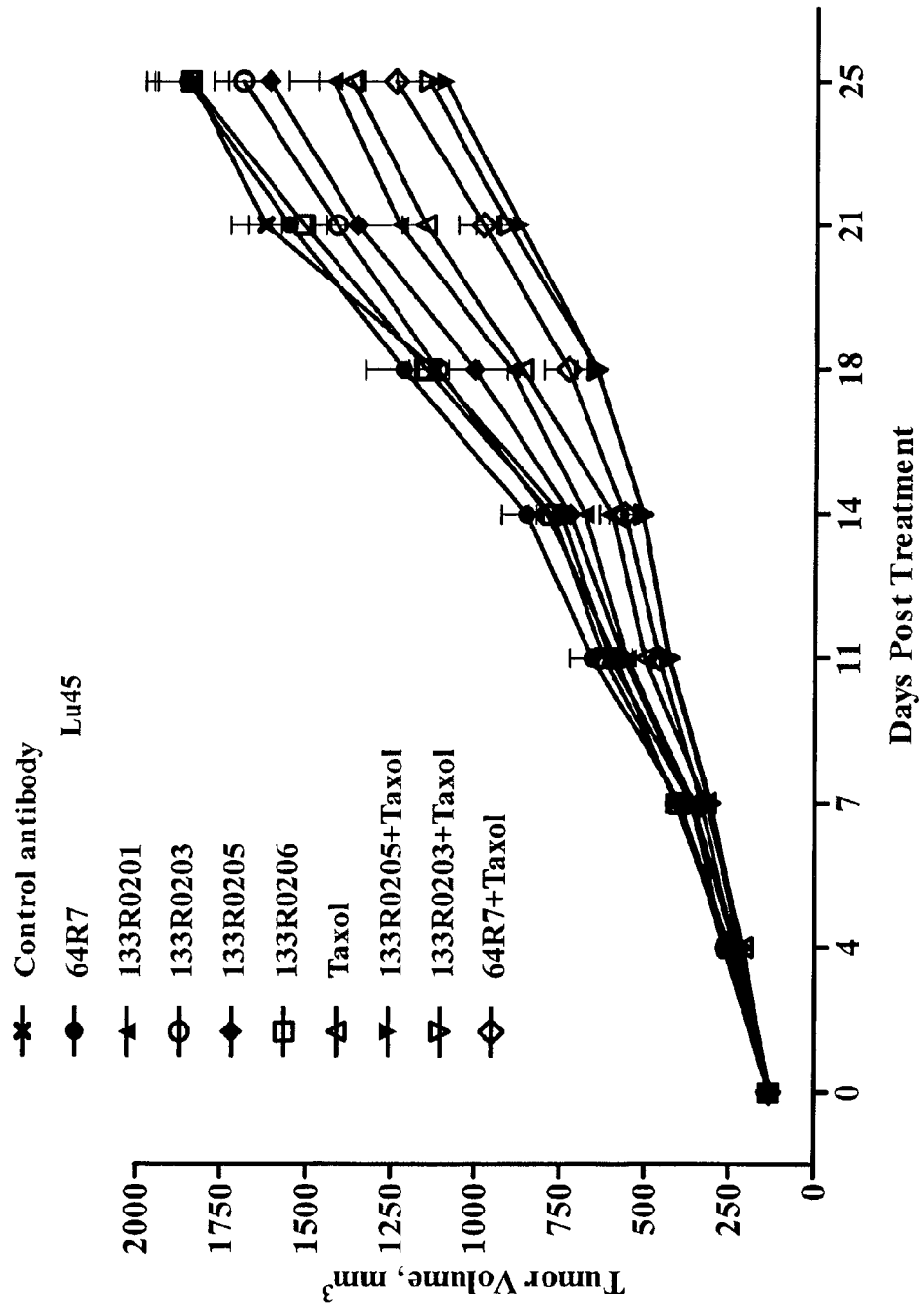

FIG. 14. Inhibition of tumor growth with anti-Jagged antibodies. Lu45 lung tumor cells were injected subcutaneously into NOD/SCID mice. Mice were treated with 64R7 (●), 133R0201 (▲), 133R0203 (○), 133R0205 (♦), 133R0206 (□), taxol (△), a combination of antibody 64R7 and taxol (◇), a combination of antibody 133R0203 and taxol (▽), a combination of antibody 133R0205 and taxol (▼) or control antibody (X). Data is shown as tumor volume (mm$^3$) over days post-treatment.

DETAILED DESCRIPTION OF THE INVENTION

The present invention provides novel agents, including, but not limited to polypeptides such as antibodies, that bind one or more Jagged proteins. The Jagged-binding agents include antagonists of the Notch signaling pathway. Related polypeptides and polynucleotides, compositions comprising the Jagged-binding agents, and methods of making the Jagged-binding agents are also provided. Methods of using the novel Jagged-binding agents, such as methods of inhibiting tumor growth, methods of treating cancer, methods of reducing the frequency of cancer stem cells in a tumor, and/or methods of inhibiting angiogenesis, are further provided.

Monoclonal antibodies that specifically bind to an extracellular domain of a Jagged, including the monoclonal antibodies 64M51, 64R7 and 64R1B, have been identified (Examples 1 and 2). Additional antibodies 133R0201, 133R0203, 133R0205, 133R0206, 133R0207, 133R0208, 133R0209, and 133R0210 have been identified (Example 13). Several of the antibodies have different binding patterns and/or different binding affinities to human Jagged1, human Jagged2, mouse Jagged1 and mouse Jagged2 (Examples 3 and 4). The antibodies 64M51, 64R7 and 64R1B appear to bind to different epitopes on human Jagged1 (Example 5). Several of the antibodies, including 64R7, 64R1B, 133R0201, 133R0203, 133R0205, 133R0207, 133R0208, 133R0209, and 133R0210 inhibit Jagged-induced Notch activation/signaling (Examples 6 and 14). Antibody 64M51 has been found to inhibit tumor cell growth in vivo in several xenograft models (Examples 7 and 8). Antibody 64R7 has been found to inhibit tumor cell growth in vivo in several xenograft models both as a single agent and in combination with chemotherapeutic agents (Examples 10, 11 and 12). In addition, antibody 64R7 has been found to reduce the frequency of cancer stem cells in a xenograft model (Example 12). Antibodies 133R0201 and 133R0203 have been found to reduce tumor cell growth in vivo in several xenograft models either as a single agent and/or in combination with chemotherapeutic agents (Examples 15 and 16).

I. Definitions

To facilitate an understanding of the present invention, a number of terms and phrases are defined below.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site or antigen-binding site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen recognition site of an antibody, and any other modified immunoglobulin molecule comprising an antigen recognition site so long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy chain constant domains referred to as alpha, delta, epsilon, gamma, and mu, respectively. The different classes of immunoglobulins have different and well-known subunit structures and three-dimensional configurations. Antibodies can be naked or conjugated to other molecules including, but not limited to, toxins and radioisotopes.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

The term "variable region" of an antibody refers to the variable region of the antibody light chain or the variable region of the antibody heavy chain, either alone or in combination. The variable regions of the heavy and light chains each consist of four framework regions (FR) connected by three complementarity determining regions (CDRs) also known as "hypervariable regions", The CDRs in each chain are held together in close proximity by the FRs and, with the CDRs from the other chain, contribute to the formation of the antigen-binding site of the antibody. There are at least two techniques for determining CDRs: (1) an approach based on cross-species sequence variability (i.e., Kabat et al. Sequences of Proteins of Immunological Interest, 5th ed., 1991, National Institutes of Health, Bethesda Md.); and (2) an approach based on crystallographic studies of antigen-antibody complexes (Al-Lazikani et al., 1997, *J. Molec. Biol.* 273:927-948). In addition, combinations of these two approaches are sometimes used in the art to determine CDRs.

The term "monoclonal antibody" refers to a homogeneous antibody population involved in the highly specific recognition and binding of a single antigenic determinant, or epitope. This is in contrast to polyclonal antibodies that typically include a mixture of different antibodies directed against different antigenic determinants. The term "monoclonal antibody" encompasses both intact and full-length monoclonal antibodies as well as antibody fragments (such as Fab, Fab', F(ab')2, Fv fragments), single chain Fv (scFv) mutants, fusion proteins comprising an antibody portion, and any other modified immunoglobulin molecule comprising an antigen recognition site. Furthermore, "monoclonal antibody" refers to such antibodies generated in any number of techniques including, but not limited to, by hybridoma production, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammal (e.g., mouse, rat, rabbit, etc.) with the desired specificity, affinity, and/or capability while the constant regions are homologous to the sequences in antibodies derived from another species (usually human) to avoid eliciting an immune response in that species.

The terms "epitope" or "antigenic determinant" are used interchangeably herein and refer to that portion of an antigen capable of being recognized and specifically bound by a particular antibody. When the antigen is a polypeptide, epitopes can be formed both from contiguous amino acids (often referred to as "linear epitopes") and noncontiguous amino acids juxtaposed by tertiary folding of a protein (often referred to as "conformation epitopes"). Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

The terms "specifically binds" and "specific binding" mean that a binding agent or an antibody reacts or associates more frequently, more rapidly, with greater duration, with greater affinity, or with some combination of the above to an epitope or protein than with alternative substances, including unrelated proteins. In certain embodiments, "specifically binds" means, for instance, that an antibody binds to a protein with a $K_D$ of about 0.1 mM or less, but more usually less than about 1 µM. In certain embodiments, "specifically binds" means that an antibody binds to a protein at times with a $K_D$ of at least about 0.1 µM or less, and at other times at least about 0.01 µM or less. Because of the sequence identity between homologous proteins in different species, specific binding can include an antibody that recognizes a particular protein such as a Jagged in more than one species (e.g., mouse Jagged1 and human Jagged1). Likewise, because of homology between different Jagged proteins in certain regions of the polypeptide sequences of the proteins, specific binding can include an antibody (or other polypeptide or agent) that recognizes more than one Jagged protein (e.g., human Jagged1 and human Jagged2). It is understood that an antibody or binding moiety that specifically binds to a first target may or may not specifically bind to a second target. As such, "specific binding" does not necessarily require (although it can include) exclusive binding, i.e. binding to a single target. Thus, an antibody may, in certain embodiments, specifically bind to more than one target (e.g., human Jagged1, human Jagged2, mouse Jagged 1, and/or mouse Jagged2). In certain embodiments, the multiple targets may be bound by the same antigen-binding site on the antibody. For example, an antibody may, in certain instances, comprise two identical antigen-binding sites, each of which specifically binds the same epitope on two or more Jagged proteins (e.g., Jagged1 and/or Jagged2). In certain alternative embodiments, an antibody may be bispecific or multispecific and comprise at least two antigen-binding sites with differing specificities. By way of non-limiting example, a bispecific antibody may comprise one antigen-binding site that recognizes an epitope on one Jagged protein, such as human Jagged1, and further comprises a second, different antigen-binding site that recognizes a different epitope on a second Jagged protein, such as human Jagged2. Generally, but not necessarily, reference to binding means specific binding.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "polynucleotide" and "nucleic acid," are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps"; substitution of one or more of the naturally occurring nucleotides with an analog; internucleotide modifications such as uncharged linkages (e.g., methyl phosphonates, phosphotriesters, phosphoamidates, cabarmates, etc.) and charged linkages (e.g., phosphorothioates, phosphorodithioates, etc.); pendant moieties, such as proteins (e.g., nucleases, toxins, antibodies, signal peptides, poly-L-lysine, etc.); intercalators (e.g., acridine, psoralen, etc.); chelators (e.g., metals, radioactive metals, boron, oxidative metals, etc.); alkylators; modified linkages (e.g., alpha anomeric nucleic acids, etc.); as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, heptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or a substituted or unsubstituted alkyl (1-20 C) optionally containing an ether (—O—) linkage, aryl, alkenyl, cycloalkyl, cycloalkenyl or araldyl. Not all linkages in a polynucleotide need be identical.

"Conditions of high stringency" may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software are known in the art that may be used to obtain alignments of amino acid or nucleotide sequences. These include but are not limited to, BLAST, ALIGN, Megalign, BestFit, etc. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues in length or any integral value therebetween. In some embodiments, identity exists over a longer region than 60-80 residues, such as at least about 90-10.0 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen(s), i.e., the one or more Jagged proteins to which the polypeptide or antibody binds. Methods of identifying nucleotide and amino acid conservative substitutions which do not eliminate antigen binding are well-known in the art.

The term "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, and DNA or RNA expression vectors encapsulated in liposomes.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), more preferably at least 90% pure, more preferably at least 95% pure, more preferably at least 98% pure, more preferably at least 99% pure.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, melanoma, vulval cancer, thyroid cancer, hepatic carcinoma and various types of head and neck cancers.

The terms "tumor" and "neoplasm" refer to any mass of tissue that results from excessive cell growth or proliferation, either benign (noncancerous) or malignant (cancerous), including pre-cancerous lesions.

The terms "cancer stem cell" and "CSC" and "tumor stem cell" and "solid tumor stem cell" and "tumorigenic stem cell" are used interchangeably herein and refer to a population of cells from a solid tumor that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. These properties confer on the "cancer stem cells" the ability to form palpable tumors upon serial transplantation into an immunocompromised host (e.g., a mouse) compared to the majority of tumor cells that fail to form tumors. Cancer stem cells undergo self-renewal versus differentiation in a chaotic manner to form tumors with abnormal cell types that can change over time as mutations occur.

The terms "cancer cell" and "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor. These properties of self-renewal and proliferation to generate all other tumor cells confer on cancer stem cells the ability to form palpable tumors upon serial transplantation into an immunocompromised host (e.g., a mouse) compared to non-tumorigenic tumor cells, which are unable to form tumors upon serial transplantation. It has been observed that non-tumorigenic tumor cells may form a tumor upon primary transplantation into an immunocompromised host after obtaining the tumor cells from a solid tumor, but those non-tumorigenic tumor cells do not give rise to a tumor upon serial transplantation.

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The phrase "pharmaceutically acceptable salt" refers to a salt of a compound that is pharmaceutically acceptable and that possesses the desired pharmacological activity of the parent compound.

The phrase "pharmaceutically acceptable excipient, carrier or adjuvant" refers to an excipient, carrier or adjuvant that can be administered to a subject, together with at least one binding agent or antibody of the present disclosure, and which does not destroy the pharmacological and/or biological activity thereof and is nontoxic when administered in doses sufficient to deliver a therapeutic amount of the binding agent.

The phrase "pharmaceutically acceptable vehicle" refers to a diluent, adjuvant, excipient, or carrier with which at least one binding agent or antibody of the present disclosure is administered.

The phrase "therapeutically effective amount" refers to an amount of a binding agent, antibody, polypeptide, polynucleotide, small organic molecule, or other drug effective to "treat" a disease or disorder in a subject or mammal. In the case of cancer, the therapeutically effective amount of the drug (e.g., an antibody) can reduce the number of cancer cells; reduce the tumor size; inhibit and/or stop cancer cell infiltration into peripheral organs including, for example, the spread of cancer into soft tissue and bone; inhibit and/or stop tumor metastasis; inhibit and/or stop tumor growth; relieve to some extent one or more of the symptoms associated with the cancer; reduce morbidity and mortality; improve quality of life; decrease tumorigenicity, tumorigenic frequency, or tumorigenic capacity of a tumor; reduce the number or frequency of cancer stem cells in a tumor; differentiate tumorigenic cells to a non-tumorigenic state; or a combination of such effects. To the extent the drug prevents growth and/or kills existing cancer cells, it can be referred to as cytostatic and/or cytotoxic.

The terms "treating" and "treatment" and "to treat" and "alleviating" and "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: a reduction in the number of, or complete absence of, cancer cells; a reduction in the tumor size; inhibition of, or an absence of, cancer cell infiltration into peripheral organs including, for example, the spread of cancer into soft tissue and bone; inhibition of, or an absence of, tumor metastasis; inhibition of, or an absence of, tumor growth; relief of one or more symptoms associated with the specific cancer; reduced morbidity and mortality; improvement in quality of life; reduction in tumorigenicity, tumorigenic frequency, or tumorigenic capacity of a tumor; reduction in the number or frequency of cancer stem cells in a tumor; differentiation of tumorigenic cells to a non-tumorigenic state; or some combination of effects.

As used in the present disclosure and claims, the singular forms "a" "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided.

The term "and/or" as used in a phrase such as "A and/or B" herein is intended to include each of the following embodiments: A and B; A or B; A (alone) and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Jagged-Binding Agents

The present invention provides agents that specifically bind. Jagged (e.g., Jagged1 and/or Jagged2). These agents are referred to herein as "Jagged-binding agents". In certain embodiments, the agents bind Jagged1. In certain embodiments, the agents bind Jagged2. In certain embodiments, the agents bind both Jagged1 and Jagged2. In certain embodiments, the Jagged is human Jagged1 (hTagged1) and/or human Jagged2 (hJagged2). The full-length amino acid (aa) sequences for human Jagged1 and human Jagged2 are known in the art and are provided herein as SEQ ID NO:43 (hJagged1 aa) and SEQ ID NO:44 (hJagged2 aa). In both sequences, the signal sequence and extracellular domain (ECD) are underlined.

In certain embodiments, the Jagged-binding agent is an antibody that specifically binds to Jagged1. In certain embodiments, the Jagged-binding agent is an antibody that specifically binds to Jagged2. In some embodiments, the Jagged-binding agent is an antibody that specifically binds to both Jagged1 and Jagged2. In certain embodiments, the Jagged1 is human Jagged1. In certain embodiments, the Jagged2 is human Jagged2. In some embodiments, the Jagged1 is mouse Jagged1. In certain embodiments, the Jagged2 is mouse Jagged2. In certain embodiments, the Jagged-binding agent (e.g., an antibody) binds human Jagged1 and mouse Jagged1. In certain embodiments, the Jagged-binding agent (e.g., an antibody) binds human Jagged1, human Jagged2, mouse Jagged1 and mouse Jagged2. In some embodiments, the Jagged-binding agent (e.g., an antibody) does not bind mouse Jagged1 and/or mouse Jagged2.

In certain embodiments, the Jagged-binding agent (e.g., an antibody) specifically binds to an extracellular domain (ECD) of Jagged. In some embodiments, the Jagged-binding agent (e.g., an antibody) binds to a region comprising the DSL domain of an extracellular domain of a Jagged protein. In some embodiments, the Jagged-binding agent (e.g., an antibody) binds to a region comprising an EGF domain of an extracellular domain of a Jagged protein. In some embodiments, the Jagged-binding agent (e.g., an antibody) binds to a region comprising an EGF1, EGF2, and/or EGF3 domain of an extracellular domain of a Jagged protein.

In certain embodiments, the Jagged-binding agent (e.g., an antibody) binds to an extracellular domain of Jagged with a dissociation constant ($K_D$) of about 1 µM or less, about 100 nM or less, about 40 nM or less, about 20 nM or less, about 10 nM or less or about 1 nM or less. In certain embodiments, the Jagged-binding agent (e.g., an antibody) binds to human Jagged1 with a $K_D$ of about 40 nM or less, about 20 nM or less, about 10 nM or less, or about 1 nM or less. In certain embodiments, the Jagged-binding agent (e.g., an antibody) binds to human Jagged2 with a $K_D$ of about 40 nM or less, about 20 nM or less, about 10 nM or less, or about 1 nM or less. In certain embodiments, the Jagged-binding agent (e.g., an antibody) binds to both human Jagged1 and human Jagged2 with a $K_D$ of about 40 nM or less, about 20 nM or less, about 10 nM or less, or about 1 nM or less. In some embodiments, the dissociation constant of the binding agent (e.g., an antibody) to a particular Jagged is the dissociation constant determined using a Jagged fusion protein comprising a Jagged extracellular domain (e.g., a Jagged1 ECD-Fc fusion protein) immobilized on a Biacore chip.

In some embodiments, the Jagged-binding agent (e.g., an antibody) of the invention as described herein binds to an extracellular domain of Jagged1 with a $K_D$ of 50 nM or less and binds to an extracellular domain of Jagged2 with a $K_D$ of 50 nM or less. In some embodiments, the Jagged-binding agent (e.g., an antibody) binds to an extracellular domain of Jagged1 with a $K_D$ of 10 nM or less and binds to an extracellular domain of Jagged2 with a $K_D$ of 10 nM or less. In some embodiments, the Jagged-binding agent (e.g., an antibody) binds to an extracellular domain of Jagged1 with a $K_D$ of 50 nM or less and binds to an extracellular domain of Jagged2 with a $K_D$ of 10 nM or less. In some embodiments, the Jagged-binding agent (e.g., an antibody) binds to an extracellular domain of Jagged1 with a $K_D$ of 10 nM or less and binds to an extracellular domain of Jagged2 with a $K_D$ of 50 nM or less. In some embodiments, the Jagged-binding agent (e.g., an antibody) binds to an extracellular domain of Jagged1 with a $K_D$ of 10 nM or less and binds to Jagged2 at undetectable levels. In some embodiments, the Jagged-binding agent (e.g., an antibody) binds to an extracellular domain of Jagged2 with a $K_D$ of 10 nM or less and binds to Jagged1 at undetectable levels.

In certain embodiments, the Jagged-binding agent (e.g., an antibody) binds to Jagged with a half maximal effective concentration ($EC_{50}$) of about 1 µM or less, about 100 nM or less, about 40 nM or less, about 20 nM or less, about 10 nM or less, or about 1 nM or less. In certain embodiments, the Jagged-binding agent (e.g., an antibody) binds to human Jagged1 with an $EC_{50}$ of about 40 nM or less, about 20 nM or less, about 10 nM or less, or about 1 nM or less. In certain embodiments, the Jagged-binding agent (e.g., an antibody) binds to human Jagged2 with an $EC_{50}$ of about 40 nM or less, about 20 nM or less, about 10 nM or less, or about 1 nM or less. In certain embodiments, the Jagged-binding agent (e.g., an antibody) binds to both human Jagged1 and human Jagged2 with an $EC_{50}$ of about 40 nM or less, about 20 nM or less, about 10 nM or less, or about 1 nM or less.

In certain embodiments, the Jagged-binding agent is a polypeptide. In certain embodiments, the Jagged-binding agent or polypeptide is an antibody. In certain embodiments, the antibody is an IgG antibody. In some embodiments, the antibody is an IgG1 antibody. In some embodiments, the antibody is an IgG2 antibody. In certain embodiments, the antibody is a monoclonal antibody. In certain embodiments, the antibody is a humanized antibody. In certain embodiments, the antibody is a human antibody. In certain embodiments, the antibody is an antibody fragment.

In certain embodiments, the Jagged-binding agents and polypeptides as described herein have a half-life of at least about 50 hours in a rat when administered via the tail vein at a dose ranging from about 2 mg/kg to about 30 mg/kg. In certain embodiments, the Jagged-binding agent or polypeptide has a half-life of at least about 50 hours in a rat when administered via the tail vein at a dose of about 10 mg/kg to about 30 mg/kg. In certain embodiments, the Jagged-binding agent or polypeptide has a half-life of at least about 50 hours in a rat when administered via the tail vein at a dose of about 10 mg/kg. In certain embodiments, the Jagged-binding agent or polypeptide has a half-life of at least about 100 hours in a rat when administered via the tail vein at a dose ranging from about 2 mg/kg to about 30 mg/kg. In certain embodiments, the Jagged-binding agent or polypeptide has a half-life of at least about 100 hours in a rat when administered via the tail vein at a dose of about 10 mg/kg to about 30 mg/kg. In certain embodiments, the Jagged-binding agent or polypeptide has a half-life of at least about 100 hours in a rat when administered via the tail vein at a dose of about 30 mg/kg.

The Jagged-binding agents (e.g., antibodies) of the present invention can be assayed for specific binding by any method known in the art. The immunoassays which can be used include, but are not limited to, competitive and non-competitive assay systems using techniques such as Biacore analysis, FACS analysis, immunofluorescence, immunocytochemistry, Western blot analysis, radioimmunoassay, ELISA, "sandwich" immunoassay, immunoprecipitation assay, precipitation reaction, gel diffusion precipitin reaction, immunodiffusion assay, agglutination assay, complement-fixation assay, immunoradiometric assay, fluorescent immunoassay, and protein A immunoassay. Such assays are routine and well known in the art (see, e.g., Ausubel et al., eds, 1994, Current Protocols in Molecular Biology, Vol. 1, John Wiley & Sons, Inc., New York).

In some embodiments, the specific binding of a Jagged-binding agent (e.g., an antibody) to a human Jagged may be determined using ELISA. An ELISA assay comprises preparing Jagged antigen, coating wells of a 96 well microtiter plate with antigen, adding to the wells the Jagged-binding agent or antibody conjugated to a detectable compound such as an enzymatic substrate (e.g., horseradish peroxidase or alkaline phosphatase), incubating for a period of time and detecting the presence of the binding agent or antibody. In some embodiments, the Jagged-binding agent (e.g., an antibody) is not conjugated to a detectable compound, but instead a second conjugated antibody that recognizes the Jagged-binding agent (e.g., an antibody) is added to the well. In some embodiments, instead of coating the well with the Jagged antigen, the Jagged-binding agent (e.g., an antibody) can be coated to the well, antigen is added to the coated well and then a second antibody conjugated to a detectable compound is added. One of skill in the art would be knowledgeable as to the parameters that can be modified and/or optimized to increase the signal detected, as well as other variations of ELISAs that can be used (see e.g., Ausubel et al., eds, 1994, Current Protocols in Molecular Biology, Vol. 1, John Wiley & Sons, Inc., New York at 11.2.1).

The binding affinity of an antibody or other binding agent to Jagged and the on-off rate of an antibody-antigen interaction can be determined by competitive binding assays. In some embodiments, a competitive binding assay is a radio-immunoassay comprising the incubation of labeled antigen (e.g., $^3$H- or $^{125}$I-labeled antigen), or fragment or variant thereof, with the antibody of interest in the presence of increasing amounts of unlabeled antigen followed by the detection of the antibody bound to the labeled antigen. The affinity of the antibody for the antigen and the on-off rates can be determined from the data by Scatchard plot analysis. In some embodiments, Biacore kinetic analysis is used to determine the binding affinities and on-off rates of antibodies or agents that bind Jagged (e.g., human Jagged1, human Jagged1, mouse Jagged1, etc.). Biacore kinetic analysis comprises analyzing the binding and dissociation of antibodies from antigens (e.g., Jagged proteins) that have been immobilized on the surface of a Biacore chip. In some embodiments, Biacore kinetic analyses can be used to study binding of different antibodies in qualitative epitope competition binding assays.

In certain embodiments, the invention provides a Jagged-binding agent (e.g, an antibody) that specifically binds to an extracellular domain of human Jagged, wherein the Jagged-binding agent (e.g, an antibody) comprises one, two, three, four, five and/or six of the CDRs of antibodies 64M51, 64R1B, 64R7, 133R0201, 133R0203 or 133R0205 (see Table 1). In some embodiments, the Jagged-binding agent comprises one or more of the CDRs of 64M51, two or more of the CDR5 of 64M511, three or more of the CDRs of 64M51, four or more of the CDRs of 64M51, five or more of the CDRs of 64M51, or all six of the CDRs or 64M51. In some embodiments, the Jagged-binding agent comprises one or more of the CDRs of 64R7, two or more of the CDRs of 64R7, three or more of the CDRs of 64R7, four or more of the CDRs of 64R7, five or more of the CDRs of 64R7, or all six of the CDRs or 64R7. In some embodiments, the Jagged-binding agent comprises one or more of the CDRs of 64R1B, two or more of the CDRs of 64R1B, three or more of the CDRs of 64R1B, four or more of the CDRs of 64R1B, five or more of the CDRs of 64R1B, or all six of the CDRs or 64R1B. In some embodiments, the Jagged-binding agent comprises one or more of the CDRs of 133R0201, two or more of the CDRs of 133R0201, three or more of the CDRs of 133R0201, four or more of the CDRs of 133R0201, five or more of the CDRs of 133R0201, or all six of the CDRs or 133R0201. In some embodiments, the Jagged-binding agent comprises one or more of the CDRs of 133R0203, two or more of the CDRs of 133R0203, three or more of the CDRs of 133R0203, four or more of the CDRs of 133R0203, five or more of the CDRs of 133R0203, or all six of the CDRs or 133R0203. In some embodiments, the Jagged-binding agent comprises one or more of the CDRs of 133R0205, two or more of the CDRs of 133R0205, three or more of the CDRs of 133R0205, four or more of the CDRs of 133R0205, five or more of the CDRs of 133R0205, or all six of the CDRs or 133R0205. In some embodiments, the Jagged-binding agent comprises CDRs with up to four (i.e., 0, 1, 2, 3, or 4) amino acid substitutions per CDR. In certain embodiments, the heavy chain CDR(s) are contained within a heavy chain variable region. In certain embodiments, the light chain CDR(s) are contained within a light chain variable region.

(SEQ ID NO:10), and a heavy chain CDR3 comprising NGGFFDY (SEQ ID NO:11). In certain embodiments, the Jagged-binding agent further comprises: a light chain CDR1 comprising RASESVDSYGNSFMH (SEQ ID NO:12), a light chain CDR2 comprising RASNLES (SEQ ID NO:13), and a light chain CDR3 comprising QQSNEDPWT (SEQ ID NO:14). In some alternative embodiments, the Jagged-binding agent comprises: a light chain CDR1 comprising RASESVDSYGNSFMH (SEQ ID NO:12), a light chain CDR2 comprising RASNLES (SEQ ID NO:13), and a light chain CDR3 comprising QQSNEDPWT (SEQ ID. NO:14). In certain embodiments, the Jagged-binding agent specifically binds human Jagged1. In certain embodiments, the Jagged-binding agent further specifically binds human Jagged2. In certain embodiments, the Jagged-binding agent specifically binds human Jagged2.

In certain embodiments, the invention provides a Jagged-binding agent (e.g, an antibody) that specifically binds to an extracellular domain of human Jagged1 and/or Jagged2, wherein the Jagged-binding agent comprises (a) a heavy chain CDR1 comprising SYWIH (SEQ ID NO:9), or a variant thereof comprising 1, 2, 3, or 4 amino acid substitutions; (b) a heavy chain CDR2 comprising RIYPGIGSTYYNEKFKD (SEQ ID NO:10), or a variant thereof comprising 1, 2, 3, or 4 amino acid substitutions; and (c) a heavy chain CDR3 com-

TABLE 1

|          | 64M51                             | 64R7                                    | 64R1B                              |
|----------|-----------------------------------|-----------------------------------------|------------------------------------|
| HC CDR1  | SYWIH (SEQ ID NO: 9)              | SYAMH (SEQ ID NO: 23)                   | SSNWWS (SEQ ID NO: 37)             |
| HC CDR2  | RIYPGIGSTYYNEKFKD (SEQ ID NO: 10) | VISYDGSNKYYADSVKG (SEQ ID NO: 24)       | EIFHGENTNYNPSLKS (SEQ ID NO: 38)   |
| HC CDR3  | NGGFFDY (SEQ ID NO: 11)           | DKYDIPDAFDI (SEQ ID NO: 25)             | NPGIGAAKFDS (SEQ ID NO: 39)        |
| LC CDR1  | RASESVDSYGNSFMH (SEQ ID NO: 12)   | RASQGISNDLA (SEQ ID NO: 26)             | KSSQSLLHSDGKTYLY (SEQ ID NO: 40)   |
| LC CDR2  | RASNLES (SEQ ID NO: 13)           | ATSTLQS (SEQ ID NO: 27)                 | EVSNRFS (SEQ ID NO: 41)            |
| LC CDR3  | QQSNDPWT (SEQ ID NO: 14)          | QQSYNAPI (SEQ ID NO: 28)                | MQHIDFP (SEQ ID NO: 42)            |
|          | 133R0201                          | 133R0203                                | 133R0205                           |
| HC CDR1  | SYAMH (SEQ ID NO: 23)             | SYAMH (SEQ ID NO: 23)                   | SYAMH (SEQ ID NO: 23)              |
| HC CDR2  | AIYPDSSNKYYADSVKG (SEQ ID NO: 47) | AISPEASNKYYADSVKG (SEQ ID NO: 48)       | AIYPASSNKYYADSVKG (SEQ ID NO: 49)  |
| HC CDR3  | DKYDIPDAFDI (SEQ ID NO: 25)       | DKYDIPDAFDI (SEQ ID NO: 25)             | DKYDIPDAFDI (SEQ ID NO: 25)        |
| LC CDR1  | RASQGISNDLA (SEQ ID NO: 26)       | RASQGISNDLA (SEQ ID NO: 26)             | RASQGISNDLA (SEQ ID NO: 26)        |
| LC CDR2  | ATSTLQS (SEQ ID NO: 27)           | ATSTLQS (SEQ ID NO: 27)                 | ATSTLQS (SEQ ID NO: 27)            |
| LC CDR3  | QQSYNAPI (SEQ ID NO: 28)          | QQSYNAPI (SEQ ID NO: 28)                | QQSYNAPI (SEQ ID NO: 28)           |

In certain embodiments, the invention provides a Jagged-binding agent (e.g., an antibody) that specifically binds to an extracellular domain of human Jagged1 and/or human Jagged2, wherein the Jagged-binding agent comprises: a heavy chain CDR1 comprising SYWIH (SEQ ID NO:9), a heavy chain CDR2 comprising RIYPGIGSTYYNEKFKD prising NGGFFDY (SEQ ID NO:11), or a variant thereof comprising 1, 2, 3, or 4 amino acid substitutions. In certain embodiments, the Jagged-binding agent further comprises (a) a light chain CDR1 comprising RASESVDSYGNSFMH (SEQ ID NO:12), or a variant thereof comprising 1, 2, 3, or 4 amino acid substitutions; (b) a light chain CDR2 comprising RASNLES (SEQ ID NO:13), or a variant thereof comprising 1, 2, 3, or 4 amino acid substitutions; and (c) a light chain CDR3 comprising QQSNEDPWT (SEQ ID NO:14), or a variant thereof comprising 1, 2, 3, or 4 amino acid substitutions. In some alternative embodiments, the Jagged-binding agent comprises (a) a light chain CDR1 comprising RASES-VDSYGNSFMH (SEQ ID NO:12), or a variant thereof comprising 1, 2, 3, or 4 amino acid substitutions; (b) a light chain CDR2 comprising RASNLES (SEQ ID NO:13), or a variant thereof comprising 1, 2, 3, or 4 amino acid substitutions; and (c) a light chain CDR3 comprising QQSNEDPWT (SEQ ID NO:14), or a variant thereof comprising 1, 2, 3, or 4 amino acid substitutions. In certain embodiments, the amino acid substitutions are conservative substitutions. In certain embodiments, the Jagged-binding agent specifically binds human Jagged1. In certain embodiments, the Jagged-binding agent further specifically binds human Jagged2. In certain embodiments, the Jagged-binding agent specifically binds human Jagged2.

In certain embodiments, the invention provides a Jagged-binding agent (e.g., an antibody) that specifically binds to an extracellular domain of human Jagged1 and/or human Jagged2, wherein the Jagged-binding agent comprises: a heavy chain CDR1 comprising, SYAMH (SEQ ID NO:23), a heavy chain CDR2 comprising VISYDGSNKYYADSVKG (SEQ ID NO:24), AIYPDSSNKYYADSVKG (SEQ ID NO:47), AISPEASNKYYADSVKG (SEQ ID NO:48), or AIYPASSNKYYADSVKG (SEQ ID NO:49), and a heavy chain CDR3 comprising DKYDIPDAFDI (SEQ ID NO:25). In certain embodiments, the Jagged-binding agent further comprises: a light chain CDR1 comprising RASQGISNDLA (SEQ ID NO:26), a light chain CDR2 comprising ATSTLQS (SEQ ID NO:27), and a light chain CDR3 comprising QQSYNAPI (SEQ ID NO:28). In some alternative embodiments, the Jagged-binding agent comprises: a light chain CDR1 comprising RASQGISNDLA (SEQ ID NO:26), a light chain CDR2 comprising ATSTLQS (SEQ ID NO:27), and a light chain CDR3 comprising QQSYNAPI (SEQ ID NO:28). In certain embodiments, the Jagged-binding agent specifically binds human Jagged1. In certain embodiments, the Jagged-binding agent further specifically binds human Jagged2. In certain embodiments, the Jagged-binding agent specifically binds human Jagged2.

In certain embodiments, the invention provides a Jagged-binding agent (e.g., an antibody) that specifically binds to an extracellular domain of human Jagged1 and/or human Jagged2, wherein the Jagged-binding agent comprises (a) a heavy chain CDR1 comprising SYAMH (SEQ ID NO:23), or a variant thereof comprising 1, 2, 3, or 4 amino acid substitutions; (b) a heavy chain CDR2 comprising VISYDGSNKYYADSVKG (SEQ. ID NO:24), AIYPDSSNKYYADSVKG (SEQ ID NO:47), AISPEASNKYYADSVKG (SEQ ID NO:48), or AIYPASSNKYYADSVKG (SEQ ID NO:49), or a variant thereof comprising 1, 2, 3, or 4 amino acid substitutions; and (c) a heavy chain CDR3 comprising DKYDIPDAFDI (SEQ ID NO:25), or a variant thereof comprising 1, 2, 3, or 4 amino acid substitutions. In certain embodiments, the Jagged-binding agent further comprises (a) a light chain CDR1 comprising RASQGISNDLA (SEQ ID NO:26), or a variant thereof comprising 1, 2, 3, or 4 amino acid substitutions; (b) a light chain CDR2 comprising. ATSTLQS (SEQ ID NO:27), or a variant thereof comprising 1, 2, 3, or 4 amino acid substitutions; and (c) a light chain CDR3 comprising QQSYNAPI (SEQ ID NO:28), or a variant thereof comprising 1, 2, 3, or 4 amino acid substitutions. In some alternative embodiments, the Jagged-binding agent comprises (a) a light chain CDR1 comprising RASQGISNDLA (SEQ ID NO:26), or a variant thereof comprising 1, 2, 3, or 4 amino acid substitutions; (b) a light chain CDR2 comprising ATSTLQS (SEQ ID NO:27), or a variant thereof comprising 1, 2, 3, or 4 amino acid substitutions; and (c) a light chain CDR3 comprising QQSYNAPI (SEQ ID NO:28), or a variant thereof comprising 1, 2, 3, or 4 amino acid substitutions. In certain embodiments, the amino acid substitutions are conservative substitutions. In certain embodiments, the Jagged-binding agent specifically binds human Jagged1. In certain embodiments, the Jagged-binding agent further specifically binds human Jagged2. In certain embodiments, the Jagged-binding agent specifically binds human Jagged2.

In certain embodiments, the invention provides a Jagged-binding agent (e.g., an antibody) that specifically binds to an extracellular domain of human Jagged1, wherein the Jagged-binding agent comprises: a heavy chain CDR1 comprising SSNWWS (SEQ ID NO:37), a heavy chain. CDR2 comprising EIFHGENTNYNPSLKS (SEQ ID NO:38), and a heavy chain CDR3 comprising NPGIGAAKFDS (SEQ ID NO:39). In certain embodiments, the Jagged-binding agent further comprises: a light chain CDR1 comprising KSSQSLLHS-DGKTYLY (SEQ ID NO:40), a light chain CDR2 comprising EVSNRFS (SEQ ID NO:41), and a light chain CDR3 comprising MQHIDFP (SEQ ID NO:42). In some alternative embodiments, the Jagged-binding agent comprises: a light chain CDR1 comprising KSSQSLLHSDGKTYLY (SEQ ID NO:40), a light chain CDR2 comprising EVSNRFS (SEQ ID NO:41), and a light chain CDR3 comprising MQHIDFP (SEQ ID NO:42).

In certain embodiments, the invention provides a Jagged-binding agent (e.g., an antibody) that specifically binds to an extracellular domain of human Jagged1, wherein the Jagged-binding agent comprises (a) a heavy chain CDR1 comprising SSNWWS (SEQ ID NO:37), or a variant thereof comprising 1, 2, 3, or 4 amino acid substitutions; (b) a heavy chain CDR2 comprising EIFHGENTNYNPSLKS (SEQ ID NO:38), or a variant thereof comprising 1, 2, 3, or 4 amino acid substitutions; and (c) a heavy chain CDR3 comprising NPGIGAAK-FDS (SEQ ID NO:39), or a variant thereof comprising 1, 2, 3, or 4 amino acid substitutions. In certain embodiments, the Jagged-binding agent further comprises (a) a light chain CDR1 comprising. KSSQSLLHSDGKTYLY (SEQ ID NO:40), or a variant thereof comprising 1, 2, 3, or 4 amino acid substitutions; (b) a light chain CDR2 comprising EVS-NRFS (SEQ ID NO:41), or a variant thereof comprising 1, 2, 3, or 4 amino acid substitutions; and (c) a light chain CDR3 comprising MQHIDFP (SEQ ID NO:42), or a variant thereof comprising 1, 2, 3, or 4 amino acid substitutions. In some alternative embodiments, the Jagged-binding agent comprises (a) a light chain CDR1 comprising KSSQSLLHS-DGKTYLY (SEQ ID NO:40), or a variant thereof comprising 1, 2, 3, or 4 amino acid substitutions; (b) a light chain CDR2 comprising EVSNRFS (SEQ ID NO:41), or a variant thereof comprising 1, 2, 3, or 4 amino acid substitutions; and (c) a light chain CDR3 comprising MQHIDFP (SEQ ID NO:42), or a variant thereof comprising 1, 2, 3, or 4 amino acid substitutions. In certain embodiments, the amino acid substitutions are conservative substitutions.

In certain embodiments, the invention provides a Jagged-binding agent (e.g., an antibody) that specifically binds to an extracellular domain of human Jagged 1 and/or human Jagged2, wherein the Jagged-binding agent comprises a heavy chain variable region having at least about 80% sequence identity to SEQ ID NO:5, and/or a light chain variable region having at least 80% sequence identity to SEQ ID NO:7. In certain embodiments, the Jagged-binding agent comprises a heavy chain variable region having at least about 85%, at least about 90%, at least about 95%, at least about 97%, or at least about 99% sequence identity to SEQ ID NO:5. In certain embodiments, the Jagged-binding agent comprises a light chain variable region having at least about 85%, at least about 90%, at least about 95%, at least about 97%, or at least about 99% sequence identity to SEQ ID NO:7. In certain embodiments, the Jagged-binding agent comprises a heavy chain variable region having at least about 95% sequence identity to SEQ ID NO:5, and/or a light chain variable region having at least about 95% sequence identity to SEQ ID NO:7. In certain embodiments, the Jagged-binding agent comprises a heavy chain variable region comprising SEQ ID NO:5 and/or a light chain variable region comprising SEQ ID NO:7. In certain embodiments, the Jagged-binding agent comprises a heavy chain variable region comprising SEQ ID NO:5 and a light chain variable region comprising SEQ ID NO:7. In certain embodiments, the Jagged-binding agent specifically binds human Jagged1. In certain embodiments, the Jagged-binding agent further specifically binds human Jagged2. In certain embodiments, the Jagged-binding agent specifically binds human Jagged2.

In certain embodiments, the invention provides a Jagged-binding agent (e.g., an antibody) that specifically binds to an extracellular domain of human Jagged 1 and/or human Jagged2, wherein the Jagged-binding agent comprises a heavy chain variable region having at least about 80% sequence identity to SEQ ID NO:19, SEQ ID NO:50, SEQ ID NO:51, or SEQ ID NO:52, and/or a light chain variable region having at least 80% sequence identity to SEQ ID NO:21. In certain embodiments, the Jagged-binding agent comprises a heavy chain variable region having at least about 85%, at least about 90%, at least about 95%, at least about 97%, or at least about 99% sequence identity to SEQ ID NO:19. In certain embodiments, the Jagged-binding agent comprises a heavy chain variable region having at least about 85%, at least about 90%, at least about 95%, at least about 97%, or at least about 99% sequence identity to SEQ ID NO:50. In certain embodiments, the Jagged-binding agent comprises a heavy chain variable region having at least about 85%, at least about 90%, at least about 95%, at least about 97%, or at least about 99% sequence identity to SEQ ID NO:51. In certain embodiments, the Jagged-binding agent comprises a heavy chain variable region having at least about 85%, at least about 90%, at least about 95%, at least about 97%, or at least about 99% sequence identity to SEQ ID NO:52. In, certain embodiments, the Jagged-binding agent comprises a light chain variable region having at least about 85%, at least about 90%, at least about 95%, at least about 97%, or at least about 99% sequence identity to SEQ ID NO:21. In certain embodiments, the Jagged-binding agent comprises a heavy chain variable region having at least about 95% sequence identity to SEQ ID NO:19, and/or a light chain variable region having at least about 95% sequence identity to SEQ ID NO:21. In certain embodiments, the Jagged-binding agent comprises a heavy chain variable region comprising SEQ ID NO:19 and/or a light chain variable region comprising SEQ ID NO:21. In certain embodiments, the Jagged-binding agent comprises a heavy chain variable region comprising SEQ ID NO:19 and a light chain variable region comprising SEQ ID NO:21. In certain embodiments, the Jagged-binding agent comprises a heavy chain variable region comprising SEQ ID NO:50 and a light chain variable region comprising SEQ ID NO:21. In certain embodiments, the Jagged-binding agent comprises a heavy chain variable region comprising SEQ ID NO:51 and a light chain variable region comprising SEQ ID NO:21. In certain embodiments, the Jagged-binding agent comprises a heavy chain variable region comprising SEQ ID NO:52 and a light chain variable region comprising SEQ ID NO:21. In certain embodiments, the Jagged-binding agent specifically binds human Jagged1. In certain embodiments, the Jagged-binding agent further specifically binds human Jagged2. In certain embodiments, the Jagged-binding agent specifically binds human Jagged2.

In certain, embodiments, the invention provides a Jagged-binding agent (e.g., an antibody) that specifically binds to an extracellular domain of human Jagged1, wherein the Jagged-binding agent comprises a heavy chain variable region having at least about 80% sequence identity to SEQ ID NO:33, and/or a light chain variable region having at least 80% sequence identity to SEQ ID NO:35. In certain embodiments, the Jagged-binding agent comprises a heavy chain variable region having at least about 85%, at least about 90%, at least about 95%, at least about 97%, or at least about 99% sequence identity to SEQ ID NO:33. In certain embodiments, the Jagged-binding agent comprises a light chain variable region having at least about 85%, at least about 90%, at least about 95%, at least about 97%, or at least about 99% sequence identity to SEQ ID NO:35. In certain embodiments, the Jagged-binding agent comprises a heavy chain variable region having at least about 95% sequence identity to SEQ ID NO:33, and/or a light chain variable region having at least about 95% sequence identity to SEQ ID NO:35. In certain embodiments, the Jagged-binding agent comprises a heavy chain variable region comprising SEQ ID NO:33 and/or a light chain variable region comprising SEQ ID NO:35. In certain embodiments, the Jagged-binding agent comprises a heavy chain variable region comprising SEQ ID NO:33 and a light chain variable region comprising SEQ ID NO:35.

In certain embodiments, the Jagged-binding agent (e.g., an antibody) binds to the same epitope that a Jagged-binding agent comprising the heavy chain variable region comprising SEQ ID NO:5, and/or a light chain variable region comprising SEQ ID NO:7 binds. In some embodiments, the Jagged-binding agent (e.g., antibody) binds to the same epitope as the 64M51 antibody. In Certain embodiments, the Jagged-binding agent (e.g., antibody) binds to the same epitope as that antibody comprising the heavy chain variable region comprising SEQ ID NO:19, and/or a light chain variable region comprising SEQ ID NO:21 binds. In some embodiments, the Jagged-binding agent or antibody binds to the same epitope as the 64R7 antibody. In certain embodiments, the Jagged-binding agent (e.g., antibody) binds to the same epitope as that antibody comprising the heavy chain variable region comprising SEQ ID NO:50, and/or a light chain variable region comprising SEQ ID NO:21 binds. In some embodiments, the Jagged-binding agent or antibody binds to the same epitope as the 133R0201 antibody. In certain embodiments, the Jagged-binding agent (e.g., antibody) binds to the same epitope as that antibody comprising the heavy chain variable region comprising SEQ ID NO:51, and/or a light chain variable region comprising SEQ ID NO:21 binds. In some embodiments; the Jagged-binding agent or antibody binds to the same epitope as the 133R0203 antibody. In certain embodiments, the Jagged-binding agent (e.g., antibody) binds to the same epitope as that antibody comprising the heavy chain variable region comprising SEQ ID NO:52, and/or a light chain variable region comprising SEQ ID NO:21 binds. In some embodiments, the Jagged-binding agent or antibody binds to the same epitope as the 133R0205 antibody. In certain embodiments, the Jagged-binding agent (e.g., antibody) binds to the same epitope that antibody comprising the heavy chain variable region comprising SEQ ID NO:33, and/or a light chain variable region comprising SEQ ID NO:35 binds. In some embodiments, the Jagged-binding agent or antibody binds to the same epitope as the 64R1B antibody. In some embodiments, the Jagged-binding agent (e.g., antibody) binds to an overlapping epitope. In some embodiments, the Jagged-binding agent Or antibody binds to an epitope that is distinct from the epitope anti-Jagged1 antibody 64M14 binds to. Antibody 64M 14 is described in U.S. Patent Application Pub. No. 2008/0317760.

In certain embodiments, the Jagged-binding agent (e.g., an antibody) competes for specific binding to an extracellular domain of human Jagged1 and/or human Jagged2 with an antibody, wherein the antibody comprises a heavy chain variable region comprising SEQ ID NO:5, and/or a light chain variable region comprising SEQ ID NO:7. In certain embodiments, the Jagged-binding agent competes for specific binding to an extracellular domain of human Jagged1 and/or human Jagged2 with an antibody, wherein the antibody comprises a heavy chain variable region comprising SEQ ID NO:19, and/or a light chain variable region comprising SEQ ID NO:21. In certain embodiments, the Jagged-binding agent competes for specific binding to an extracellular domain of human Jagged1 and/or human Jagged2 with an antibody, wherein the antibody comprises a heavy chain variable region comprising SEQ ID NO:50, and/or a light chain variable region comprising SEQ ID NO:21. In certain embodiments, the Jagged-binding agent competes for specific binding to an extracellular domain of human Jagged1 and/or human Jagged2 with an antibody, wherein the antibody comprises a heavy chain variable region comprising SEQ ID NO:51, and/or a light chain variable region comprising SEQ ID NO:21. In certain embodiments, the Jagged-binding agent competes for specific binding to an extracellular domain of human Jagged1 and/or human Jagged2 with an antibody, wherein the antibody comprises a heavy chain variable region comprising SEQ ID NO:52, and/or a light chain variable region comprising SEQ ID NO:21. In some embodiments, the Jagged-binding agent competes for specific binding to human Jagged1. In some embodiments, the Jagged-binding agent competes for specific binding to human. Jagged2. In some embodiments, the Jagged-binding agent competes for specific binding to both human Jagged1 and human Jagged2. In some embodiments, the Jagged-binding agent or antibody competes for specific binding to an extracellular domain of human Jagged1 or Jagged 2 in a competitive binding assay.

In certain embodiments, the Jagged-binding agent competes for specific binding to an extracellular domain of human Jagged1 with an antibody, wherein the antibody comprises a heavy chain variable region comprising SEQ ID NO:33, and/or a light chain variable region comprising SEQ ID NO:35. In some embodiments, the Jagged-binding agent or antibody competes for specific binding to an extracellular domain of human Jagged1 in a competitive binding assay.

In certain embodiments, the Jagged-binding agent competes with antibody 64M51 for specific binding to human Jagged1. In certain embodiments, the Jagged-binding agent competes with antibody 64M51 for specific binding to human Jagged2. In certain embodiments, the Jagged-binding agent competes with antibody 64R7 for specific binding to human Jagged 1. In certain embodiments, the Jagged-binding agent competes with antibody 64R7 for specific binding to human Jagged2. In certain embodiments, the Jagged-binding agent competes with antibody 133R0201 for specific binding to human Jagged1. In certain embodiments, the Jagged-binding agent competes with antibody 133R0201 for specific binding to human Jagged2. In certain embodiments, the Jagged-binding agent competes with antibody 133R0203 for specific binding to human Jagged1. In certain embodiments, the Jagged-binding agent competes with antibody 133R0203 for specific binding to human Jagged2. In certain embodiments, the Jagged-binding agent competes with antibody 133R0205 for specific binding to human Jagged 1. In certain embodiments, the Jagged-binding agent competes with antibody 133R0205 for specific binding to human Jagged2. In certain embodiments, the Jagged-binding agent competes with antibody 64R1B for specific binding to human Jagged 1. In certain embodiments, the Jagged-binding agent does not compete with anti-Jagged antibody 64M14 for specific binding to human Jagged1. In some embodiments, the Jagged-binding agent or antibody competes for specific binding to an extracellular domain of human Jagged1 or Jagged 2 in a competitive binding assay.

The invention provides polypeptides, including, but not limited to, antibodies that specifically bind to human Jagged1 and/or human Jagged2. In certain embodiments, the polypeptide comprises one, two, three, four, five and/or six of the CDRs of antibodies 64M51, 64R1B, 64R7, 133R0201, 133R0203, or 133R0205 (see Table 1 herein). In some embodiments, the polypeptide comprises one or more of the CDRs of 64M51, two or more of the CDRs of 64M51, three or more of the CDRs of 64M51, four or more of the CDRs of 64M51, five or more of the CDRs of 64M51, or all six of the CDRs or 64M51. In some embodiments, the polypeptide comprises one or more of the CDRs of 64R7, two or more of the CDRs of 64R7, three or more of the CDRs of 64R7, four or more of the CDRs of 64R7, five or more of the CDRs of 64R7, or all six of the CDRs or 64R7. In some embodiments, the polypeptide comprises one or more of the CDRs of 64R1B, two or more of the CDRs of 64R1B, three or more of the CDRs of 64R1B, four or more of the CDRs of 64R1B, five or more of the CDRs of 64R1B, or all six of the CDRs or 64R1B. In some embodiments, the polypeptide comprises CDRs with up to four (i.e., 0, 1, 2, 3, or 4) amino acid substitutions per CDR. In certain embodiments, the heavy chain CDR(s) are contained within a heavy chain variable region. In certain embodiments, the light chain CDR(s) are contained within a light chain variable region.

In some embodiments, the invention provides a polypeptide that specifically binds a human Jagged1 and/or human Jagged2, wherein the polypeptide comprises: an amino acid sequence having at least about 80% sequence identity to SEQ ID NO:5, and/or an amino acid sequence having at least 80% sequence identity to SEQ ID NO:7. In certain embodiments, the polypeptide comprises an amino acid sequence having at least about 85%, at least about 90%, at least about 95%, at least about 97%, or at least about 99% sequence identity to SEQ ID NO:5. In certain embodiments, the polypeptide comprises an amino acid sequence having at least about 85%, at least about 90%, at least about 95%, at least about 97%, or at least about 99% sequence identity to SEQ ID NO:7. In certain embodiments, the polypeptide comprises an amino acid sequence having at least about 95% sequence identity to SEQ ID NO:5, and/or an amino acid sequence having at least about 95% sequence identity to SEQ ID NO:7. In certain embodiments, the polypeptide comprises an amino acid sequence comprising SEQ ID NO:5 and/or an amino acid sequence comprising SEQ ID NO:7. In certain embodiments, the polypeptide comprises an amino acid sequence comprising SEQ ID NO:5 and an amino acid sequence comprising SEQ ID NO:7. In certain embodiments, the polypeptide specifically binds Jagged 1. In some embodiments, the polypeptide further specifically binds Jagged2. In some embodiments, the polypeptide specifically binds Jagged2.

In some embodiments, the invention provides a polypeptide that specifically binds a human Jagged1 and/or human Jagged2, wherein the polypeptide comprises: an amino acid sequence having at least about 80% sequence identity to SEQ ID NO:19, SEQ ID NO:50, SEQ ID NO:51, or SEQ ID NO:52, and/or an amino acid sequence having at least 80% sequence identity to SEQ ID NO:21. In certain embodiments, the polypeptide comprises an amino acid sequence having at least about 85%, at least about 90%, at least about 95%, at least about 97%, or at least about 99% sequence identity to SEQ ID NO:19, SEQ ID NO:50, SEQ ID NO:51, or SEQ ID NO:52. In certain embodiments, the polypeptide comprises an amino acid sequence having at least about 85%, at least about 90%, at least about 95%, at least about 97%, or at least about 99% sequence identity to SEQ ID NO:21. In certain embodiments, the polypeptide comprises an amino acid sequence having at least about 95% sequence identity to SEQ ID NO:19, and/or an amino acid sequence having at least about 95% sequence identity to SEQ ID NO:21. In certain embodiments, the polypeptide comprises an amino acid sequence comprising SEQ ID NO:19 and/or an amino acid sequence comprising SEQ ID NO:21. In certain embodiments, the polypeptide comprises an amino acid sequence comprising SEQ ID NO:19 and an amino acid sequence comprising SEQ ID NO:21. In certain embodiments, the polypeptide comprises an amino acid sequence comprising SEQ ID NO:50 and an amino acid sequence comprising SEQ ID NO:21. In certain embodiments, the polypeptide comprises an amino acid sequence comprising SEQ ID NO:51 and an amino acid sequence comprising SEQ ID NO:21. In certain embodiments, the polypeptide comprises an amino acid sequence comprising SEQ ID NO:52 and an amino acid sequence comprising SEQ ID NO:21. In certain embodiments, the polypeptide specifically binds Jagged1. In some embodiments, the polypeptide further specifically binds Jagged2. In some embodiments, the polypeptide specifically binds Jagged2.

In some embodiments, the invention provides a polypeptide that specifically binds a human Jagged1, wherein the polypeptide comprises: an amino acid sequence having at least about 80% sequence identity to SEQ ID NO:33, and/or an amino acid sequence having at least 80% sequence identity to SEQ ID NO:35. In certain embodiments, the polypeptide comprises an amino acid sequence having at least about 85%, at least about 90%, at least about 95%, at least about 97%, or at least about 99% sequence identity to SEQ ID NO:33. In certain embodiments, the polypeptide comprises an amino acid sequence having at least about 85%, at least about 90%, at least about 95%, at least about 97%, or at least about 99% sequence identity to SEQ ID NO:35. In certain embodiments, the polypeptide comprises an amino acid sequence having at least about 95% sequence identity to SEQ ID NO:33, and/or an amino acid sequence having at least about 95% sequence identity to SEQ ID NO:35. In certain embodiments, the polypeptide comprises an amino acid sequence comprising SEQ ID NO:33 and/or an amino acid sequence comprising SEQ ID NO:35. In certain embodiments, the polypeptide comprises an amino acid sequence comprising SEQ ID NO:33 and an amino acid sequence comprising SEQ ID NO:35.

Polypeptides comprising one of the individual light chains or heavy chains described herein, as well as polypeptides (e.g., antibodies) comprising both a light chain and a heavy chain described herein are also provided.

In certain embodiments, the Jagged-binding agent comprises, consists essentially of, or consists of, an anti-Jagged antibody selected from the group consisting of 64M51, 64R1B, 64R7, 133R0201, 133R0203, and 133R0205 IgG antibodies. In some embodiments, the Jagged-binding agent is not anti-Jagged1 antibody 64M14.

In certain embodiments, the Jagged-binding agent comprises the heavy chains and light chains of the 64M51 IgG2 antibody (with or without the leader sequence). In certain embodiments, the Jagged-binding agent is the 64M51 IgG2 antibody. The hybridoma cell line producing the 64M51 IgG2 antibody was deposited with the American Type Culture Collection (ATCC), 10801 University Boulevard, Manassas, Va., USA, under the conditions of the Budapest Treaty on Nov. 13, 2009 and assigned ATCC deposit designation number PTA-10468. In certain embodiments, the Jagged-binding agent comprises the heavy chains and light chains of the 64R1B antibody (with or without the leader sequence). In certain embodiments, the Jagged-binding agent is the 64R1B antibody. DNA encoding the heavy chains and light chains of the 64R1B antibody was deposited with the ATCC, under the conditions of the Budapest Treaty on Nov. 13, 2009, and assigned ATCC deposit designation number PTA-10469. In certain embodiments, the Jagged-binding agent comprises the heavy chains and light chains of the 64R7 antibody (with or without the leader sequence). In certain embodiments, the Jagged-binding agent is the 64R7 antibody. DNA encoding the heavy chains and light chains of the 64R7 IgG2 antibody was deposited with the ATCC, under the conditions of the Budapest Treaty on Nov. 13, 2009 and assigned ATCC deposit designation number PTA-10470.

In certain embodiments, the Jagged-binding agent is an agent that competes for specific binding to Jagged1 and/or Jagged2 with an antibody produced by the hybridoma having ATCC deposit designation number PTA-10468 (e.g., in a competitive binding assay). In certain embodiments, the Jagged-binding agent is an agent that competes for specific binding to Jagged1 and/or Jagged2 with an antibody encoded by the plasmid having ATCC deposit designation number PTA-10470 (e.g., in a competitive binding assay). In certain embodiments, the Jagged-binding agent is an agent that competes for specific binding to Jagged1 with an antibody encoded by the plasmid having ATCC deposit designation number PTA-10469 (e.g., in a competitive binding assay).

In certain embodiments, the Jagged-binding agent (e.g., an antibody) as described herein binds to Jagged and modulates Jagged activity. In some embodiments, the Jagged-binding agent is an agonist and modulates Jagged activity. In some embodiments, the Jagged-binding agent is an antagonist and modulates Jagged activity.

In certain embodiments, the Jagged-binding agent (e.g., an antibody) is an antagonist of at least one human Jagged (e.g., Jagged1 or Jagged2). In some embodiments, the Jagged-binding agent is an antagonist of at least one Jagged and inhibits Jagged activity. In some embodiments, the Jagged-binding agent inhibits human Jagged1 activity. In some embodiments, the Jagged-binding agent inhibits human Jagged2 activity. In some embodiments, the Jagged-binding agent inhibits both human Jagged1 and human Jagged2 activity. In certain embodiments, the Jagged-binding agent inhibits at least about 10%, at least about 20%, at least about 30%, at least about 50%, at least about 75%, at least about 90%, or about 100% of the activity of the bound human Jagged.

In certain embodiments, the Jagged-binding agent (e.g., an antibody) inhibits binding of Jagged to at least one Notch receptor. In some embodiments, the Jagged-binding agent blocks binding of Jagged to at least one Notch receptor. In certain embodiments, the Notch receptor is a human Notch. In certain embodiments, the Jagged-binding agent inhibits or blocks binding of Jagged (e.g., human Jagged1 or human Jagged2) to human Notch1, Notch2, Notch3, and/or Notch4.

In certain embodiments, the Jagged-binding agent inhibits at least about 10%, at least about 25%, at least about 50%, at least about 75%, at least about 90%, or at least about 95% of binding of a particular Jagged to a particular human Notch receptor. In certain embodiments, a Jagged-binding agent that inhibits binding of a Jagged such as a human Jagged1 or human Jagged2 to a Notch receptor, further inhibits Notch signaling. In certain embodiments, antibody 64M51 inhibits binding of human Jagged to a Notch. In certain embodiments, 64M51 inhibits binding of human Jagged1 to a human Notch. In certain embodiments, 64M51 inhibits binding of human Jagged2 to a human Notch. In certain embodiments, antibody 64R7 inhibits binding of human Jagged to a Notch. In certain embodiments, 64R7 inhibits binding of human Jagged1 to a human Notch. In certain embodiments, 64R7 inhibits binding of human Jagged2 to a human Notch. In certain embodiments, antibody 133R0201 inhibits binding of human Jagged to a Notch. In certain embodiments, 133R0201 inhibits binding of human Jagged1 to a human Notch. In certain embodiments, 133R0201 inhibits binding of human Jagged2 to a human Notch. In certain embodiments, antibody 133R0203 inhibits binding of human Jagged to a Notch. In certain embodiments, 133R0203 inhibits binding of human Jagged1 to a human Notch. In certain embodiments, 133R0203 inhibits binding of human Jagged2 to a human Notch. In certain embodiments, antibody 133R0205 inhibits binding of human Jagged to a Notch. In certain embodiments, 133R0205 inhibits binding of human Jagged1 to a human Notch. In certain embodiments, 133R0205 inhibits binding of human Jagged2 to a human Notch. In certain embodiments, antibody 64R1B inhibits binding of human Jagged1 to a human Notch.

In certain embodiments, the Jagged-binding agent (e.g., an antibody) inhibits Notch signaling. It is understood that a Jagged-binding agent that inhibits Notch signaling may, in certain embodiments, inhibit signaling by one or more Notchs, but not necessarily inhibit signaling by all Notchs. In certain alternative embodiments, signaling by all human Notchs may be inhibited. In certain embodiments, signaling by one or more Notchs selected from the group consisting of Notch1, Notch2, Notch3 and Notch4 is inhibited. In certain embodiments, the inhibition of Notch signaling by a Jagged-binding agent is a reduction in the level of Notch signaling of at least about 10%, at least about 25%, at least about 50%, at least about 75%, at least about 90%, or at least about 95%.

In certain embodiments, the Jagged-binding agent (e.g., an antibody) inhibits Notch activation. It is understood that a Jagged-binding agent that inhibits Notch activation may, in certain embodiments, inhibit activation by one or more Notchs, but not necessarily inhibit activation by all Notchs. In certain alternative embodiments, activation by all human Notchs may be inhibited. In certain embodiments, activation by one or more Notchs selected from the group consisting of Notch1, Notch2, Notch3 and Notch4 is inhibited. In certain embodiments, the inhibition of Notch activation by a Jagged-binding agent is a reduction in the level of Notch activation of at least about 10%, at least about 25%, at least about 50%, at least about 75%, at least about 90%, or at least about 95%.

In vivo and in vitro assays for determining whether a Jagged-binding agent (or candidate Jagged-binding agent) inhibits Notch activation are known in the art. In some embodiments, a cell-based, luciferase reporter assay utilizing a TCF/Luc reporter vector containing multiple copies of the TCF-binding domain upstream of a firefly luciferase reporter gene may be used to measure Notch signaling levels in vitro. In other embodiments, a cell-based, luciferase reporter assay utilizing a CBF/Luc reporter vector containing multiple copies of the CBF-binding domain upstream of a firefly luciferase reporter gene may be used. The level of Notch activation induced by Jagged in the presence of the Jagged-binding agent is compared to the level of Notch activation induced by Jagged in the absence of the Jagged-binding agent. Non-limiting, specific examples of the use of such luciferase reporter assays to assess inhibition of Notch activation are provided in Example 6 and FIGS. 4 and 5.

In certain embodiments, the Jagged-binding agents (e.g., antibodies) have one or more of the following effects: inhibit proliferation of tumor cells, inhibit tumor growth, prevent or reduce metastasis of tumor cells, reduce the frequency of cancer stem cells in a tumor, trigger cell death of tumor cells (e.g., by apoptosis), reduce the tumorigenicity of a tumor by reducing the frequency of cancer stem cells in the tumor, differentiate tumorigenic cells to a non-tumorigenic state, inhibit angiogenesis, or increase survival of a patient.

In certain embodiments, the Jagged-binding agents (e.g., antibodies) are capable of inhibiting tumor growth. In certain embodiments, the Jagged-binding agents are capable of inhibiting growth of tumor cells in vitro (e.g., contacting tumor cells with an antibody in vitro). In certain embodiments, the Jagged-binding agents are capable of inhibiting tumor growth in vivo (e.g., in a xenograft mouse model and/or in a human having cancer).

In certain embodiments, the Jagged-binding agents (e.g., antibodies) are capable of reducing the tumorigenicity of a tumor. In certain embodiments, the Jagged-binding agent or antibody is capable of reducing the tumorigenicity of a tumor comprising cancer stem cells in an animal model, such as a mouse xenograft model. In some embodiments, the Jagged-binding agent is capable of reducing the tumorigenicity of a tumor by reducing the frequency of cancer stem cells in the tumor. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the frequency of cancer stem cells is determined by a limiting dilution assay (LDA) using an animal model. Examples and guidance regarding the use of limiting dilution assays to determine a reduction in the number or frequency of cancer stem cells in a tumor can be found, e.g., in International Pub. Number WO 2008/042236 and U.S. Patent Application Pub. Nos. 2008/0064049 and 2008/0178305.

In certain embodiments, Jagged-binding agents or antibodies mediate cell death of a cell expressing Jagged via antibody-dependent cellular cytotoxicity (ADCC). ADCC involves cell lysis by effector cells that recognize the Fc portion of an antibody. Many lymphocytes, monocytes, tissue macrophages, granulocytes and eosinophiles, for example, have Fc receptors and can mediate cytolysis (Dillman, 1994, *J. Clin. Oncol.* 12:1497).

In certain embodiments, Jagged-binding agents or antibodies trigger cell death of a cell expressing Jagged by activating complement-dependent cytotoxicity (CDC). CDC involves binding of serum complement to the Fc portion of an antibody and subsequent activation of the complement protein cascade, resulting in cell membrane damage and eventual cell death. Biological activity of antibodies is known to be determined, to a large extent, by the constant domains or Fc region of the antibody molecule (Uananue and Benacerraf, 1984, Textbook of Immunology, 2nd Edition, Williams & Wilkins, p. 218). Antibodies of different classes and subclasses differ in this respect, as do antibodies of the same subclass but from different species. Of human antibodies, IgM is the most efficient class of antibodies to bind complement, followed by IgG1, IgG3, and IgG2 whereas IgG4 appears quite deficient in activating the complement cascade (Dillman, 1994, *J. Clin. Oncol.* 12:1497; Jefferis et al., 1998, *Immunol. Rev.* 163:59-76). According to the present invention, antibodies of those classes having the desired biological activity can be prepared.

The ability of any particular Jagged-binding agent or antibody to mediate lysis of the target cell by CDC and/or ADCC can be assayed. In some embodiments, the cells of interest are grown and labeled in vitro (target cells) and the antibody is added to the cell culture in combination with either serum complement or immune cells which can be activated by the antigen-antibody complexes. Cytolysis of the target cells is detected, for example, by the release of label from the lysed cells. In some embodiments, antibodies can be screened using a patient's own serum as a source of complement and/or immune cells. The antibody that is capable of activating complement or mediating ADCC in the in vitro test can then be used therapeutically in that particular patient.

In certain embodiments, the Jagged-binding agent (e.g., an antibody) has a circulating half-life in a subject or mammal (e.g., mice, rats, cynomolgus monkeys, or humans) of at least about 5 hours, at least about 10 hours, at least about 24 hours, at least about 48 hrs, at least about 3 days, at least about 1 week, or at least about 2 weeks. In certain embodiments, the Jagged-binding agent is an IgG (e.g., IgG1 or IgG2) antibody that has a circulating half-life in a subject or mammal (e.g., mice, rats, cynomolgus monkeys, or humans) of at least about 5 hours, at least about 10 hours, at least about 24 hours, at least about 3 days, at least about 1 week, or at least about 2 weeks. Methods of increasing the half-life of agents such as polypeptides and antibodies are known in the art. In some embodiments, known methods of increasing the circulating half-life of IgG antibodies include the introduction of mutations in the Fc region which increase the pH-dependent binding of the antibody to the neonatal Fc receptor (FcRn) at pH 6.0 (see e.g., U.S Patent Pub. Nos. 2005/0276799; 2007/0148164; and 2007/0122403). Known methods of increasing the circulating half-life of antibody fragments lacking the Fc region include, but are not limited to, techniques such as PEGylation.

In some embodiments, the Jagged-binding agents are polyclonal antibodies. Polyclonal antibodies can be prepared by any known method. Polyclonal antibodies are prepared by immunizing an animal (e.g., a rabbit, rat, mouse, goat, donkey, etc.) by multiple subcutaneous or intraperitoneal injections of the relevant antigen (e.g., a purified peptide fragment, full-length recombinant protein, fusion protein, etc.). The antigen can be optionally conjugated to a carrier protein such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from blood, ascites and the like, of the immunized animal. Polyclonal antibodies can be purified from serum or ascites according to standard methods in the art including, but not limited to, affinity chromatography, ion-exchange chromatography, gel electrophoresis, and dialysis.

In some embodiments, the Jagged-binding agents are monoclonal antibodies. Monoclonal antibodies can be prepared using hybridoma methods known to one of skill in the art (see e.g., Kohler and Milstein, 1975, *Nature* 256:495). Using the hybridoma method, a mouse, hamster, or other appropriate host animal, is immunized as described above to elicit from lymphocytes the production of antibodies that will specifically bind to the immunizing antigen. In some embodiments, lymphocytes can also be immunized in vitro. In some embodiments, the immunizing antigen (e.g., Jagged1) can be a human protein or a portion thereof. In some embodiments, the immunizing antigen (e.g., Jagged1) can be a mouse protein or a portion thereof. In some embodiments, the immunizing antigen can be an extracellular domain of human Jagged1. In some embodiments, the immunizing antigen can be an extracellular domain of mouse Jagged1. In some embodiments, a mouse is immunized with a human antigen. In some embodiments, a mouse is immunized with a mouse antigen.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed against a chosen antigen may be identified by a variety of techniques including, but not limited to, immunoprecipitation, immunoblotting, and in vitro binding assays (e.g., flow cytometry, enzyme-linked immunosorbent assay (ELISA), radioimmunoassay (RIA)). The hybridomas can be propagated either in in vitro culture using standard methods (Goding, Monoclonal Antibodies: Principles and Practice, Academic Press, 1986) or in in vivo as ascites in an animal. The monoclonal antibodies can be purified from the culture medium or ascites fluid according to standard methods in the art including, but not limited to, affinity chromatography, ion-exchange chromatography, gel electrophoresis, and dialysis.

Alternatively, monoclonal antibodies can be made using recombinant DNA techniques as known to one skilled in the art (see e.g., U.S. Pat. No. 4,816,567). The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional techniques. The isolated polynucleotides encoding the heavy and light chains are cloned into suitable expression vectors which produce the monoclonal antibodies when transfected into host cells such as *E. coli*, simian COS cells, Chinese hamster ovary (CHO) cells, or myeloma cells that do not otherwise produce immunoglobulin protein. Recombinant monoclonal antibodies, or fragments thereof, can also be isolated from phage display libraries expressing CDRs of the desired species (see e.g., McCafferty et al., 1990, *Nature*, 348:552-554; Clackson et al., 1991, *Nature*, 352:624-628; and Marks et al., 1991, *J. Mol. Biol.*, 222:581-597).

The polynucleotide(s) encoding a monoclonal antibody can be further modified using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, and/or other biological characteristics of a monoclonal antibody. In some embodiments, site-directed mutagenesis of the CDRs can be used to optimize specificity, affinity, and/or other biological characteristics of a monoclonal antibody.

In some embodiments, the Jagged-binding agent is a humanized antibody. Typically, humanized antibodies are human immunoglobulins in which residues from the complementary determining regions (CDRs) are replaced by residues from CDRs of a non-human species (e.g., mouse, rat, rabbit, hamster) that have the desired specificity, affinity, and/or capability using methods known to one skilled in the art. In some embodiments, the Fv framework region (FR) residues of a human immunoglobulin are replaced with the corresponding framework region residues from a non-human immunoglobulin that has the desired specificity, affinity, and/or capability. In some embodiments, the humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all, or substantially all, of the CDRs that correspond to the non-human immunoglobulin whereas all, or substantially all, of the framework regions are those of a human immunoglobulin consensus sequence. In some embodiments, the humanized antibody can also comprise at least a portion of an immunoglobulin constant region or domain (Fc), typically that of a human immunoglobulin. In certain embodiments, such humanized antibodies are used therapeutically because they may reduce antigenicity and HAMA (human anti-mouse antibody) responses when administered to a human subject. One skilled in the art would be able to obtain a functional humanized antibody with reduced immunogenicity following known techniques (see for example U.S. Pat. Nos. 5,225,539; 5,585,089; 5,693,761; and 5,693,762).

In certain embodiments, the Jagged-binding agent is a human antibody. Human antibodies can be directly prepared using various techniques known in the art. Immortalized human B lymphocytes, immunized in vitro or isolated from an immunized individual, that produce an antibody directed against a target antigen can be generated. Alternatively, a human antibody can be selected from a phage library, where that phage library expresses human antibodies by methods well-known to those of skill in the art (see e.g., Vaughan et al., 1996, *Nat. Biotech.*, 14:309-314; Sheets et al., 1998, *Proc. Nat'l. Acad. Sci.*, 95:6157-6162; Hoogenboom and Winter, 1991, *J. Mol. Biol.*, 227:381; and Marks et al., 1991, *J. Mol. Biol.*, 222:581). Techniques for the generation and use of antibody phage libraries are also described in U.S. Pat. Nos. 5,969,108; 6,172,197; 5,885,793; 6,521,404; 6,544,731; 6,555,313; 6,582,915; 6,593,081; 6,300,064; 6,653,068; 6,706,484; and 7,264,963; and Rothe et al., 2008, *J. Mol. Bio.*, 376:1182-1200. Affinity maturation strategies, such as chain shuffling (Marks et al., 1992, *Bio/Technology*, 10:779-783), and PCR-based mutagenesis methods are known in the art and may be employed to generate high affinity human antibodies.

Human antibodies can also be made in transgenic mice containing human immunoglobulin loci that are capable, upon immunization, of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments, the Jagged-binding agent is a bispecific antibody. Bispecific antibodies are capable of specifically recognizing and binding to at least two different epitopes. The different epitopes can either be within the same molecule or on different molecules. In some embodiments, the antibodies can specifically recognize and bind a first antigen target, (e.g., hJagged) as well as a second antigen target, such as an effector molecule on a leukocyte (e.g., CD2, CD3, CD28, or B7) or a Fc receptor (e.g., CD64, CD32, or CD16) so as to focus cellular defense mechanisms to the cell expressing the first antigen target. In some embodiments, the antibodies can be used to direct cytotoxic agents to cells which express a particular target antigen, such as Jagged. These antibodies possess an antigen-binding arm and an arm which binds a cytotoxic agent or a radionuclide chelator, such as EOTUBE, DPTA, DOTA, or TETA. In certain embodiments, the bispecific antibody specifically binds at least one human Jagged, as well as either VEGF, a second Notch ligand (e.g., DLL1, DLL3 or DLL4), or at least one Notch receptor selected from the group consisting of Notch1, Notch2, Notch3, and Notch4.

Techniques for making bispecific antibodies are known by those skilled in the art, see for example, Millstein et al., 1983, *Nature*, 305:537-539; Brennan et al., 1985, *Science*, 229:81; Suresh et al., 1986, *Methods in Enzymol.*, 121:120; Traunecker et al., 1991, *EMBO J.*, 10:3655-3659; Shalaby et al., 1992, *J. Exp. Med.*, 175:217-225; Kostelny et al., 1992, *J. Immunol.*, 148:1547-1553; Gruber et al., 1994, *J. Immunol.*, 152:5368; and U.S. Pat. No. 5,731,168). Bispecific antibodies can be intact antibodies or antibody fragments. Antibodies with more than two valencies are also contemplated. For example, trispecific antibodies can be prepared (Tutt et al., 1991, *J. Immunol.*, 147:60). Thus, in certain embodiments the antibodies to human Jagged are multispecific.

In certain embodiments, the Jagged-binding agents (e.g., antibodies or other polypeptides) described herein may be monospecific. For example, in certain embodiments, each of the one or more antigen-binding sites that an antibody contains is capable of binding (or binds) a homologous epitope on Jagged. In certain embodiments, an antigen-binding site of a monospecific antibody described herein is capable of binding (or binds) Jagged1 and Jagged2 (i.e., the same epitope is found on Jagged1 and Jagged2).

In certain embodiments, the Jagged-binding agent is an antibody fragment. Antibody fragments may have different functions or capabilities than intact antibodies; for example, antibody fragments can have increased tumor penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced recombinantly. In some embodiments, antibody fragments include Fv or single chain Fv (scFv) fragments. Fab, Fv, and scFv antibody fragments can be expressed in, and secreted from, *E. coli* or other host cells, allowing for the production of large amounts of these fragments. In some embodiments, antibody fragments are isolated from antibody phage libraries as discussed herein. For example, methods can be used for the construction of Fab expression libraries (Fluse et al., 1989, *Science*, 246:1275-1281) to allow rapid and effective identification of monoclonal Fab fragments with the desired specificity for a Jagged protein or derivatives, fragments, analogs or homologs thereof. In some embodiments, antibody fragments are linear antibody fragments as described in U.S. Pat. No. 5,641,870. In certain embodiments, antibody fragments are monospecific or bispecific. In certain embodiments, the Jagged-binding agent is a scFv. Various techniques can be used for the production of single-chain antibodies specific to Jagged1 and/or Jagged2 (see, e.g., U.S. Pat. No. 4,946,778).

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

For the purposes of the present invention, it should be appreciated that modified antibodies, or fragments thereof, can comprise any type of variable region that provides for the association of the antibody with Jagged. In this regard, the variable region may be derived from any type of mammal that can be induced to mount a humoral response and generate immunoglobulins against a desired antigen (e.g., Jagged1 or Jagged2). As such, the variable region of the modified antibodies can be, for example, of human, murine, non-human primate (e.g., cynomolgus monkeys, macaques, etc.) or lapine origin. In some embodiments, both the variable and constant regions of the modified immunoglobulins are human. In other embodiments, the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence modification. Although the CDRs may be derived from an antibody of the same class or even subclass as the antibody from which the framework regions are derived, it is envisaged that the CDRs will be derived from an antibody of a different class and preferably from an antibody from a different species. It may not be necessary to replace all of the CDRs with all of the CDRs from the donor variable region to transfer the antigen binding capacity of one variable domain to another. Rather, it may only be necessary to transfer those residues that are necessary to maintain the activity of the antigen binding site.

Alterations to the variable region notwithstanding, those skilled in the art will appreciate that the modified antibodies of this invention will comprise antibodies (e.g., full-length antibodies or antigen-binding fragments thereof) in which at least a fraction of one or more of the constant region domains has been deleted or otherwise altered so as to provide desired biochemical characteristics, such as increased tumor localization, increased tumor penetration, reduced serum half-life or increased serum half-life, when compared with an antibody of approximately the same immunogenicity comprising a native or unaltered constant region. In some embodiments, the constant region of the modified antibodies comprises a human constant region. Modifications to the constant region include additions, deletions or substitutions of one or more amino acids in one or more domains. The modified antibodies disclosed herein may comprise alterations or modifications to one or more of the three heavy chain constant domains (CH1, CH2 or CH3) and/or to the light chain constant domain (CL). In some embodiments, one or more domains are partially or entirely deleted from the constant regions of the modified antibodies. In some embodiments, the entire CH2 domain has been removed (ΔCH2 constructs). In some embodiments, the omitted constant region domain is replaced by a short amino acid spacer (e.g., 10 aa residues) that provides some of the molecular flexibility typically imparted by the absent constant region.

In certain embodiments, the modified antibodies are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies may have only a partial deletion of a constant domain or substitution of a few or even a single amino acid. For example, the mutation of a single amino acid in selected areas of the CH2 domain may be enough to substantially reduce Fc binding and thereby increase tumor localization and/or tumor penetration. Similarly, it may be desirable to simply delete a part of one or more constant region domains that control a specific effector function (e.g., complement C1q binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified antibodies comprise the addition of one or more amino acids to the constant region to enhance desirable characteristics such as decreasing or increasing effector function or provide for more cytotoxin or carbohydrate attachment.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind to a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (ADCC), release of inflammatory mediators, placental transfer and control of immunoglobulin production.

In certain embodiments, the anti-Jagged antibodies provide for altered effector functions that, in turn, affect the biological profile of the administered antibody. For example, in some embodiments, the deletion or inactivation (through point mutations or other means) of a constant region domain may reduce Fc receptor binding of the circulating modified antibody (e.g., anti-Jagged antibody) thereby increasing tumor localization and/or penetration. In other embodiments, the constant region modifications increase or reduce the serum half-life of the antibody. In some embodiments, the constant region is modified to eliminate disulfide linkages or oligosaccharide moieties allowing for enhanced tumor localization and/or penetration.

In certain embodiments, an anti-Jagged antibody does not have one or more effector functions. In some embodiments, the antibody has no antibody-dependent cellular cytoxicity (ADCC) activity and/or no complement-dependent cytoxicity (CDC) activity. In certain embodiments, the antibody does not bind to an Fc receptor and/or complement factors. In certain embodiments, the antibody has no effector function.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids.

Thus, the present invention provides methods for generating an antibody that binds Jagged. In some embodiments, the method for generating an antibody that binds Jagged comprises using hybridoma techniques. In some embodiments, the method comprises using an extracellular domain of mouse Jagged1 as an immunizing antigen. In some embodiments, the method of generating an antibody that binds Jagged comprises screening a human phage library. The present invention further provides methods of identifying an antibody that binds to Jagged. In some embodiments, the antibody is identified by screening for binding to Jagged with flow cytometry (FACS). In some embodiments, the antibody is screened for binding to human Jagged1. In other embodiments, the antibody is screened for binding to human Jagged2. In some embodiments, the antibody is screened for binding to mouse Jagged1. In some embodiments, the antibody is screened for binding to mouse Jagged2. In some embodiments, the antibody is identified by screening for inhibition or blocking of Jagged-induced Notch activation. In some embodiments, the Jagged is human Jagged1. In some embodiments, the Jagged is human Jagged2. In some embodiments, the Jagged is mouse or rat Jagged1. In some embodiments, the Jagged is mouse Jagged2. In some embodiments, the Notch is human Notch1, Notch2, Notch3 or Notch4.

In certain embodiments, the antibodies as described herein are isolated. In certain embodiments, the antibodies as described herein are substantially pure.

In some embodiments of the present invention, the Jagged-binding agents are polypeptides. The polypeptides can be recombinant polypeptides, natural polypeptides, or synthetic polypeptides that bind Jagged. In some embodiments, the polypeptides comprise an antibody or fragment thereof that binds Jagged. It will be recognized by those in the art that some amino acid sequences of a polypeptide can be varied without significant effect on the structure or function of the protein. Thus, the Jagged-binding polypeptides further include variations of the polypeptides which show substantial binding activity against a Jagged protein. In some embodiments, amino acid sequence variations of Jagged-binding polypeptides include deletions, insertions, inversions, repeats, and/or type substitutions.

The polypeptides and variants thereof, can be further modified to contain additional chemical moieties not normally part of the polypeptide. The derivatized moieties can improve the solubility, the biological half-life or absorption of the polypeptide. The moieties can also reduce or eliminate any undesirable side effects of the polypeptides and variants. An overview for such chemical moieties can be found in Remington: The Science and Practice of Pharmacy, 21$^{st}$ Edition, University of the Sciences in Philadelphia, 2005.

The polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof.

In some embodiments, a DNA sequence encoding a polypeptide of interest may be constructed by chemical synthesis using an oligonucleotide synthesizer. Oligonucleotides can be designed based on the amino acid sequence of the desired polypeptide and by selecting those codons that are favored in the host cell in which the recombinant polypeptide of interest will be produced. Standard methods can be applied to synthesize a polynucleotide sequence encoding a polypeptide of interest. For example, a complete amino acid sequence can be used to construct a back-translated gene. Further, a DNA oligomer containing a nucleotide sequence coding for the particular polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular polypeptide of interest can be inserted into an expression vector and operatively linked to an expression control sequence appropriate for expression of the polypeptide in a desired host. Proper assembly can be confirmed by nucleotide sequencing, restriction mapping, and/or expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding Jagged-binding agents such as polypeptides or antibodies, or fragments thereof. For example, recombinant expression vectors can be replicable DNA constructs which have synthetic or cDNA-derived DNA fragments encoding a polypeptide chain of an anti-Jagged antibody, or fragment thereof, operatively linked to suitable transcriptional or translational regulatory elements derived from mammalian, microbial, viral or insect genes. A transcriptional unit generally comprises an assembly of (1) a regulatory element or elements having a role in gene expression, for example, transcriptional promoters and/or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host; usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of an expression vector and control elements depends upon the choice of host. A wide variety of expression host/vector combinations can be employed. Useful expression vectors for eukaryotic hosts include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR1, pBR322, pMB9 and their derivatives and wider host range plasmids, such as M13 and other filamentous single-stranded DNA phages.

Suitable host cells for expression of a Jagged-binding polypeptide or antibody (or a Jagged protein to use as an antigen) include prokaryotes, yeast, insect or higher eukaryotic cells under the control of appropriate promoters. Prokaryotes include gram-negative or gram-positive organisms, for example, *E. coli* or Bacilli. Higher eukaryotic cells include established cell lines of mammalian origin as described below. Cell-free translation systems can also be employed.

Various mammalian or insect cell culture systems are used to express recombinant protein. Expression of recombinant proteins in mammalian cells may be preferred because such proteins are generally correctly folded, appropriately modified and completely functional. Examples of suitable mammalian host cell lines include COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived) and BHK (hamster kidney fibroblast-derived) cell lines. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Baculovirus systems for production of heterologous proteins in insect cells are well known to those of skill in the art (see, e.g., Luckow and Summers, 1988, *Bio/Technology*, 6:47).

The proteins produced by a transformed host can be purified according to any suitable method. Such methods include chromatography (e.g., ion exchange, affinity and sizing column chromatography), centrifugation, differential solubility, or by any other standard technique for protein purification. Affinity tags such as hexa-histidine, maltose binding domain, influenza coat sequence and glutathione-S-transferase can be attached to the protein to allow easy purification by passage over an appropriate affinity column. Isolated proteins can also be physically characterized using such techniques as proteolysis, high performance liquid chromatography (HPLC), nuclear magnetic resonance and x-ray crystallography.

For example, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin can be employed, for example, a matrix or substrate having pendant diethylaminoethyl (DEAE) groups. The matrices can be acrylamide, agarose, dextran, cellulose or other types commonly employed in protein purification. In some embodiments, a cation exchange step can be employed. Suitable cation exchangers include various insoluble matrices comprising sulfopropyl or carboxymethyl groups. In some embodiments, a hydroxyapatite (CHT) media can be employed, including but not limited to, ceramic hydroxyapatite. In some embodiments, one or more reversed-phase HPLC steps employing hydrophobic RP-HPLC media, e.g., silica gel having pendant methyl or other aliphatic groups, can be employed to further purify a protein. Some or all of the foregoing purification steps, in various combinations, can be employed to provide a homogeneous recombinant protein.

In some embodiments, recombinant protein produced in bacterial culture can be isolated, for example, by initial extraction from cell pellets, followed by one or more concentration, salting-out, aqueous ion exchange or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Pub. Nos. 2008/0312425; 2008/0177048; and 2009/0187005.

In certain embodiments, the Jagged-binding agent is a polypeptide that is not an antibody. A variety of methods for identifying and producing non-antibody polypeptides that bind with high affinity to a protein target are known in the art. See, e.g., Skerra, 2007, *Curr. Opin. Biotechnol.*, 18:295-304; Hosse et al., 2006, *Protein Science*, 15:14-27; Gill et al., 2006, *Curr. Opin. Biotechnol.*, 17:653-658; Nygren, 2008, *FEBS J*, 275:2668-76; and Skerra, 2008, *FEBS J.*, 275:2677-83. In certain embodiments, phage display technology may be used to produce and/or identify a Jagged-binding polypeptide. In certain embodiments, the Jagged-binding polypeptide comprises a protein scaffold of a type selected from the group consisting of protein A, protein G, a lipocalin, a fibronectin domain, an ankyrin consensus repeat domain, and thioredoxin.

In certain embodiments, the Jagged-binding agents or antibodies can be used in any one of a number of conjugated (e.g., an immunoconjugate or radioconjugate) or non-conjugated forms. In certain embodiments, the antibodies are used in non-conjugated form to harness the subject's natural defense mechanisms including complement-dependent cytotoxicity (CDC) and/or antibody dependent cellular toxicity (ADCC) to eliminate malignant or cancerous cells.

In certain embodiments, the Jagged-binding agent (e.g., an antibody or polypeptide) is conjugated to a cytotoxic agent. In some embodiments, the cytotoxic agent is a chemotherapeutic agent including, but not limited to, methotrexate, adriamicin, doxorubicin, melphalan, mitomycin C, chlorambucil, daunorubicin or other intercalating agents. In some embodiments, the cytotoxic agent is a enzymatically active toxin of bacterial, fungal, plant, or animal origin, or fragments thereof, including but not limited to, diphtheria A chain, non-binding active fragments of diphtheria toxin, exotoxin A chain, ricin A chain, abrin A chain, modeccin A chain, alpha-sarcin, Aleurites fordii proteins, dianthin proteins, *Phytolaca americana* proteins (PAPI, PAPII, and PAP-S), *Momordica charantia* inhibitor, curcin, crotin, Sapaonaria officinalis inhibitor, gelonin, restrictocin, phenomycin, enomycin, and the tricothecenes. In certain embodiments, the cytotoxic agent is a radioactive isotope to produce a radioconjugate or a radioconjugated antibody. A variety of radionuclides are available for the production of radioconjugated antibodies including, but not limited to, $^{90}Y$, $^{125}I$, $^{131}I$, $^{123}I$, $^{111}In$, $^{131}In$, $^{105}Rh$, $^{153}Sm$, $^{67}Cu$, $^{67}Ga$, $^{166}Ho$ $^{177}Lu$, $^{186}Re$, $^{188}Re$ and $^{212}Bi$. Conjugates of an antibody and one or more small molecule toxins, such as a calicheamicin, maytansinoids, a trichothene, and CC1065, and the derivatives of these toxins that have toxin activity, can also be used. Conjugates of an antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents.

III. Polynucleotides

In certain embodiments, the invention encompasses polynucleotides comprising polynucleotides that encode a polypeptide that specifically binds a human Jagged or a fragment of such a polypeptide. The term "polynucleotides that encode a polypeptide" encompasses a polynucleotide which includes only coding sequences for the polypeptide as well as a polynucleotide which includes additional coding and/or non-coding sequences. For example, the invention provides a polynucleotide comprising a nucleic acid sequence that encodes an antibody to a human Jagged or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, a polynucleotide comprising a polynucleotide encoding a polypeptide comprising a sequence selected from the group consisting of SEQ ID NO:5, SEQ ID NO:7, SEQ ID NO:19, SEQ ID NO:21, SEQ ID NO:33, SEQ ID NO:35, SEQ ID NO:50, SEQ ID NO:51, and SEQ ID NO:52 is provided. In some embodiments, a polynucleotide sequence encoding a polypeptide (with or without the signal sequence) comprising a sequence selected from the group consisting of SEQ ID NO:1, SEQ ID NO:3, SEQ ID NO:15, SEQ ID NO:17, SEQ ID NO:29, and SEQ ID NO:31 is provided.

In some embodiments, a polynucleotide comprising a nucleotide sequence selected from the group consisting of SEQ ID NO:6, SEQ ID NO:8, SEQ ID NO:20, SEQ ID NO:22, SEQ. ID NO:34, SEQ ID NO:36, SEQ ID NO:53, SEQ ID NO:54, and SEQ ID NO:55 is provided. In some embodiments, a polynucleotide sequence comprising a nucleotide sequence (with or without the signal sequence) selected from the group consisting of SEQ ID NO:2, SEQ ID NO:4, SEQ ID NO:16, SEQ ID NO:18, SEQ ID NO:30, and SEQ ID NO:32 is provided.

In certain embodiments, a polynucleotide comprising a polynucleotide having a nucleotide sequence at least 80% identical, at least 85% identical, at least 90% identical, at least 95% identical, and in some embodiments, at least 96%, 97%, 98% or 99% identical to a polynucleotide comprising a sequence selected from the group consisting of SEQ ID NO:6, SEQ ID NO:8, SEQ ID NO:20, SEQ ID NO:22, SEQ ID NO:34, SEQ ID NO:36, SEQ ID NO:53, SEQ ID NO:54, and SEQ ID NO:55 is provided. In certain embodiments, a polynucleotide comprising a polynucleotide (with or without the signal sequence) having a nucleotide sequence at least 80% identical, at least 85% identical, at least 90% identical, at least 95% identical, and in some embodiments, at least 96%, 97%, 98% or 99% identical to a polynucleotide comprising a sequence selected from the group consisting of SEQ ID NO:2, SEQ ID NO:4, SEQ ID NO:16, SEQ ID NO:18, SEQ ID NO:30 and SEQ ID NO:32 is provided.

Also provided is a polynucleotide that comprises a polynucleotide that hybridizes to SEQ ID NO:6, SEQ ID NO:8, SEQ ID NO:20, SEQ ID NO:22, SEQ ID NO:34, SEQ ID NO:36, SEQ ID NO:53, SEQ ID NO:54 or SEQ ID NO:55, and/or to a polynucleotide encoding a polypeptide having the sequence of SEQ ID NO:5, SEQ ID NO:7, SEQ ID NO:19, SEQ ID NO:21, SEQ NO:33; SEQ ID NO:35, SEQ ID NO:50, SEQ ID NO:51, or SEQ ID NO:52. In certain embodiments, the hybridization is under conditions of high stringency.

In certain embodiments, the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to produce the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification and/or identification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. In some embodiments, the marker sequence is a FLAG-tag, a peptide of sequence DYKDDDK (SEQ ID NO:46) which can be used in conjunction with other affinity tags.

The present invention further relates to variants of the hereinabove described polynucleotides encoding, for example, fragments, analogs, and/or derivatives.

In certain embodiments, the present invention provides polynucleotides comprising polynucleotides having a nucleotide sequence at least 80% identical, at least 85% identical, at least 90% identical, at least 95% identical, and in some embodiments, at least 96%, 97%, 98% or 99% identical to a polynucleotide encoding a polypeptide comprising an antibody, or fragment thereof, to human Jagged described herein.

As used herein, the phrase a polynucleotide having a nucleotide sequence at least, for example, 95% "identical" to a reference nucleotide sequence is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, the polynucleotide variants contain alterations which produce silent substitutions, additions, or deletions, but do not alter the properties or activities of the encoded polypeptide. In some embodiments, polynucleotide variants contain "silent" substitutions due to the degeneracy of the genetic code. Polynucleotide variants can be produced for a variety of reasons, for example, to optimize codon expression for a particular host (e.g., change codons in the human mRNA to those preferred by a bacterial host such as $E.$ $coli$).

In certain embodiments, the polynucleotides as described herein are isolated. In certain embodiments, the polynucleotides as described herein are substantially pure.

Vectors and cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises a polynucleotide molecule.

IV. Methods of Use and Pharmaceutical Compositions

The Jagged-binding agents (e.g., polypeptides and/or antibodies) of the invention are useful in a variety of applications including, but not limited to, therapeutic treatment methods, such as the treatment Of cancer. In certain embodiments, the agents are useful for modulating Jagged activity, inhibiting Jagged activity, inhibiting or blocking Jagged/Notch interactions, inhibiting Notch signaling, and/or inhibiting Notch activation. In some embodiments, the Jagged-binding agents are useful in inhibiting tumor growth, reducing tumor volume, reducing the tumorigenicity of a tumor, reducing the frequency of cancer stem cells in a tumor, inducing death of tumor cells, inducing differentiation, inhibiting angiogenesis, and/or interfering with angiogenesis. The methods of use may be in vitro, ex vivo, or in vivo methods. In certain embodiments, the Jagged-binding agent (e.g., polypeptide and/or antibody) is an antagonist of Jagged1 and/or Jagged2. In certain embodiments, the Jagged-binding agent is an antagonist of a Notch signaling pathway. In some embodiments, the Jagged-binding agent is an antagonist of Notch activation.

In certain embodiments, Jagged-binding agents are used in the treatment of a disease associated with Notch signaling and activation. In particular embodiments, the disease is a disease associated with a Notch signaling pathway. In some embodiments, tumor growth is associated with a Notch signaling pathway. In some embodiments, tumor growth is associated with Notch activation. In some embodiments, the disease is a tumor. In some embodiments, the disease is cancer.

The present invention further provides methods for inhibiting tumor growth using the Jagged-binding agents described herein. In certain embodiments, the method of inhibiting tumor growth comprises contacting tumor cells with a Jagged-binding agent (e.g., an antibody) in vitro. For example, an immortalized cell, line or a cancer cell line that expresses Jagged on the cell surface is cultured in medium to which is added the antibody or other agent to inhibit tumor cell growth. In some embodiments, tumor cells are isolated from a patient sample such as, for example, a tissue biopsy, pleural effusion, or blood sample and cultured in medium to which is added a Jagged-binding agent to inhibit tumor growth.

In some embodiments, the method of inhibiting tumor growth comprises contacting the tumor or tumor cells with a Jagged-binding agent (e.g., an antibody) in vivo. In certain embodiments, contacting a tumor or tumor cells with a Jagged-binding agent is undertaken in an animal model. For example, Jagged-binding agents are administered to immunocompromised mice (e.g., NOD/SCID mice) that have xenograft tumors expressing Jagged1 and/or Jagged2. After administration of Jagged-binding agents, the mice are observed for inhibition of tumor growth. In some embodiments, cancer stem cells are isolated from a patient sample such as, for example, a tissue biopsy, pleural effusion, or blood sample and injected into immunocompromised mice that are then administered a Jagged-binding agent to inhibit tumor growth. In some embodiments, the Jagged-binding agent is administered at the same time or shortly after introduction of tumorigenic cells (CSCs) into the animal to prevent tumor growth. In some embodiments, the Jagged-binding agent is administered as a therapeutic after the tumorigenic cells have grown to a specified size.

In certain embodiments, the method of inhibiting tumor growth comprises administering to a subject a therapeutically effective amount of a Jagged-binding agent. In certain embodiments, the subject is a human. In certain embodiments, the subject has a tumor. In certain embodiments, the subject has had a tumor removed. In some embodiments, the Jagged-binding agent is an antibody. In some embodiments, the Jagged-binding agent is antibody 64M51, 64R7, 64R1B, 133R0201, 133R0203, or 133R0205. In some embodiments, the Jagged-binding agent is not antibody 64M14.

In certain embodiments, the tumor expresses Jagged1 and/or Jagged2 to which the Jagged-binding agent or antibody binds. In certain embodiments, the tumor over-expresses a human Jagged1 and/or Jagged2. In certain embodiments, the tumor expresses a Notch receptor (e.g., Notch1, Notch2, Notch3 and/or Notch4) with which Jagged interacts. In some embodiments, the Jagged-binding agent binds to Jagged and inhibits or reduces growth of the tumor. In some embodiments, the Jagged-binding agent binds to Jagged, interferes with Jagged/Notch interactions and inhibits or reduces growth of the tumor. In some embodiments, the Jagged-binding agent binds to Jagged, inhibits Notch activation and inhibits or reduces growth of the tumor. In some embodiments, the Jagged-binding agent binds to Jagged, and reduces the frequency of cancer stem cells in the tumor. In certain embodiments, the Jagged-binding agent binds to Jagged and inhibits or reduces angiogenesis. In certain embodiments, the inhibition and/or reduction of angiogenesis inhibits or reduces growth of the tumor.

In certain embodiments, the tumor is a tumor selected from the group consisting of colorectal tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is a colorectal tumor. In certain embodiments, the tumor is a pancreatic tumor. In certain embodiments, the tumor is a breast tumor. In certain embodiments, the tumor is a prostate tumor. In certain embodiments, the tumor is a lung tumor. In certain embodiments, the subject is a human.

The present invention further provides methods for treating cancer using the Jagged-binding agents described herein. In certain embodiments, the cancer is characterized by cells expressing. Jagged1 and/or Jagged2 to which the Jagged-binding agent (e.g., antibody) binds. In certain embodiments, the cancer over-expresses a human Jagged1 and/or Jagged2. In certain embodiments, the cancer is characterized by cells expressing Notch receptors, wherein the Jagged-binding agent (e.g., an antibody) interferes with Jagged-induced Notch signaling and/or activation. In some embodiments, the Jagged-binding agent binds to Jagged and inhibits or reduces growth of the cancer. In some embodiments, the Jagged-binding agent binds to Jagged, interferes with Jagged/Notch interactions and inhibits or reduces growth of the cancer. In some embodiments, the Jagged-binding agent binds to Jagged, inhibits Notch activation and inhibits or reduces growth of the cancer. In some embodiments, the Jagged-binding agent binds to Jagged, and reduces the frequency of cancer stem cells in the cancer. In certain embodiments, the Jagged-binding agent binds to Jagged and inhibits or reduces angiogenesis. In certain embodiments, the inhibition and/or reduction of angiogenesis inhibits or reduces growth of the cancer.

The present invention provides for methods of treating cancer comprising administering a therapeutically effective amount of a Jagged-binding agent to a subject (e.g., a subject in need of treatment). In certain embodiments, the subject is a human. In certain embodiments, the subject has a cancerous tumor. In certain embodiments, the subject has had a tumor removed. In some embodiments, the Jagged-binding agent is an antibody. In some embodiments, the Jagged-binding agent is antibody 64M51, 64R7, 64R1B, 133R0201, 133R0203 or 133R0205. In some embodiments, the Jagged-binding agent is not antibody 64M14.

In certain embodiments, the cancer is a cancer selected from the group consisting of colorectal cancer, pancreatic cancer, lung cancer, ovarian cancer, liver cancer, breast cancer, kidney cancer, prostate cancer, gastrointestinal cancer, melanoma, cervical cancer, bladder cancer, glioblastoma, and head and neck cancer. In certain embodiments, the cancer is pancreatic cancer. In certain embodiments, the cancer is colorectal cancer. In certain embodiments, the cancer is breast cancer. In certain embodiments, the cancer is prostate cancer. In certain embodiments, the cancer is lung cancer.

The invention also provides a method of inhibiting Notch signaling or Notch activation in a cell comprising contacting the cell with an effective amount of a Jagged-binding agent. In certain embodiments, the cell is a tumor cell. In certain embodiments, the method is an in vivo method wherein the step of contacting the cell with the Jagged-binding agent comprises administering a therapeutically effective amount of the Jagged-binding agent to the subject. In some embodiments, the method is an in vitro or ex vivo method. In certain embodiments, the Jagged-binding agent inhibits Notch signaling. In some embodiments, the Jagged-binding agent inhibits Notch activation. In certain embodiments, the Jagged-binding agent interferes with a Jagged/Notch interaction. In certain embodiments, the Notch signaling is signaling by Notch1, Notch2, Notch3, and/or Notch4. In some embodiments, the Jagged-binding agent is an antibody. In some embodiments, the Jagged-binding agent is antibody 64M51, 64R7, 64R1B, 133R0201, 133R0203, or 133R0205. In some embodiments, the Jagged-binding agent is not antibody 64M14.

In addition, the invention provides a method of reducing the tumorigenicity of a tumor in a subject, comprising administering a therapeutically effective amount of a Jagged-binding agent to the subject. In certain embodiments, the tumor comprises cancer stem cells. In certain embodiments, the frequency of cancer stem cells in the tumor is reduced by administration of the Jagged-binding agent. The invention also provides a method of reducing the frequency of cancer stem cells in a tumor, comprising contacting the tumor with an effective amount of a Jagged-binding agent (e.g., an anti-Jagged antibody). In some embodiments, the Jagged-binding agent is antibody 64M51, 64R7, 64R1B, 133R0201, 133R0203, or 133R0205. In some embodiments, the Jagged-binding agent is not antibody 64M14.

The invention also provides a method of treating a disease or disorder in a subject, wherein the disease or disorder is characterized by an increased level of stem cells and/or progenitor cells. In some embodiments, the treatment methods comprise administering a therapeutically effective amount of the Jagged-binding agent, polypeptide, or antibody to the subject.

The present invention further provides pharmaceutical compositions comprising one or more of the Jagged-binding agents described herein. In certain embodiments, the pharmaceutical compositions further comprise a pharmaceutically acceptable vehicle. These pharmaceutical compositions find use in inhibiting tumor growth and treating cancer in a subject (e.g., a human patient).

In certain embodiments, formulations are prepared for storage and use by combining a purified antibody or agent of the present invention with a pharmaceutically acceptable vehicle (e.g., a carrier or excipient). Suitable pharmaceutically acceptable vehicles include, but are not limited to, non-toxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (Remington: The Science and Practice of Pharmacy, 21$^{st}$ Edition, University of the Sciences in Philadelphia, 2005).

The pharmaceutical compositions of the present invention can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present invention, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

The Jagged-binding agents or antibodies described herein can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in Remington: The Science and Practice of Pharmacy, 21$^{st}$ Edition, University of the Sciences in Philadelphia, 2005.

In certain embodiments, pharmaceutical formulations include Jagged-binding agents (e.g., an antibody) of the present invention complexed with liposomes. Methods to produce liposomes are known to those of skill in the art. For example, some liposomes can be generated by reverse phase evaporation with, a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations can be produced. Suitable examples of sustained-release preparations include semi-permeable matrices of solid hydrophobic polymers containing the Jagged-binding agent (e.g., an antibody), where the matrices are in the form of shaped articles (e.g., films or microcapsules). Examples of sustained-release matrices include polyesters, hydrogels such as poly (2-hydroxyethyl-methacrylate) or polyvinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

In certain embodiments, in addition to administering a Jagged-binding agent, the method or treatment further comprises administering at least one additional therapeutic agent. An additional therapeutic agent can be administered prior to, concurrently with, and/or subsequently to, administration of the Jagged-binding agent. Pharmaceutical compositions comprising the Jagged-binding agent and the additional therapeutic agent(s) are also provided. In some embodiments, the at least one additional therapeutic agent comprises 1, 2, 3, or more additional therapeutic agents.

Combination therapy with at least two therapeutic agents often involves agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects. Combination therapy may decrease the likelihood that resistant cancer cells will develop. Combination therapy may allow for one therapeutic agent to be targeted to tumorigenic cancer stem cells, while a second therapeutic agent may be targeted to non-tumorigenic cancer cells.

It will be appreciated that the combination of a Jagged-binding agent and an additional therapeutic agent may be administered in any order or concurrently. In some embodiments, the Jagged-binding agents will be administered to patients that have previously undergone treatment with a second therapeutic agent. In certain other embodiments, the Jagged-binding agent and a second therapeutic agent will be administered substantially simultaneously or concurrently. For example, a subject may be given the Jagged-binding agent (e.g., an antibody) while undergoing a course of treatment with a second therapeutic agent (e.g., chemotherapy). In certain embodiments, the Jagged-binding agent will be administered within 1 year of the treatment with a second therapeutic agent. In certain alternative embodiments, the Jagged-binding agent will be administered within 10, 8, 6, 4, or 2 months of any treatment with a second therapeutic agent. In certain other embodiments, the Jagged-binding agent will be administered within 4, 3, 2, or 1 weeks of any treatment with a second therapeutic agent. In some embodiments, the Jagged-binding agent will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

Useful classes of therapeutic agents include, for example, antitubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In certain embodiments, the second therapeutic agent is an antimetabolite, an antimitotic, a topoisomerase inhibitor, or an angiogenesis inhibitor.

Therapeutic agents that may be administered in combination with the Jagged-binding agents include chemotherapeutic agents. Thus, in some embodiments, the method or treatment involves the combined administration of a Jagged-binding agent or antibody of the present invention and a chemotherapeutic agent or cocktail of multiple different chemotherapeutic agents. Treatment with an antibody can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

Chemotherapeutic agents useful in the instant invention include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including, altretamine, triethylenemelamine, trietylenephosphoramide, triethylenethiophosphaoramide and trimethylolomelamime; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethane; vindesine; dacarbazine; mannomustine; mitobronitol; mitolactol; pipobroman; gacytosine; arabinoside ("Ara-C"); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylomithine (DMFO); retinoic acid; esperamicins; capecitabine; and pharmaceutically acceptable salts, acids or derivatives of any of the above. Chemotherapeutic agents also include anti-hormonal agents that act to regulate or inhibit hormone action on, tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In certain embodiments, the second therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, THIOGUANINE, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the second therapeutic agent is gemcitabine.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments; the agent is paclitaxel (TAXOL), docetaxel (TAXOTERE), albumin-bound paclitaxel (ABRAXANE), DHA-paclitaxel, or PG-paclitaxel. In certain alternative embodiments, the antimitotic agent comprises a vinca alkaloid, such as vincristine, binblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, where the chemotherapeutic agent administered in combination with the Jagged-binding agent is an anti-mitotic agent, the cancer or tumor being treated is breast cancer or a breast tumor.

In certain embodiments, the treatment involves the combined administration of a Jagged-binding agent (e.g. an antibody) of the present invention and radiation therapy. Treatment with the Jagged-binding agent can occur prior to, concurrently with, or subsequent to administration of radiation therapy. Dosing schedules for such radiation therapy can be determined by the skilled medical practitioner.

In some embodiments, a second therapeutic agent comprises an antibody. Thus, treatment can involve the combined administration of a Jagged-binding agent (e.g. an antibody) of the present invention with other antibodies against additional tumor-associated antigens including, but not limited to, antibodies that bind to EGFR, ErbB2, HER2, DLL4, Notch and/or VEGF. Exemplary, anti-DLL4 antibodies, are described, for example, in U.S. Patent Application Pub. No. 2008/0187532. Additional anti-DLL4 antibodies are described in, e.g., International Patent Pub. Nos. WO 2008/091222 and WO 2008/0793326, and U.S. Patent Application Pub. Nos.

2008/0014196; 2008/0175847; 2008/0181899; and 2008/0107648. Exemplary anti-Notch antibodies, are described, for example, in U.S. Patent Application Pub. No. 2008/0131434. In certain embodiments, a second therapeutic agent is an antibody that is an angiogenesis inhibitor (e.g., an anti-VEGF antibody). In certain embodiments, a second therapeutic agent is bevacizumab (AVASTIN), trastuzumab (HERCEPTIN), panitumumab (VECTIBIX), or cetuximab (ERBITUX). Combined administration can include co-administration, either in a single pharmaceutical formulation or using separate formulations, or consecutive administration in either order but generally within a time period such that all active agents can exert their biological activities simultaneously.

Furthermore, treatment with the Jagged-binding agents described herein can include combination treatment with one or more cytokines (e.g., lymphokines, interleukins, tumor necrosis factors, and/or growth factors) or can be accompanied by surgical removal of tumors, cancer cells or any other therapy deemed necessary by a treating physician.

For the treatment of the disease, the appropriate dosage of an Jagged-binding agent (e.g., an antibody) of the present invention depends on the type of disease to be treated, the severity and course of the disease, the responsiveness of the disease, whether the Jagged-binding agent or antibody is administered for therapeutic or preventative purposes, previous therapy, the patient's clinical history, and so on, all at the discretion of the treating physician. The Jagged-binding agent or antibody can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody or agent. The administering physician can easily determine optimum dosages, dosing methodologies and repetition rates. In certain embodiments, dosage is from 0.01 µg to 100 mg per kg of body weight, and can be given once or more daily, weekly, monthly or yearly. In certain embodiments, the antibody or other Jagged-binding agent is given once every two weeks or once every three weeks. In certain embodiments, the dosage of the antibody or other Jagged-binding agent is from about 0.1 mg to about 20 mg per kg of body weight. The treating physician can estimate repetition rates for dosing based on measured residence times and concentrations of the drug in bodily fluids or tissues.

EXAMPLES

Example 1

Generation of Anti-Jagged Monoclonal Antibodies

Antibodies were generated against an extracellular domain of mouse Jagged1. Standard recombinant DNA technology was used to isolate polynucleotides encoding the extracellular domain of mouse Jagged1 (aa 1-1060) and were separately ligated in-frame to a histidine-tag. This polynucleotide construct was cloned into a transfer plasmid vector for baculovirus-mediated expression in insect cells. Standard transfection, infection, and cell culture protocols were used to produce recombinant insect cells expressing the mouse Jagged1 polypeptide corresponding to the extracellular domain of mouse Jagged1 comprising amino acids 1-1060 with the histidine tag (SEQ ID NO:45) (O'Reilly et al., 1994, Baculovirus Expression Vectors: A Laboratory Manual, Oxford: Oxford University Press).

The extracellular domain of mouse Jagged1 polypeptide with His-tag was purified from insect cell supernatant using $Ni^{++}$-chelate affinity chromatography as known to one skilled in the art. Purified mouse Jagged1 polypeptide was dialyzed against PBS (pH=7), concentrated to approximately 1 mg/ml, and sterile filtered in preparation for immunization.

Mice (n=3) were immunized with the purified mouse Jagged1 antigen protein described above using standard techniques. Blood from individual mice was screened approximately 70 days after initial immunization for antigen recognition using FACS analysis (as described herein). The animal with the highest antibody titer for blocking Notch2-Fc binding to human Jagged1-expressing HEK293 cells was selected for final antigen boost after which spleen cells were isolated for hybridoma production. Hybridoma cells were plated at 1 cell per well in 96 well plates, and the supernatant from each well screened by FACS analysis for reactivity to human Jagged1 polypeptide and for the ability to block Notch2-Fc binding to human Jagged1-expressing HEK293 cells. Several hybridomas with high antibody titer were selected and scaled up as ascites in Balb/c mice. Antibodies were purified from the hybridoma supernatants or ascites using protein A or protein G agarose chromatography. Purified monoclonal antibodies were assayed again by FACS as described herein. Antibodies were analyzed for binding to HEK293 cells expressing human Jagged1, mouse Jagged1, human Jagged2 or mouse Jagged2. The antibodies were also tested for their ability to block human Notch2-Fc binding to HEK293 cells expressing human Jagged1, mouse Jagged1, human Jagged2 or mouse Jagged2. Several antibodies that recognized the extracellular domain of human Jagged1 and mouse Jagged1 and/or Jagged2 were isolated. A hydridoma cell line expressing antibody 64M51 was deposited with ATCC under the conditions of the Budapest Treaty on Nov. 13, 2009 and assigned ATTC Patent Deposit Designation [ ]. The nucleotide and predicted protein sequences of both the heavy chain (SEQ ID NO:2 (nt) and SEQ ID NO:1 (aa)) and light chain (SEQ ID NO:4 (nt) and SEQ ID NO:3 (aa)) of antibody 64M51 were determined.

Example 2

Generation of Human Anti-Jagged Antibodies

Human antibodies that specifically recognize Jagged can be isolated using phage display. For example, a synthetic antibody library containing human antibody variable domains may be panned for specific and high affinity recognition of the extracellular domain of human Jagged1. Once a specific Fab with the desired characteristics has been identified, the human variable regions of the Fab are cloned into an Ig expression vector containing a human IgG2 heavy chain and a human light chain (kappa or lambda) for expression of human antibodies in CHO cells.

Phage display was used to identify specific Fabs that bind to the extracellular domain of human Jagged1. $2 \times 10^{13}$ Fab displaying phage particles from a human Fab phage library were incubated with passively immobilized recombinant human Jagged1 ECD protein fused with a human Fc domain. The non-binding phage were washed off, phage bound to the Jagged1 protein were eluted with 100 mM glycine, 500 nM NaCl pH2.2 and the elutant was neutralized with 1/10 volume of 2M Tris base. The eluted output phage were used to infect TG1 F+ bacteria and rescued with helper phage. The output of rescued round one served as the starting point for further selection rounds. The selections were continued to round 3, and then the output was screened in ELISA for Fabs specifically binding to recombinant human Jagged1 ECD-Fc protein. Several Fabs that specifically bound to human Jagged1 were identified.

The sequences of the variable regions of two of the identified Fabs were determined. The amino acid sequence of the Fab 64R7 heavy chain variable region is provided as SEQ ID NO:19 and the nucleotide sequence as SEQ ID NO:20. The amino acid sequence of the Fab 64R7 light chain variable region is provided as SEQ ID NO:21 and the nucleotide sequence as SEQ ID NO:22. The amino acid sequence of the Fab 64R1B heavy chain variable region is provided as SEQ ID NO:33 and the nucleotide sequence as SEQ ID NO:34. The amino acid sequence of Fab 64R1B light chain variable region is provided as SEQ Ti) NO:35 and the nucleotide sequence as SEQ ID NO:36. The heavy chain and light chain CDR sequences of 64R7 and 64R1B, as well as 64M51 are shown below in Table 2.

Jagged2 and (2) the transfection marker GFP. Twenty-four to forty-eight hours post-transfection, cells were collected in suspension and incubated on ice with anti-Jagged antibodies (10 μg/ml unless otherwise indicated) or control IgG to detect background antibody binding. The cells were washed in PBS and bound antibodies were detected with PE-conjugated anti-human Fc secondary antibodies. Labeled cells were analyzed by flow cytometry to identify anti-Jagged antibodies that specifically recognized cell surface expression of Jagged protein. Several monoclonal antibodies that recognized Jagged1 were identified and included antibodies 64M51, 64R7 and 64R1B.

As shown in FIG. 1, 64M51 and 64R7 antibodies bound to human Jagged1 and human Jagged2. In contrast, 64R1B bound specifically to human Jagged1 but did not bind human Jagged2. 64M51 antibodies also bound to mouse Jagged1 and mouse Jagged2, while 64R7 bound to mouse Jagged1 and weakly to Jagged2. Similar to the binding pattern seen with

TABLE 2

|  | 64M51 | 64R7 | 64R1B |
|---|---|---|---|
| Heavy Chain CDR1 | SYWIH (SEQ ID NO: 9) | SYAMH (SEQ ID NO: 23) | SSNWWS (SEQ ID NO: 37) |
| Heavy Chain CDR2 | RIYPGIGSTYYNEKFKD (SEQ ID NO: 10) | VISYDGSNKYYADSVKG (SEQ ID NO: 24) | EIFHGENTNYNPELKS (SEQ ID NO: 38) |
| Heavy Chain CDR3 | NGGFFDY (SEQ ID NO: 11) | DKYDIPDAFDI (SEQ ID NO: 25) | NPGIGAAKFDS (SEQ ID NO: 39) |
| Light Chain CDR1 | RASESVDSYGNSFMH (SEQ ID NO: 12) | RASQGISNDLA (SEQ ID NO: 26) | KSSQSLLHSDGKTYLY (SEQ ID NO: 40) |
| Light Chain CDR2 | RASNLES (SEQ ID NO: 13) | ATSTLQS (SEQ ID NO: 27) | EVSNRFS (SEQ ID NO: 41) |
| Light Chain CDR3 | QQSNDPWT (SEQ ID NO: 14) | QQSYNAPI (SEQ ID NO: 28) | MQHIDFP (SEQ ID NO: 42) |

The human variable regions of the 64R7 and 64R1B Fabs were cloned into Ig expression vectors containing human IgG2 heavy chain and human light chain (kappa) regions for expression in CHO cells using standard methods known to one skilled in the art. The amino acid sequences of the heavy chain and light chain of the 64R7 IgG antibody (including signal sequences) are provided in SEQ ID NO:15 and SEQ ID NO:17, respectively. The signal sequence at the N-terminus of the amino acid sequence of each of the chains is cleaved upon secretion. The nucleic acid sequences encoding the heavy and light chains of the 64R7 IgG antibody (including signal sequences) are provided in SEQ ID NO:16 and SEQ ID NO:18, respectively. The amino acid sequences of the heavy chain and light chain of the 64R1B IgG antibody (including signal sequence) are provided in SEQ ID NO:29 and SEQ ID NO:31, respectively. (Again, the signal sequence at the N-terminus of the amino acid sequence of each of the chains is cleaved upon secretion.) The nucleic acid sequences encoding the heavy and light chains of the 64R1B IgG antibody (including signal sequence) are provided in SEQ ID NO:30 and SEQ ID NO:32, respectively.

Example 3

FACS Analysis of Anti-Jagged1 Antibodies

Human HEK293 cells were co-transfected with expression vectors encoding (1) full-length cDNA for human Jagged1 or human Jagged, 64R1B bound specifically to mouse Jagged 1, and did not bind to mouse Jagged2.

To determine the effect of anti-Jagged antibodies on Jagged ligand binding to Notch receptors, a FACS-based assay was used. Human HEK293 cells were transfected with expression vectors encoding full-length cDNA for human Jagged1 or Jagged2, along with an expression vector encoding GFP. Transfected cells were incubated with recombinant Notch2-Fc fusion protein (containing the amino acids 375-608 of human Notch2 fused to the Fc region of human IgG1) in the presence or absence of 64M51, 64R7, 64R1B and 64M14 antibodies. Cells were washed in PBS and the binding of Notch2-Fc to transfected cells was detected by incubation with PE-conjugated anti-human Fc secondary antibody and analyzed by flow cytometry as described above.

As shown in FIG. 2, 64M51 and 64R7 antibodies blocked the binding of Notch2-Fc to both Jagged1 and Jagged2-expressing cells. In contrast, 64M14 antibodies blocked the binding of Notch2-Fc to Jagged1-expressing cells but did not block binding of Notch2-Fc to Jagged2-expressing cells. 64R1B antibodies did not show Jagged-Notch2 interaction blocking activity against either Jagged1 or Jagged2-expressing cells in this assay.

Example 4

Binding Affinities

The $K_D$s of 64M51, 64R7 and 64R1B antibodies were determined using a Biacore 2000 system from Biacore Lifescience (GE Healthcare). Recombinant Jagged proteins human Jagged1-Fc (hJag1), mouse Jagged1-His (mJag1), human Jagged2-Fc (hJag2) and mouse Jagged2-Fc (mJag2) were immobilized a CM5 chip using standard amine-based chemistry (NHS/EDC). Antibodies were serially diluted in 2-fold increments from 100 to 1.0 nM in HBS-P (0.01M HEPES pH7.4, 0.15M NaCl, 0.005% v/v Surfactant P20) and were injected over the chip surface. Kinetic data were collected over time and were fit using the simultaneous global fit equation to yield affinity constants ($K_D$ values) for each antibody (Table 3).

TABLE 3

| Ab | hJag1 (nM) | mJag1 (nM) | hJag2 (nM) | mJag2 (nM) |
|---|---|---|---|---|
| 64M51 | 30 | 33 | 6.2 | 7.9 |
| 64R7 | 5.9 | 10.5 | 8.3 | 20.6 |
| 64R1B | 0.61 | 0.82 | NB* | NB* |

*NB = No binding detected at 100 nM

64M51 bound to both human and mouse Jagged1 and Jagged2, with the antibody demonstrating a higher affinity for Jagged2 in this assay. 64R7 bound to both human and mouse Jagged1 and Jagged2, with the antibody having a slightly higher affinity for the human Jaggeds over the mouse Jaggeds in this assay. 64R1B bound only to Jagged1 and bound to both human and mouse Jagged1 with similar affinities.

Example 5

Epitope Competition Assays

The antibodies were analyzed to determine whether they had distinct or non-overlapping epitopes. Each antibody (64R1B, 64R7 and 64M51) was immobilized on a CM5 chip (chip antibody) and then 10 μg/ml of recombinant monovalent human Jagged1 protein was flowed over the surface. Immediately after injection of Jagged1, one of the three antibodies (solution antibody) was flowed over the same surface (chip antibody+Jagged1) at 100 nM concentration. If the chip-bound and solution antibodies bind the same epitope, then the solution antibody should not bind the surface, e.g. chip and solution antibodies bind the same (or an over-lapping) Jagged epitope. In other words, the Jagged1 epitope is already occupied by binding to the first chip antibody and not available to bind to a second antibody. On the other hand, if the first antibody (chip antibody) and the second antibody (solution antibody) have their own distinct or non-overlapping epitopes, the solution antibody should bind to the surface. The Jagged epitope recognized by the second antibody is free to be bound by that second antibody.

For evaluating the binding curves, if the solution antibody maximal binding signal is greater than both the buffer control (Buffer) and the self antibody control (solution antibody=chip antibody), then the solution antibody is scored as (+) and has a distinct or non-overlapping epitope. If the solution antibody maximal binding signal is greater than the buffer control but less than the self antibody control, then the solution antibody is scored as (+/−) and may have a partially overlapping epitope with the chip antibody. If the solution antibody maximal binding signal is equivalent or less than both the buffer and self antibody control, then the solution antibody is scored as a (−) and has an overlapping epitope with the chip antibody.

As shown in FIG. 3 and summarized in Table 4, antibodies 64M51, 64R7 and 64R1B appear to bind distinct epitopes. Following binding of human Jagged1 to each of the indicated antibody chips, 64R1B (FIG. 3A), 64R7 (FIG. 3B) and 64M51 (FIG. 3C), further subsequent binding of that antibody (e.g., further binding of 64R1B to a chip that had been initially coated with 64R1B) to the chip was limited, (i.e., very weak or non-detectable). In contrast, robust binding of the other two Jagged antibodies was readily observed, indicating that each of these anti-Jagged antibodies appears to bind to a distinct epitope.

TABLE 4

| | Solution Antibody | | |
|---|---|---|---|
| Chip Antibody | 64R1B | 64R7 | 64M51 |
| 64R1B | − | + | + |
| 64R7 | + | +/− | + |
| 64M51 | + | + | +/− |

Example 6

Reporter Assays

The ability of anti-Jagged antibodies to inhibit Notch activation was investigated using a Notch-dependent luciferase reporter assay. Recombinant fusion proteins containing the extracellular domain of either human Jagged1 or rat Jagged1 fused to human Fc were generated by standard recombinant methods. Fusion proteins containing the extracellular domain of either human Jagged2 or mouse Jagged2 fused to human Fc were generated by standard recombinant methods. Human PC3 cells were transfected with an expression vector encoding a full-length Notch2 receptor as well as plasmids encoding a Notch-dependent firefly luciferase reporter construct (8xCBF-luciferase) and a Renilla luciferase reporter (Promega, Madison, Wis.) as an internal control for transfection efficiency. Purified Jagged proteins were coated onto 96 well plates at 400 ng per well, and Notch2-expressing PC3-luc cells were added to the wells. 64M51, 64R7 and 64R1B antibodies were serially diluted 1:4 from 40 to 0.039 μg/ml, added to the appropriate wells and incubated overnight. Luciferase activity was determined 18 hours later using a dual luciferase assay kit (Promega, Madison, Wis.) with firefly luciferase activity normalized to Renilla luciferase activity.

64R7 and 64R1B inhibited human Jagged1-induced Notch2 activation at similar levels, while 64M51 did not inhibit human Jagged1-induced Notch2 activation (FIG. 4A). 64R1B inhibited rat Jagged1-induced Notch2 activation at a higher level than 64R7, while 64M51 did not inhibit rat Jagged 1-induced Notch2 activation (FIG. 4C). 64R7 inhibited human Jagged2-induced Notch2 activation, while 64R1B did not inhibit human Jagged2-induced Notch2 activation. There appeared to be partial inhibition of human Jagged2-induced Notch2 activation by 64M51 (FIG. 4B). 64R7 inhibited mouse Jagged2-induced Notch2 activation, while 64R1B did not inhibit mouse Jagged2-induced Notch activation. 64M51 inhibited mouse Jagged2-induced Notch2 activations, but at a higher concentration of antibody than 64R7 (FIG. 4D).

The ability of Jagged antibodies to inhibit Jagged-induced Notch signaling was also investigated using a two cell population assay format. One population of human PC3 cells was transfected with an expression vector encoding a full-length Notch2 receptor as well as plasmids encoding a Notch-dependent firefly luciferase reporter construct (8xCBF luciferase) and a Renilla luciferase reporter (Promega, Madison Wis.) as an internal transfection control. A second population of human PC3 cells was transfected with an expression vector encoding a full-length cDNA for either hJagged1 or hJagged2. Aliquots of the two cell populations were mixed together and incubated overnight in the presence of 64M51, 64R7 or 64R1B antibodies that were serially diluted 1:4 from 40 to 0.0394 ml. Luciferase levels were measured 18 hours later using a dual luciferase assay kit (Promega, Madison, Wis.) with firefly luciferase activity normalized to Renilla luciferase activity. Shown is a titration of 64M51, 64R1B and 64R7 antibodies in this assay. 64R1B was shown to be a potent inhibitor of human Jagged1-induced Notch2 activation, while 64R7 was shown to be an inhibitor of both human Jagged1 and human Jagged2-induced Notch activation (FIGS. 5A and 5B).

Example 7

Evaluation of Anti-Tumor Activity of Anti-Jagged Antibodies, Alone or in Combination with Taxol in a Breast Tumor Xenograft Model PE13 breast tumor cells were injected subcutaneously into the mammary fat pads of NOD/SCID mice. 10,000 cells were injected per animal. Mice were monitored weekly and tumors were allowed to grow until they were approximately 170 mm$^3$. The mice were randomized into four treatment groups (n=10 mice/group) and treated with either control antibody (LZ-1, directed against bacterial lysozyme), anti-Jagged 64M51, taxol or a combination of 64M51 and taxol. Taxol was administered intraperitoneally at a dose of 7.5 mg/kg once a week and antibodies were administered intraperitoneally at a dose of 15 mg/kg twice a week. Tumor measurements were made on the days indicated in FIG. 6.

Treatment with, antibody 64M51 was observed to reduce tumor growth as a single agent relative to the control antibody group, and to a level similar to taxol treatment. In addition, treatment with the combination of 64M51 and taxol reduced tumor growth to a level greater that either agent alone (FIG. 6).

Example 8

Evaluation of Anti-Tumor Activity of Anti-Jagged Antibodies, Alone or in Combination with Gemcitabine in a Pancreatic Xenograft Model PN17 pancreatic tumor cells were injected subcutaneously into the flanks of NOD/SCID mice. 10,000 cells were injected per animal. Mice were monitored weekly and tumors were allowed to grow until they were approximately 145 mm$^3$; The mice were randomized into four treatment groups (n=10 mice/group) and treated with either control antibody (LZ-1), anti-Jagged 64M51, gemcitabine or a combination of 64M51 and gemcitabine. Gemcitabine was administered intraperitoneally at a dose of 5 mg/kg once a week and antibodies were administered intraperitoneally at a dose of 15 mg/kg twice a week. Tumor measurements were made on the days indicated in FIG. 7.

Treatment with antibody 64M51 showed no significant reduction in tumor growth relative to the control antibody (FIG. 7A). Treatment with gemcitabine resulted in a transient initial response as demonstrated by the slowing and slight reduction in tumor volume, but tumor growth resumed subsequently. In contrast, treatment with the combination of gemcitabine plus 64M51 resulted in a prolonged reduction in tumor growth (FIG. 7B).

Example 9

Pharmacokinetics of 64R7 and 64R1B

The pharmacokinetics of 64R7 and 64R1B were assessed in rats in a' one week pharmacokinetics (PK) study using doses of 10 mg/kg and 30 mg/kg. Sprague Dawley rats, five males in each group, were dosed with 64R7 or 64R1B via the tail vein at 10 mg/kg or 30 mg/kg and followed for one week with samples collected at the time points 1, 24, 48, 72, 96, and 168 hours. At each time point, 1 mL of blood was collected into potassium-EDTA tubes and centrifuged. The plasma supernatants were collected and frozen until the samples were analyzed.

The level of antibodies 64R7 or 64R1B present in the plasma at each time point was quantified and the half-life was calculated for the two doses (FIG. 8). Antibody 64R1B at a dose of 10 mg/kg was determined to have a half-life of 123 hours and at a dose of 30 mg/kg was determined to have a half-life of 129 hours. Antibody 64R7 at a dose of 10 mg/kg was determined to have a half-life of 75 hours and at a dose of 30 mg/kg was determined to have a half-life of 115 hours.

Example 10

Inhibition of Tumor Growth by 64R7 in Lung Tumor Xenograft Model

The anti-tumor activity of antibody 64R7 was evaluated in the lung Lu11 tumor xenograft model. Dissociated OMP-Lu11 cells (10,000 per animal) were injected subcutaneously into 6-8 week old male NOD/SCID mice. Tumor growth was monitored weekly and tumor measurements were initiated once tumors were palpable. On day 45, mice with average tumor volumes of 144 mm$^3$ were randomized into 4 groups of 10 animals each. Animals were injected with either control antibody, 64R7 antibody (40 mg/kg), taxol (15 mg/kg) or a combination of 64R7 antibody and taxol. Administration of the antibodies and taxol was performed via injection into the intraperitoneal cavity, twice weekly for the antibodies and once a week for taxol. Tumors were measured twice a week and tumor volume was determined using the formula ½(a× b$^2$); where a=length, and b=breadth. Data are expressed as mean and mean±S.E.M. Group means were compared using Student's two-tailed, unpaired t test. Probability (p) values of <0.05 were interpreted as significantly different.

Treatment with antibody 64R7 resulted in a 29% reduction in tumor growth, as shown in FIG. 9 (p=0.04). Furthermore, treatment with a combination of antibody 64R7 and taxol resulted in a 36% reduction of tumor growth relative to treatment with taxol alone (p<0.001 vs. taxol alone) (FIG. 9). Thus, antibody 64R7 demonstrated anti-tumor growth activity in the Lu11 lung tumor model as a single agent as well as in combination with taxol.

Example 11

Evaluation of Anti-Tumor Activity of Anti-Jagged Antibody 64R7 in Colon Xenograft Model The anti-tumor activity of antibody 64R7 was evaluated in the colon C28 tumor xenograft model. Dissociated OMP-C28 cells (10,000 per animal) were injected subcutaneously into the flanks of 6-8 week old male NOD/SCID mice. Tumor growth was monitored weekly and tumor measurements were initiated once tumors were palpable. On day 31, mice with average tumor volumes of 128 mm$^3$ were randomized into 4 groups of 1.0 animals each. Animals were injected with either control antibody (LZ-1, 15 mg/kg), 64R7 (15 mg/kg), irinotecan (7.5 mg/kg) or a combination of 64R7 and irinotecan. Administration of the antibodies and irinotecan was performed via injection into the intra-peritoneal cavity, twice weekly for antibodies, and once weekly for irinotecan. Tumors were measured twice a week and tumor volume was determined using the formula $\frac{1}{2}(a \times b^2)$; where a=length, and b=breadth. Data are expressed as mean and mean±S.E.M. Group means were compared using Student's two-tailed, unpaired t test. Probability (p) values of <0.05 were interpreted as significantly different.

Treatment with antibody 64R7 resulted in a 37% reduction in tumor growth, as shown in FIG. 10 (p<0.001). Furthermore, treatment with a combination of antibody 64R7 and irinotecan resulted in a 20% reduction of tumor growth relative to treatment with irinotecan alone (p=0.02) (FIG. 10). Thus, antibody 64R7 demonstrated anti-tumor growth activity in the C28 colon tumor xenograft model both as a single agent and in combination with irinotecan.

Example 12

Evaluation of Anti-Tumor Activity of Anti-Jagged Antibody 64R7 in Lung Xenograft Model The anti-tumor activity of 64R7 was evaluated in the lung Lu45 tumor xenograft model. Dissociated OMP-Lu45 cells (50,000 per animal) were injected subcutaneously into 6-8 week old male NOD/SCID mice. Tumor growth was monitored weekly and tumor measurements were initiated once tumors were palpable. On day 39, mice with average tumor volumes of 187 mm$^3$ were randomized into 2 groups of 7 animals each. Animals were injected with either taxol alone (15 mg/kg), or a combination of antibody 64R7 (40 mg/kg) and taxol (15 mg/kg). Administration of antibody 64R7 and taxol was performed via injection into the intra-peritoneal cavity, once weekly. Tumors were measured twice a week and tumor volume was determined using the formula $\frac{1}{2}(a \times b^2)$; where a=length, and b=breadth. Data are expressed as mean and mean±S.E.M. Group means were compared using Student's two-tailed, unpaired t test. Probability (p) values of <0.05 were interpreted as significantly different.

Treatment with a combination of antibody 64R7 and taxol resulted in a 42% reduction in tumor growth as compared to treatment with taxol alone, as shown in FIG. 11A (p=0.04). Thus, antibody 64R7 demonstrated anti-tumor growth activity in the Lu45 lung tumor model in combination with taxol.

Limiting dilution assays (LDA) can be used to assess the effect of therapeutic agents on solid tumor cancer stem cells and on the tumorigenicity of a tumor comprising the cancer stem cells. Such assays can be used to determine the frequency of cancer stem cells in tumors from animals treated with antibody 64R7 or other agents and can be used to compare that frequency to the frequency of cancer stem cells in tumors from control animals.

Tumors from the Lu45 xenograft study described above were harvested at the end of the study (day 42 of treatment). The tumors were processed and dissociated into single cells. Single cell suspensions derived from 5 tumors of each treatment group were pooled, and the pooled samples were then incubated on ice for 30 min with antibodies that bind mouse cells selectively (α-mouse CD45-biotin 1:200 dilution and rat α-mouse H2Kd-biotin 1:100 dilution, BioLegend, San. Diego, Calif.), followed by addition of streptavidin-labeled magnetic beads (Invitrogen, Carlsbad, Calif.). The mouse cells were removed with the aid of a magnet. The human cells in the suspension were harvested, counted, and stained for cell surface markers and appropriate cell doses (30, 90, and 270 cells) in FACS buffer were mixed in a 1:1 mixture with Matrigel and injected subcutaneously in NOD/SCID mice (10 mice per cell dose per treatment group).

At day 68 post cell injection, the percentage of mice with detectable tumors was determined in all groups injected with the tumor cells from animals treated with a combination of antibody 64R7 and taxol and compared to the percentage of mice with detectable tumors in the control animals injected with tumor cells from animals treated with taxol alone. Cancer stem cell frequency can be calculated using L-Calc™ software (StemCell Technologies Inc.; www.stemcell.com). Briefly, based on Poisson statistics, exactly one cancer stem cell exists among the known number of injected cells if 37% of the animals fail to develop tumors.

On day 68 after injection of the cells, tumor volumes and tumor take rates in the various groups were determined (FIG. 11B). The reduced tumor take rate in the combination treated groups indicated that the cancer stem cell frequency was reduced by treatment with a combination of antibody 64R7 and taxol. Specifically, in the taxol-treated tumors the CSC frequency was 1:44 cells, whereas treatment with a combination of antibody 64R7 and taxol reduced the CSC frequency to 1:144 cells (FIG. 11C).

Example 13

Additional Anti-Jagged Antibodies

Additional anti-Jagged antibodies were produced and screened for binding affinity to Jagged1 and/or Jagged2. Several antibodies were identified including 133R0201, 133R0203, 133R0205, 133R0206, 133R0207, 133R0208, 133R0209, and 133R0210 antibodies.

Binding Affinities

The $K_D$s of antibodies 133R0201, 133R0203 and 133R0205 were determined using a Biacore 2000 system from Biacore Lifescience (GE Healthcare) and compared to $K_D$, of antibody 64R7. As described above in Example 4, recombinant Jagged proteins human Jagged1-Fc (hJag1), mouse Jagged1-His (mJag1), human Jagged2-Fc (hJag2) and mouse Jagged2-Fc (mJag2) were immobilized on a CM5 chip using standard amine-based chemistry (NHS/EDC). Antibodies were serially diluted in 2-fold increments from 100 to 1.0 nM in HBS-P (0.01M HEPES pH7.4, 0.15M NaCl, 0.005% v/v Surfactant P20) and were injected over the chip surface. Kinetic data were collected over time and were fit using the simultaneous global fit equation to yield affinity constants ($K_D$ values) for each antibody (Table 5).

TABLE 5

| Ab | hJag1 (nM) | mJag1 (nM) | hJag2 (nM) | mJag2 (nM) |
|---|---|---|---|---|
| 64R7 | 1.7 | 4.8 | 10.0 | 9.6 |
| 133R0201 | 0.76 | 0.80 | 2.9 | 3.2 |
| 133R0203 | 1.4 | 1.6 | 3.7 | 3.8 |
| 133R0205 | 1.2 | 1.5 | 5.8 | 4.8 |

As observed previously, 64R7 has a higher affinity to Jagged1 than to Jagged2, with the antibody having a slightly higher affinity for the human Jaggeds over the mouse Jaggeds in this assay. Antibody 133R0201 had a higher affinity for human and mouse Jagged 2 as compared to the binding affinity of antibody 64R7. Antibody 133R0201 also had a higher affinity for human and mouse Jagged 1 as compared to the binding affinity of antibody 64R7. Antibodies 133R0203 and 133R0205 had a binding affinity to human Jagged1 that was very similar to the binding affinity of antibody 64R7, while the binding affinity to mouse Jagged1 was observed to be modestly increased. In contrast, antibodies 133R0203 and 133R0205 had a binding affinity to human Jagged2 that was increased as compared to the binding affinity of antibody 64R7.

Example 14

Reporter Assays

The ability of Jagged antibodies 133R0201, 133R0203, 133R0205, 133R0207, 133R0208, 133R0209 and 133R0210 to inhibit Jagged-induced Notch signaling was investigated using a two cell population assay format as described above in Example 6. One population of human PC3 cells was transfected with an expression vector encoding a full-length Notch2 receptor as well as plasmids encoding a Notch-dependent firefly luciferase reporter construct (8xCBF luciferase) and a Renilla luciferase reporter (Promega, Madison Wis.) as an internal transfection control. A second population of human PC3 cells was transfected with an expression vector encoding a full-length cDNA for either hJagged1 or hJagged2. Aliquots of the two cell populations were mixed together and incubated overnight in the presence of antibodies 64R7, 133R0201, 133R0203, 133R0205, 133R0207, 133R0208, 133R0209 and 133R0210 that were serially diluted 1:3 from 50 to 0.2 µg/ml. Luciferase levels were measured 18 hours later using a dual luciferase assay kit (Promega, Madison, Wis.) with firefly luciferase activity normalized to Renilla luciferase activity. Shown in FIGS. 12A and 12B are titrations of the antibodies in this assay. As previously demonstrated, 64R7 was shown to be an inhibitor of both human Jagged 1 and human Jagged2-induced Notch activation. In addition, all of antibodies 133R0201, 133R0203, 133R0205, 133R0207, 133R0208, 133R0209 and 133R0210 were shown to be inhibitors of both human Jagged1 and human Jagged2-induced Notch activation (FIGS. 12A and 12B).

Example 15

Inhibition of Tumor Growth by Anti-Jagged Antibodies in Lung Tumor Model

The anti-tumor activity of antibodies 64R7, 133R0203, and 133R0205 were evaluated in the lung Lu42 tumor xenograft model. Dissociated OMP-Lu42 cells (50,000 per animal) were injected subcutaneously into 6-8 week old male NOD/SCID mice. Tumor growth was monitored weekly and tumor measurements were initiated once tumors were palpable. On day 54, mice with average tumor volumes of 114 mm$^3$ were randomized into 4 groups of 10 animals each. Animals were injected with 15 mg/kg of either control antibody, antibody 64R7, antibody 133R0203, or antibody 13380205. Administration of the antibodies was performed via injection into the intraperitoneal cavity, twice a week. Tumors were measured twice a week and tumor volume was determined using the formula $\frac{1}{2}(a \times b^2)$; where a=length, and b=breadth. Data are expressed as mean and mean±S.E.M. Group means were compared using Student's two-tailed, unpaired t test. Probability (p) values of <0.05 were interpreted as significantly different.

Treatment with antibody 133R0203 resulted in a 28% reduction in tumor growth as compared to treatment with control antibody (FIG. 13, p=0.04). Furthermore, treatment with 133R0205 resulted in a 33% reduction of tumor growth as compared to treatment with control antibody (FIG. 13, p<0.02). Thus, both antibodies 133R0203 and 133R0205 demonstrated anti-tumor growth activity in the Lu42 lung tumor model as a single agent.

Example 16

Inhibition of Tumor Growth by Anti-Jagged Antibodies in Lung Tumor Model

The anti-tumor activity of antibodies 64R7, 133R0201, 133R0203, 133R0205 and 133R206 was evaluated in the lung Lu45 tumor xenograft model. Dissociated OMP-Lu45 cells (50,000 per animal) were injected subcutaneously into 6-8 week old male NOD/SCID mice. Tumor growth was monitored weekly and tumor measurements were initiated once tumors were palpable. On day 41, mice with average tumor volumes of 132 mm$^3$ were randomized into 10 groups of 10 animals each. Animals were injected with control antibody, antibody 64R7, antibody 133R0201, antibody 133R0203, antibody 133R0205, antibody 133R0206 (all at 15 mg/kg), taxol (15 mg/kg), a combination of antibody 64R7 and taxol, a combination of antibody 133R0203 and taxol, or a combination of antibody 133R0205 and taxol. Administration of the antibodies and taxol was performed via injection into the intra-peritoneal cavity, once a week for taxol and twice a week for antibodies. Tumors were measured twice a week and tumor volume was determined using the formula $\frac{1}{2}(a \times b^2)$; where a=length, and b=breadth. Data are expressed as mean and mean±S.E.M. Group means were compared using Student's two-tailed, unpaired t test. Probability (p) values of <0.05 were interpreted as significantly different.

Treatment with antibody 133R0201 resulted in a 24% reduction in tumor growth as compared to treatment with the control antibody (FIG. 14, p=0.03). Furthermore, treatment with a combination of 133R0203 and taxol resulted in a 36% reduction of tumor growth relative to treatment with taxol alone (p=0.01 vs. taxol alone) (FIG. 14). Treatment with a combination of 133R0205 and taxol, also resulted in a reduction of tumor growth relative to treatment with taxol alone. Thus, antibody 133R0201 demonstrated anti-tumor growth activity in the Lu45 lung tumor model as a single agent, and antibodies 133R0203 and 133R0205 displayed anti-tumor growth activity in combination with taxol.

It is understood that the examples and embodiments described herein are for illustrative purposes only and that various modifications or changes in light thereof will be suggested to persons skilled in the art and are to be included within the spirit and purview of this application.

All publications, patents and patent applications cited herein are hereby incorporated by reference in their entirety for all purposes to the same extent as if each individual publication, patent or patent application were specifically and individually indicated to be so incorporated by reference.

What is claimed:

1. An isolated antibody that specifically binds to an extracellular domain of human Jagged, wherein the antibody comprises:
    (a) a heavy chain CDR1 comprising SYWIH (SEQ ID NO:9), a heavy chain CDR2 comprising RIYPGIGSTYYNEKFKD (SEQ ID NO:10), and a heavy chain CDR3 comprising NGGFFDY (SEQ ID NO:11); and a light chain CDR1 comprising RASESVDSYGNSFMH (SEQ ID NO:12), a light chain CDR2 comprising RASNLES (SEQ ID NO:13), and a light chain CDR3 comprising QQSNEDPWT (SEQ ID NO:14);
    (b) a heavy chain CDR1 comprising SYAMH (SEQ ID NO:23), a heavy chain CDR2 comprising VISYDGSNKYYADSVKG (SEQ ID NO:24), AIYPDSSNKYYADSVKG (SEQ ID NO:47), AISPEASNKYYADSVKG (SEQ ID NO:48), or AIYPASSNKYYADSVKG (SEQ ID NO:49), and a heavy chain CDR3 comprising DKYDIPDAFDI (SEQ ID NO:25); and a light chain CDR1 comprising RASQGISNDLA (SEQ ID NO:26), a light chain CDR2 comprising ATSTLQS (SEQ ID NO:27), and a light chain CDR3 comprising QQSYNAPI (SEQ ID NO:28); or
    (c) a heavy chain CDR1 comprising SSNWWS (SEQ ID NO:37), a heavy chain CDR2 comprising EIFHGENTNYNPSLKS (SEQ ID NO:38), and a heavy chain CDR3 comprising NPGIGAAKFDS (SEQ ID NO:39); and a light chain CDR1 comprising KSSQSLLHSDGKTYLY (SEQ ID NO:40), a light chain CDR2 comprising EVSNRFS (SEQ ID NO:41), and a light chain CDR3 comprising MQHIDFP (SEQ ID NO:42).

2. The antibody of claim 1, which comprises:
    (a) a heavy chain variable region having at least about 90% sequence identity to SEQ ID NO:5 and a light chain variable region having at least about 90% sequence identity to SEQ ID NO:7;
    (b) a heavy chain variable region having at least about 90% sequence identity to SEQ ID NO:19, SEQ ID NO:50, SEQ ID NO:51, or SEQ ID NO:52; and a light chain variable region having at least about 90% sequence identity to SEQ ID NO:21; or
    (c) a heavy chain variable region having at least about 90% sequence identity to SEQ ID NO:33 and a light chain variable region having at least about 90% sequence identity to SEQ ID NO:35.

3. The antibody of claim 2, which comprises:
    (a) a heavy chain variable region comprising SEQ ID NO:5; and a light chain variable region comprising SEQ ID NO:7; or
    (b) a heavy chain variable region comprising SEQ ID NO:19, SEQ ID NO:50, SEQ ID NO:51, or SEQ ID NO:52 and a light chain variable region comprising SEQ ID NO:21; or
    (c) a heavy chain variable region comprising SEQ ID NO:33 and a light chain variable region comprising SEQ ID NO:35.

4. The antibody of claim 1, wherein the human Jagged is Jagged1.

5. The antibody of claim 4, wherein the antibody further specifically binds to human Jagged2.

6. The antibody of claim 1, wherein the human Jagged is Jagged2.

7. The antibody of claim 1, which is a recombinant antibody, a monoclonal antibody, a chimeric antibody, a humanized antibody, a human antibody, an antibody fragment, a bispecific antibody.

8. An isolated monoclonal antibody that competes with the antibody of claim 1 for specific binding to an extracellular domain of human Jagged1 or Jagged2.

9. A pharmaceutical composition comprising the antibody of claim 1 and a pharmaceutically acceptable carrier.

10. The antibody of claim 1, which inhibits tumor growth.

11. A method of treating cancer in a subject, comprising administering an effective amount of the antibody of claim 1.

12. The method of claim 11, wherein the cancer is colorectal cancer, breast cancer, prostate cancer, pancreatic cancer, lung cancer, head and neck cancer, or melanoma.

13. The method of claim 11, further comprising administering a therapeutically effective amount of a second therapeutic agent to the subject.

14. The method of claim 13, wherein the second therapeutic agent is a chemotherapeutic agent or a therapeutic antibody.

15. A monoclonal antibody produced by the hybridoma cell line 64M51 on deposit as ATCC Patent Deposit Designation PTA-10468.

16. A humanized form of the antibody of claim 15.

17. An antibody encoded by the polynucleotide deposited with the ATCC as PTA-10470 or as PTA-10469.

18. A polypeptide comprising a sequence selected from the group consisting of SEQ ID NO:5, SEQ ID NO:19, SEQ ID NO:21, SEQ ID NO:33, SEQ ID NO:35, SEQ ID NO:50, SEQ ID NO:51, and SEQ ID NO:52.

19. The antibody of claim 8 which competes with an antibody that comprises a heavy chain CDR1 comprising SYWIH (SEQ ID NO:9), a heavy chain CDR2 comprising RIYPGIGSTYYNEKFKD (SEQ ID NO:10), and a heavy chain CDR3 comprising NGGFFDY (SEQ ID NO:11); and a light chain CDR1 comprising RASESVDSYGNSFMH (SEQ ID NO:12), a light chain CDR2 comprising RASNLES (SEQ ID NO:13), and a light chain CDR3 comprising QQSNEDPWT (SEQ ID NO:14) for binding to an extracellular domain of human Jagged1.

20. The antibody of claim 8 which competes with an antibody that a heavy chain CDR1 comprising SYAMH (SEQ ID NO:23), a heavy chain CDR2 comprising VISYDGSNKYY- ADSVKG (SEQ ID NO:24), AIYPDSSNKYYADSVKG (SEQ ID NO:47), AISPEASNKYYADSVKG (SEQ ID NO:48), or AIYPASSNKYYADSVKG (SEQ ID NO:49), and a heavy chain CDR3 comprising DKYDIPDAFDI (SEQ ID NO:25); and a light chain CDR1 comprising RASQGISNDLA (SEQ ID NO:26), a light chain CDR2 comprising ATSTLQS (SEQ ID NO:27), and a light chain CDR3 comprising QQSYNAPI (SEQ ID NO:28) for binding to an extracellular domain of human Jagged1.

21. The antibody of claim 8 which competes with an antibody that a heavy chain CDR1 comprising SYAMH (SEQ ID NO:23), a heavy chain CDR2 comprising VISYDGSNKYYADSVKG (SEQ ID NO:24), AIYPDSSNKYYADSVKG (SEQ ID NO:47), AISPEASNKYYADSVKG (SEQ ID NO:48), or AIYPASSNKYYADSVKG (SEQ ID NO:49), and a heavy chain CDR3 comprising DKYDIPDAFDI (SEQ ID NO:25); and a light chain CDR1 comprising RASQGISNDLA (SEQ ID NO:26), a light chain CDR2 comprising ATSTLQS (SEQ ID NO:27), and a light chain CDR3 comprising QQSYNAPI (SEQ ID NO:28) for binding to an extracellular domain of human Jagged2.

22. The antibody of claim 8 which competes with an antibody that a heavy chain CDR1 comprising SSNWWS (SEQ ID NO:37), a heavy chain CDR2 comprising EIFHGENTNYNPSLKS (SEQ ID NO:38), and a heavy chain CDR3 comprising NPGIGAAKFDS (SEQ ID NO:39); and a light chain CDR1 comprising KSSQSLLHSDGKTYLY (SEQ ID NO:40), a light chain CDR2 comprising EVSNRFS (SEQ ID NO:41), and a light chain CDR3 comprising MQHIDFP (SEQ ID NO:42) for binding to an extracellular domain of human Jagged1.

23. The antibody of claim 8, which is a humanized antibody.

* * * * *